(12) United States Patent
Uehira et al.

(10) Patent No.: US 8,257,611 B2
(45) Date of Patent: Sep. 4, 2012

(54) OPTICAL FILM AND RETARDATION SHEET, AND LIQUID CRYSTAL COMPOUND

(75) Inventors: Shigeki Uehira, Minami-ashigara (JP); Michitaka Matsuumi, Minami-ashigara (JP); Shinichi Morishima, Minami-ashigara (JP); Mitsuyoshi Ichihashi, Minami-ashigara (JP); Kotaro Yasuda, Minami-ashigara (JP); Hiroshi Takeuchi, Minami-ashigara (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 435 days.

(21) Appl. No.: 12/519,290

(22) PCT Filed: Dec. 14, 2007

(86) PCT No.: PCT/JP2007/074604
§ 371 (c)(1),
(2), (4) Date: Jun. 15, 2009

(87) PCT Pub. No.: WO2008/072794
PCT Pub. Date: Jun. 19, 2008

(65) Prior Publication Data
US 2010/0045901 A1 Feb. 25, 2010

(30) Foreign Application Priority Data

Dec. 15, 2006 (JP) .................. 2006-339233
Apr. 3, 2007 (JP) .................. 2007-097315

(51) Int. Cl.
*C09K 19/00* (2006.01)
*C09K 19/02* (2006.01)
*C09K 19/06* (2006.01)
*C09K 19/52* (2006.01)

(52) U.S. Cl. ........... 252/299.01; 252/299.6; 252/299.61; 252/299.62; 252/299.63; 252/299.64; 252/299.65; 428/1.1; 349/1; 349/56; 349/193; 564/84; 564/156

(58) Field of Classification Search .......... 252/299.01, 252/299.6, 299.61–65; 428/1.1; 430/20; 349/1, 56, 193; 564/84, 156
See application file for complete search history.

(56) References Cited

U.S. PATENT DOCUMENTS 7,976,914 B2 * 7/2011 Fukagawa et al. .......... 428/1.3
2004/0029040 A1 2/2004 Watanabe et al.
2007/0176145 A1 8/2007 Nishikawa et al.
2007/0290168 A1 12/2007 Fukawa et al.
2010/0045901 A1 * 2/2010 Uehira et al. .......... 349/75

FOREIGN PATENT DOCUMENTS

| JP | 10-068816 A | 3/1998 |
| JP | 2002-267838 A | 9/2002 |
| JP | 2004-070344 A | 3/2004 |
| JP | 2005-289980 A | 10/2005 |
| JP | 2007-233376 A | 9/2007 |
| JP | 2007-256494 A | 10/2007 |
| JP | 2007-304287 A | 11/2007 |
| JP | 2008-020896 A | 1/2008 |
| WO | WO 2005/085222 A1 | 9/2005 |
| WO | WO 2006/132404 A1 | 12/2006 |
| WO | WO 2007/091716 A1 | 8/2007 |

OTHER PUBLICATIONS

* PCT/ISA/210 for PCT/JP2007/074604 completed Dec. 2, 2008.
Office Action dated May 3, 2012 issued in corresponding Chinese Patent Application No. 200780046210.2 with partial English Translation.

* cited by examiner

*Primary Examiner* — Geraldina Visconti
(74) *Attorney, Agent, or Firm* — Buchanan Ingersoll & Rooney PC

(57) ABSTRACT

A compound of formula (1): wherein $A_1$ and $A_2$ are —O—, —NR—, —S—, or —CO—, in which R is a hydrogen atom or substituent; Z is one or two atoms selected from a carbon atom or a non-metal atom of Group 14, 15 or 16 in the Periodic Table, and forms a five- or six-membered ring with the C—C=C—C or C=C—C=C; $R_1$, $R_2$, and $R_3$ each are a substituent; m is an integer of 0 to 4; $L_1$ and $L_2$ are a single bond or divalent linking group; X is a non-metal atom of Group 14, 15 or 16 in the Periodic Table, and may have a hydrogen atom or $R_4$; and at least one of R, $R_1$, $R_2$, $R_3$, and $R_4$ is substituted with a polymerizable group; a liquid crystal composition, an optical film, a retardation sheet, a polarizing plate, and a liquid crystal display.

(1)

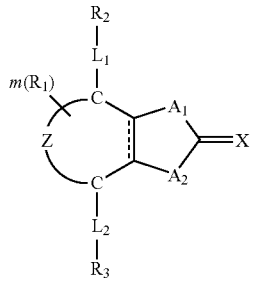

21 Claims, No Drawings

OPTICAL FILM AND RETARDATION SHEET, AND LIQUID CRYSTAL COMPOUND

TECHNICAL FIELD

The present invention relates to a polymerizable compound with reverse wavelength dispersion (or reverse dispersion of wavelength dispersion), a polymerizable liquid crystal compound, and a polymerizable liquid crystal composition. Further, the present invention relates to an optical film carrying the liquid crystal compound immobilized therein. Further, the present invention relates to a retardation sheet (a phase difference plate) having reverse wavelength dispersion of birefringence, such as a broadband λ/4 plate. Further, the present invention relates to a polarizing plate and a liquid crystal display each using the retardation sheet.

BACKGROUND ART

The wavelength plates (or wave plates) have been widely used for attaining high contrast ratios and improving color shift phenomena at wide view angles in color TFT liquid crystal displays of various kinds of display modes, and the like. For prevention of change in color or discoloration, it is needed to make the wavelength plate have a controlled wavelength dispersion of retardation (phase difference), i.e. that the properties of the wavelength plate be constant regardless of the wavelength. Thus, with respect to the wavelength dispersion of retardation, it is necessary that the retardation in the longer wavelength region is larger than the retardation in the shorter wavelength region, namely, the retardation is reverse dispersion of wavelength dispersion.

For example, JP-A-2004-70344 ("JP-A" means unexamined published Japanese patent application) discloses that a retardation sheet with a retardation in the film in-plane direction of reverse wavelength dispersion is extremely low in fluctuation of chromaticity and brightness, and thus it can be used as an excellent polarizing plate with a brightness-improving film. Further, for example, JP-A-2005-289980 discloses that it is possible to improve brightness characteristics and view angle characteristics drastically, by using a retardation sheet of reverse wavelength dispersion having a retardation in the film thickness direction.

However, generally, the wavelength dispersion of films is normal wavelength dispersion, in which the phase dispersion in longer wavelength region is normally smaller than the phase dispersion in shorter wavelength region, and thus, it is difficult to solve the problems above.

To solve the problems above, a method was developed: by bonding a quarter-wavelength plate having a retardation of in-plane birefringent light of ¼ wavelength and a half-wavelength plate having a retardation of birefringent light of ½ wavelength to each other, with their optical axes in the crossed state (see, e.g., JP-A-10-68816). However, for producing the above retardation sheets, a complicated process is required for controlling the optical directions (optical axes and slow phase axes) of the two polymer films.

Also, a method was proposed, which is to apply a liquid crystal composition that shows reverse wavelength dispersion by mixing a rod-shaped liquid crystal with a molecule orienting itself in the direction perpendicular to the major axis of the rod-shaped liquid crystal (see, e.g., JP-A-2002-267838). However, it is very difficult to control the wavelength dispersion arbitrarily by the method, because the mixed molecule is not liquid crystalline and thus, increase of the blending ratio leads to disappearance of liquid crystallinity.

Also, for solving the problems above, a method was disclosed, which utilizes a film that is prepared by applying a polymerizable liquid crystal compound with reverse wavelength dispersion on an oriented film, orienting and immobilizing (see, e.g., JP-A-2005-289980). The method is a favorable method, because it demands no film lamination, is simple to practice, and allows reduction of film thickness. However, the synthetic route for the compounds disclosed in JP-A-2005-289980 is relatively long, and thus, the method is not favorable, considering its production cost.

DISCLOSURE OF INVENTION

For solving the problems above, the present invention contemplates for providing a novel polymerizable liquid crystal compound with reverse wavelength dispersion that can be produced in a simple preparative method, and providing a retardation sheet with reverse wavelength dispersion of its birefringence that can be produced in a simple production process by using the compound. Further, the present invention contemplates for providing a liquid crystal composition, a retardation sheet, and an elliptical polarizing plate, using the novel compound.

After intensive studies to solve the problems above, the inventors of the present invention have found that it is possible to give reverse dispersion of the wavelength dispersion in a film which is obtained by coating an oriented film with a particular material, followed by orienting and then immobilizing the thus-coated material. Thus, the inventors have attained to complete the present invention.

According to the present invention, there is provided the following means:

[1] A compound represented by formula (1):

[Chemical formula 1]

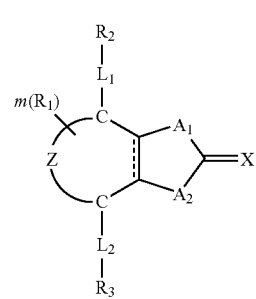

Formula (1)

wherein $A_1$ and $A_2$ each independently represent a group selected from the group consisting of —O—, —NR— (in which R represents a hydrogen atom or a substituent), —S—, and —CO—; Z represents one or two atoms selected from the group consisting of a carbon atom and non-metal atoms belonging to any of Groups 14 to 16 in the Periodic Table, and forms a five- or six-membered ring with the C—C=C—C or C=C—C=C in the formula; $R_1$, $R_2$, and $R_3$ each independently represent a substituent; m represents an integer of 0 to 4; $L_1$ and $L_2$ each independently represent a single bond or a divalent linking group; X represents a non-metal atom belonging to any of Groups 14 to 16 in the Periodic Table, and X may have a hydrogen atom or a substituent $R_4$ bonded thereto; and at least one of R, $R_1$, $R_2$, $R_3$, and $R_4$ is substituted with a polymerizable group.

[2] The compound according to the above item [1], wherein the compound represented by formula (1) is a compound represented by formula (2):

[Chemical formula 2]

Formula (2)

[Structure: ring with $m(R_1)$, $Z$, two C atoms, $A_1$, $A_2$, $L_1$-$R_2$, $L_2$-$R_3$, and =C($R_5$)($R_6$)]

wherein $A_1$ and $A_2$ each independently represent a group selected from the group consisting of —O—, —NR— (in which R represents a hydrogen atom or a substituent), —S—, and —CO—; Z represents one or two atoms selected from the group consisting of a carbon atom and non-metal atoms belonging to any of Groups 14 to 16 in the Periodic Table, and forms a five- or six-membered ring with the C—C=C—C or C=C—C=C in the formula; $R_1$, $R_2$, and $R_3$ each independently represent a substituent; m represents an integer of 0 to 4; $L_1$ and $L_2$ each independently represent a single bond or a divalent linking group; $R_5$ and $R_6$ each independently represent a substituent; and at least one of R, $R_1$, $R_2$, $R_3$, $R_5$, and $R_6$ is substituted with a polymerizable group.

[3] The compound according to the above item [1] or [2], wherein the polymerizable group is an addition polymerization group.

[4] The compound according to any one of the above items [1] to [3], wherein the ring formed by the above Z and C—C=C—C or C=C—C=C in formula (1) or (2) is an aromatic ring.

[5] The compound according to any one of the above items [1] to [4], wherein the ring formed by the above Z and C—C=C—C or C=C—C=C in formula (1) or (2) is a six-membered ring.

[6] The compound according to any one of the above items [1] to [5], wherein $R_2$ and $R_3$ each independently are a phenyl group having a substituted or unsubstituted benzoyloxy group at the 4-position, a phenyl group having a substituted or unsubstituted cyclohexyl group at the 4-position, a cyclohexyl group having a substituted or unsubstituted phenyl group at the 4-position, or a cyclohexyl group having a substituted or unsubstituted cyclohexyl group at the 4-position.

[7] The compound according to any one of the above items [1] to [6], wherein the polymerization group, preferably the addition polymerization group, is a polymerizable group represented by any one of formulae P1, P2, P3, or P4:

[Chemical formula 3]

[Structures of P1, P2, P3, P4 with substituents $R_{511}$, $R_{512}$, $R_{513}$, $R_{521}$, $R_{522}$, $R_{523}$, $R_{531}$, $R_{532}$, $R_{533}$, $R_{541}$, $R_{542}$, $R_{543}$, $R_{544}$, $R_{545}$]

wherein $R_{511}$, $R_{512}$, $R_{513}$, $R_{521}$, $R_{522}$, $R_{523}$, $R_{531}$, $R_{532}$, $R_{533}$, $R_{541}$, $R_{542}$, $R_{543}$, $R_{544}$, and $R_{545}$ each independently represent a hydrogen atom or an alkyl group; and n represents 0 (zero) or 1.

[8] A liquid crystal composition, comprising at lease one of the compound according to any one of the above items [1] to [7].

[9] The liquid crystal composition according to the above item [8], wherein the compound according to any one of the above items [1] to [7] shows a nematic or smectic A phase.

[10] An optically anisotropic film (hereinafter, referred to also as optically anisotropic film (A)), which is formed with the liquid crystal composition according to the above item [8] or [9], wherein the compound according to any one of the above items [1] to [7] is oriented almost vertically and immobilized.

[11] An optically anisotropic film, which is formed with the liquid crystal composition according to the above item [8] or [9], wherein the compound according to any one of the above items [1] to [7] is oriented almost horizontally and immobilized.

[12] An optically anisotropic film, which is formed with the liquid crystal composition according to the above item [8] or [9], wherein the compound according to any one of the above items [1] to [7] is oriented cholesterically and immobilized.

[13] The optically anisotropic film according to the above item [12], wherein the helical axis of the cholesteric phase and the plane direction of a transparent support are crossed to each other almost orthogonally.

[14] A brightness-improving film, comprising a cholesteric liquid crystal film, a quarter-wavelength plate, and an optically anisotropic film placed between them, wherein the optically anisotropic film is the optically anisotropic film (A) according to the above item [10].

[15] An optically anisotropic film, comprising the optically anisotropic film (A) according to the above item [10], and at least one layer of another optically anisotropic film (hereinafter, referred to also as optically anisotropic film (B)).

[16] The optically anisotropic film according to the above item [15], wherein the optically anisotropic film (B) is a positive A plate film.

The optically anisotropic film according to the above item [1,5] or [16], wherein the optically anisotropic film (B) is a positive A plate film that satisfies relationships in mathematical formulae (1) and (II):

$Re(450\text{ nm})/Re(550\text{ nm}) < 1.0$   Mathematical formula (I)

$Re(650\text{ nm})/Re(550\text{ nm}) > 1.0$   Mathematical formula (II)

[18] A retardation sheet, comprising the optically anisotropic film or brightness-improving film according to any one of the above items [10] to [17].

[19] A polarizing plate, comprising the retardation sheet according to the above item [18].

[20] A liquid crystal display device, comprising the retardation sheet according to the above item [18] or the polarizing plate according to the above item [19].

[21] An IPS-mode liquid crystal display device, comprising the optically anisotropic film according to any one of the above items [15] to [17].

[22] A VA-mode liquid crystal display device, comprising the optically anisotropic film according to the above item [11].

[23] A view angle-adjustable liquid crystal display device, comprising the optically anisotropic film according to the above item [12].

Other and further features and advantages of the invention will appear more fully from the following description.

BEST MODE FOR CARRYING OUT INVENTION

Hereinafter, the present invention will be described in detail. The descriptions below may be given based on some representative embodiments or examples of elements of the present invention, but the invention is not meant to be limited to such embodiments or examples. Herein, in the specification, a numerical range expressed using "to" denotes a range including numerical values described before and after the "to" as the minimum value and the maximum value of the range.

Herein, in the present specification, the Re(λ) and the Rth(λ) indicate the in-plane retardation and the retardation in the direction of the thickness, respectively, at the wavelength λ (nm). The Re(λ) can be measured by making light of wavelength λ nm incident in the direction of the normal of the film, in KOBRA 21ADH or WR (each trade name, manufactured by Oji Scientific Instruments).

In the case where the film to be measured can be expressed by a uniaxial or biaxial index ellipsoid (polarizability ellipsoid or refractive index ellipsoid), the Rth(λ) thereof is calculated as follows.

Rth(λ) is calculated using KOBRA 21ADH or WR on the basis of: the above-described Re(λ); retardation values in total six directions measured by making light of wavelength λ nm incident in the normal direction and directions inclined to 50° at an interval of 10° over the normal direction of the film with the in-plane retardation (slow) axis (judged by the KOBRA 21 ADH, or WR) as an inclined axis (a rotation axis) (or with an arbitrary direction in the film plane as a rotation axis when there is no retardation axis); the estimated average refractive index; and, the input value of the film thickness.

In the above-described method, when the film has a retardation value of zero in a direction inclined to a certain degree over the normal direction with the in-plane retardation axis as a rotation axis, the retardation value in a direction inclined to a larger degree than the above-described direction is calculated by KOBRA 21ADH or WR, after the sign of the retardation value is converted to negative.

Alternatively, Rth may also be calculated by mathematical formulae (1) and (2), on the basis of: retardation values measured from arbitrary inclined two directions, with the retardation axis as an inclined axis (a rotation axis) (or with the in-plane arbitrary direction as a rotation axis when there is no retardation axis); the estimated average refractive index; and the input value of the film thickness.

[Mathematical formula 1]

$$Re(\theta) = \left[ nx - \frac{(ny \times nz)}{\sqrt{\left\{ ny \sin\left(\sin^{-1}\left(\frac{\sin(-\theta)}{nx}\right)\right)\right\}^2 + \left\{ nz \cos\left(\sin^{-1}\left(\frac{\sin(-\theta)}{nx}\right)\right)\right\}^2}} \right] \times \frac{d}{\cos\left\{\sin^{-1}\left(\frac{\sin(-\theta)}{nx}\right)\right\}}$$

Mathematical formula (1)

[Mathematical formula 2]

$$Rth = \left(\frac{nx + ny}{2} - nz\right) \times d$$

Mathematical formula (2)

In the mathematical formulas, Re(θ) represents a retardation value in the direction inclined by an angle θ from the normal direction. nx represents a refractive index in the retardation axis direction in the plane, ny represents a refractive index in the direction orthogonal to nx in the plane, and nz represents a refractive index in the direction orthogonal to nx and ny. d represents the thickness of the film.

In the case where the film to be measured cannot be expressed by a uniaxial or biaxial index ellipsoid, i.e. a film having no so-called optic axis, the Rth(λ) thereof is calculated as follows.

Rth(λ) is calculated using KOBRA 21ADH or WR, on the basis of: the above-described Re(λ); retardation values measured in eleven directions, by making light of wavelength λ nm incident in the directions inclined to −50° to +50° at an interval of 100 over the normal direction of the film with the in-plane retardation axis (judged by the KOBRA 21ADH or WR) as an inclined axis (a rotation axis); the estimated average refractive index; and the input value of the film thickness.

In the above measurement methods, as the estimated (hypothetical) value of the average refractive index, use may be made, for example, of values described in "Polymer Handbook" (JOHN WILEY & SONS, INC.) and values described in catalogues of various optical films. When an average refractive index is unknown on a film in interest, the average refractive index may be determined by measuring the same with an Abbe refractometer. Average refractive indexes of major optical films are exemplified in below: cellulose acylate (1.48), cycloolefin polymer (1.52), polycarbonate (1.59), polymethyl methacrylate (1.49), and polystyrene (1.59). KOBRA 21ADH or WR can calculate nx, ny, and nz, by inputting these estimated values of the average refractive index and the film thickness. From the thus-calculated nx, ny, and nz, Nz=(nx−nz)/(nx−ny) is further calculated.

[Polymerizable Compound with Reverse Wavelength Dispersion (Compound Represented by Formula (1) or (2)]

The compound of the present invention is a polymerizable compound with reverse wavelength dispersion that is represented by formula (1). Among the compounds above, the compound represented by formula (2) is preferable.

[Chemical formula 4]

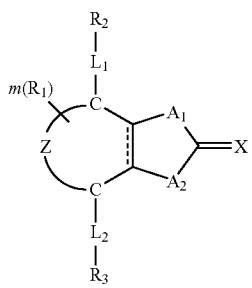

Formula (1)

In formula (1), $A_1$ and $A_2$ each independently represent a group selected from the group consisting of —O—, —NR— (in which R represents a hydrogen atom or a substituent), —S—, and —CO—; Z represents one or two atoms selected from the group consisting of a carbon atom and non-metal atoms belonging to any of Groups 14 to 16 in the Periodic Table, and forms a five- or six-membered ring with the C—C=C—C or C=C—C=C in the formula; $R_1$, $R_2$, and $R_3$ each independently represent a substituent; m represents an integer of 0 to 4; $L_1$ and $L_2$ each independently represent a single bond or a divalent linking group; X represents a non-metal atom belonging to any of Groups 14 to 16 in the Periodic Table, and may have a hydrogen atom or a substituent $R_4$ bonded thereto; and at least one of R, $R_1$, $R_2$, $R_3$, and $R_4$ is substituted with a polymerizable group.

[Chemical formula 5]

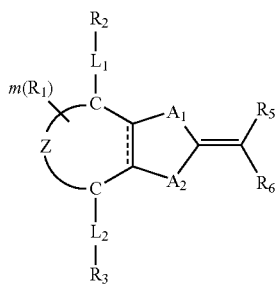

Formula (2)

In formula (2), $A_1$, $A_2$, Z, $R_1$, $R_2$, $R_3$, m, $L_1$, and $L_2$ have the same meanings as those in the formula (1); $R_5$ and $R_6$ each independently represent a substituent; and at least one of R, $R_1$, $R_2$, $R_3$, $R_5$, and $R_6$ is substituted with a polymerizable group.

In formulae (1) or (2), preferable examples of the divalent linking group represented by $L_1$ and $L_2$ are not particularly limited, and favorable examples thereof include the followings. The binding sited to the five- to six-membered ring formed by the groups Z and C—C=C—C or C=C—C=C is assumed to be located to the left side of the linking group exemplified below.

[Chemical formula 6]

-continued

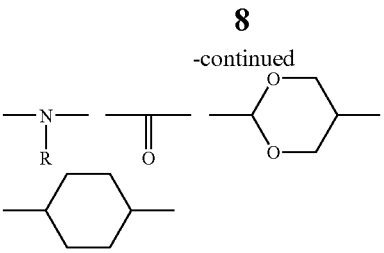

More preferable examples include —O—, —COO—, and —OCO—.

In formulae (1) and (2), Z represents one or two atoms selected from the group consisting of a carbon atom and non-metal atoms belonging to any of Groups 14 to 16 in the Periodic Table, and forms a five- or six-membered ring with the C—C=C—C or C=C—C=C in the formula. The five- to six-membered ring formed by the groups Z and C—C=C—C or C=C—C=C is not particularly limited, and favorable examples thereof include the followings. In the following examples, the dotted line means that the group indicated is bonded to $L_1$ or $L_2$.

[Chemical formula 7]

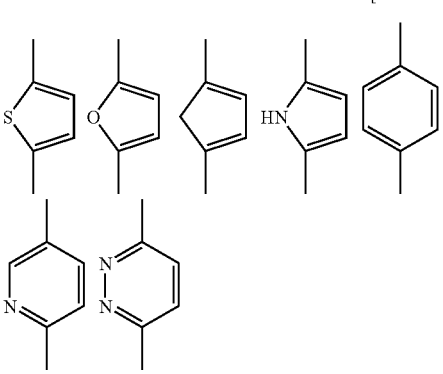

The ring formed by the groups Z and C—C=C—C or C=C—C=C is preferably a six-membered ring. When the ring is a six-membered ring, it is possible to orient the resultant compound at higher orientational order. For the same reason, the ring is also preferably an aromatic ring, more preferably an aromatic six-membered ring.

From these viewpoints and also from the viewpoint of preparation, the ring formed by the groups Z and C—C=C—C or C=C—C=C is preferably a thiophene, benzene or pyridine ring, and most preferably a benzene ring.

In formulae (1) and (2), $R_1$ is a substituent. When there are two or more $R_1$'s, they may be the same or different, or may form a ring. Specific examples of the substituent that can be applied in the present invention, include the followings:

A halogen atom (e.g., a fluorine atom, a chlorine atom, a bromine atom, an iodine atom), an alkyl group (preferably a substituted or unsubstituted, straight-chain or branched allyl group having 1 to 30 carbon atoms, e.g., a methyl group, an ethyl group, a n-propyl group, an isopropyl group, a t-butyl group, a n-octyl group, a 2-ethylhexyl group), a cycloalkyl group (preferably a substituted or unsubstituted cycloalkyl group having 3 to 30 carbon atoms, e.g., a cyclohexyl group, a cyclopentyl group, a 4-n-dodecylcyclohexyl group), a bicycloalkyl group (preferably a substituted or unsubstituted bicycloalkyl group having 5 to 30 carbon atoms, that is, a monovalent group obtained by removing one hydrogen atom from a bicycloalkane having 5 to 30 carbon atoms, e.g., a bicyclo[1,2,2]heptane-2-yl group, a bicyclo[2,2,2]octane-3-yl group),
an alkenyl group (preferably a substituted or unsubstituted alkenyl group having 2 to 30 carbon atoms, e.g., a vinyl group, an allyl group), a cycloalkenyl group (preferably a substituted or unsubstituted cycloalkenyl group having 3 to 30 carbon atoms, that is, a monovalent group obtained by removing one hydrogen atom from a cycloalkene having 3 to 30 carbon atoms, e.g., a 2-cyclopentene-1-yl group, a 2-cyclohexene-1-yl group), a bicycloalkenyl group (a substituted or unsubstituted bicycloalkenyl group, preferably a substituted or unsubstituted bicycloalkenyl group having 5 to 30 carbon atoms, that is, a monovalent group obtained by removing one hydrogen atom from a bicycloalkene having one double bond, e.g., a bicyclo[2,2,1]hepto-2-ene-1-yl group, a bicyclo[2,2,2]oct-2-ene-4-yl group), an alkynyl group (preferably a substituted or unsubstituted alkynyl group having 2 to 30 carbon atoms, e.g., an ethynyl group, a propargyl group),
an aryl group (preferably a substituted or unsubstituted aryl group having 6 to 30 carbon atoms, e.g., a phenyl group, a p-tolyl group, a naphthyl group), a heterocyclic group (preferably a 5- or 6-membered substituted or unsubstituted heterocyclic group, that is a monovalent group obtained by removing one hydrogen atom from an aromatic or non-aromatic heterocyclic compound, more preferably a 5- or 6-membered aromatic heterocyclic group having 3 to 30 carbon atoms, e.g., a 2-furyl group, a 2-thienyl group, a 2-pyrimidinyl group, a 2-benzothiazolyl group), a cyano group, a hydroxyl group, a nitro group, a carboxyl group, an alkoxy group (preferably a substituted or unsubstituted alkoxy group having 1 to 30 carbon atoms, e.g., a methoxy group, an ethoxy group, an isopropoxy group, a t-butoxy group, a n-octyloxy group, a 2-methoxyethoxy group), an aryloxy group (preferably a substituted or unsubstituted aryloxy group having 6 to 30 carbon atoms, e.g., a phenoxy group, a 2-methylphenoxy group, a 4-tert-butylphenoxy group, a 3-nitrophenoxy group, a 2-tetradecanoylaminophenoxy group), a silyloxy group (preferably a silyloxy group having 3 to 20 carbon atoms, e.g., a trimethylsilyloxy group, a tert-butyldimethylsilyloxy group), a heterocyclic oxy group (preferably a substituted or unsubstituted heterocyclic oxy group having 2 to 30 carbon atoms, e.g., a 1-phenyltetrazole-5-oxy group, a 2-tetrahydropyranyloxy group), an acyloxy group (preferably a formyloxy group, a substituted or unsubstituted alkylcarbonyloxy group having 2 to 30 carbon atoms, or a substituted or unsubstituted arylcarbonyloxy group having 6 to 30 carbon atoms, e.g., a formyloxy group, an acetyloxy group, a pivaloyloxy group, a stearoyloxy group, a benzoyloxy group, a p-methoxyphenylcarbonyloxy group), a carbamoyloxy group (preferably a substituted or unsubstituted carbamoyloxy group having 1 to 30 carbon atoms, e.g., an N,N-dimethylcarbamoyloxy group, an N,N-diethylcarbamoyloxy group, a molpholinocarbonyloxy group, an N,N-di-n-octylaminocarbonyloxy group, an N-n-octylcarbamoyloxy group), an alkoxycarbonyloxy group (preferably a substituted or unsubstituted afloxycarbonyloxy group having 2 to 30 carbon atoms, e.g., a methoxycarbonyloxy group, an ethoxycarbonyloxy group, a tert-butoxycarbonyloxy group, a n-octylcarbonyloxy group), an aryloxycarbonyloxy group (preferably a substituted or unsubstituted aryloxycarbonyloxy group having 7 to 30 carbon atoms, e.g., a phenoxycarbonyloxy group, a p-methoxyphenoxycarbonyloxy group, a p-n-hexadecyloxyphenoxycarbonyl oxy group),
an amino group (preferably an amino group, a substituted or unsubstituted alkylamino group having 1 to 30 carbon atoms, or a substituted or unsubstituted anilino group having 6 to 30 carbon atoms, e.g., an amino group, a methylamino group, a dimethylamino group, an anilino group, an N-methyl-anilino group, a diphenylamino group), an acylamino group (preferably a formylamino group, a substituted or unsubstituted alkylcarbonylamino group having 1 to 30 carbon atoms, or a substituted or unsubstituted arylcarbonylamino group having 6 to 30 carbon atoms, e.g., a formylamino group, an acetylamino group, a pivaloylamino group, a lauroylamino group, a benzoylamino group), an aminocarbonylamino group (preferably a substituted or unsubstituted aminocarbonylamino group having 1 to 30 carbon atoms, e.g., a carbamoylamino group, an N,N-dimethylaminocarbonylamino group, an N,N-diethylaminocarbonylamino group, a morpholinocarbonylamino group), an alkoxycarbonylamino group (preferably a substituted or unsubstituted alkoxycarbonylamino group having 2 to 30 carbon atoms, e.g., a methoxycarbonylamino group, an ethoxycarbonylamino group, a tert-butoxycarbonylamino group, a n-octadecyloxycarbonylamino group, an N-methyl-methoxycarbonylamino group), an aryloxycarbonylamino group (preferably a substituted or unsubstituted aryloxycarbonylamino group having 7 to 30 carbon atoms, e.g., a phenoxycarbonylamino group, a p-chlorophenoxycarbonylamino group, a m-n-octyloxyphenoxycarbonylamino group),
a sulfamoylamino group (preferably a substituted or unsubstituted sulfamoylamino group having 0 (zero) to 30 carbon atoms, e.g., a sulfamoylamino group, an N,N-dimethylaminosulfonylamino group, an N-n-octylaminosulfonylamino group), an alkyl- or aryl-sulfonylamino group (preferably a substituted or unsubstituted alkylsulfonylamino group having 1 to 30 carbon atoms, or a substituted or unsubstituted arylsulfonylamino group having 6 to 30 carbon atoms, e.g., a methylsulfonylamino group, a butylsulfonylamino group, a phenylsulfonylamino group, a 2,3,5-trichlorophenylsulfonylamino group, a p-methylphenylsulfonylamino group), a mercapto group, an alkylthio group (preferably a substituted or unsubstituted alkylthio group having 1 to 30 carbon atoms, e.g., a methylthio group, all ethylthio group, a n-hexadecylthio group), an arylthio group (preferably a substituted or unsubstituted arylthio group having 6 to 30 carbon atoms, e.g., a phenylthio group, a p-chlorophenylthio group, a m-methoxyphenylthio group), a heterocyclic thio group (preferably a substituted or unsubstituted heterocyclic thio group having 2 to 30 carbon atoms, e.g., a 2-benzothiazolylthio group, a 1-phenyltetrazol-5-yl thio group),
a sulfamoyl group (preferably a substituted or unsubstituted sulfamoyl group having 0 (zero) to 30 carbon atoms, e.g., an N-ethylsulfamoyl group, an N-(3-dodecyloxypropyl)sulfamoyl group, an N,N-dimethylsulfamoyl group, an N-acetylsulfamoyl group, an N-benzoylsulfarnoyl group, an N—(N'-phenylcarbamoyl)sulfamoyl group), a sulfo group, an alkyl- or aryl-sulfinyl group (preferably a substituted or unsubstituted alkylsulfinyl group having 1 to 30 carbon atoms, or a substituted or unsubstituted arylsulfinyl group having 6 to 30 carbon atoms, e.g., a methylsulfinyl group, an ethylsulfinyl group, a phenylsulfinyl group, a p-methylphenylsulfinyl group), an alkyl- or aryl-sulfonyl group (preferably a substituted or unsubstituted alkylsulfonyl group having 1 to 30 carbon atoms, or a substituted or unsubstituted arylsulfonyl group having 6 to 30 carbon atoms, e.g., a methylsulfonyl group, an ethylsulfonyl group, a phenylsulfonyl group, a p-methylphenylsulfonyl group),
an acyl group (preferably a formyl group, a substituted or unsubstituted alkylcarbonyl group having 2 to 30 carbon atoms, or a substituted or unsubstituted arylcarbonyl group having 7 to 30 carbon atoms, e.g., an acetyl group, a pivaloylbenzoyl group), an aryloxycarbonyl group (preferably a substituted or unsubstituted aryloxycarbonyl group having 7 to 30 carbon atoms, e.g., a phenoxycarbonyl group, an o-chlorophenoxycarbonyl group, a m-nitrophenoxycarbonyl group, a p-tert-butylphenoxycarbonyl group), an alkoxycarbonyl group (preferably a substituted or unsubstituted alkoxycarbonyl group having 2 to 30 carbon atoms, e.g., a methoxycarbonyl group, an ethoxycarbonyl group, a tert-butoxycarbonyl group, a n-octadecyloxycarbonyl group), a carbamoyl group (preferably a substituted or unsubstituted carbamoyl group having 1 to 30 carbon atoms, e.g., a carbamoyl group, an N-methylcarbamoyl group, an N,N-dimethylcarbamoyl group, an N,N-di-n-octylcarbamoyl group, an N-(methylsulfonyl)carbamoyl group),
an aryl- or heterocyclic-azo group (preferably a substituted or unsubstituted arylazo group having 6 to 30 carbon atoms, or a substituted or unsubstituted heterocyclic azo group having 3 to 30 carbon atoms, e.g., a phenylazo group, a p-chlorophenylazo group, a 5-ethylthio-1,3,4-thiadiazole-2-yl azo group), an imido group (preferably an N-succinimido group, an N-phthalimido group), a phosphino group (preferably a substituted or unsubstituted phosphino group having 2 to 30 carbon atoms, e.g., a dimethylphosphino group, a diphenylphosphino group, a methylphenoxyphosphino group), a phosphinyl group (preferably a substituted or unsubstituted phosphinyl group having 2 to 30 carbon atoms, e.g., a phosphinyl group, a dioctyloxyphosphinyl group, a diethoxyphosphinyl group), a phosphinyloxy group (preferably a substituted or unsubstituted phosphinyloxy group having 2 to 30 carbon atoms, e.g., a diphenoxyphosphinyloxy group, a dioctyloxyphosphinyloxy group), a phosphinylamino group (preferably a substituted or unsubstituted phosphinylamino group having 2 to 30 carbon atoms, e.g., a dimethoxyphosphinylamino group, a dimethylaminophosphinylamino group), and a silyl group (preferably a substituted or unsubstituted silyl group having 3 to 30 carbon atoms, e.g., a trimethylsilyl group, a tert-butyldimethylsilyl group, a phenyldimethylsilyl group).

Of the above-mentioned substituents, those having a hydrogen atom(s) may be further substituted with any of the above groups in place of the hydrogen atom(s). Examples of such a functional group include an alkylcarbonylaminosulfonyl group, an arylcarbonylaminosulfonyl group, an alkylsulfonylaminocarbonyl group, and an arylsulfonylaminocarbonyl group. Specific examples thereof include a methylsulfonylaminocarbonyl group, a p-methylphenylsulfonylaminocarbonyl group, an acetylaminosulfonyl group, and a benzoylaminosulfonyl group.

$R_1$ is preferably a halogen atom, an alkyl group, an alkenyl group, an aryl group, a heterocyclic group, a hydroxyl group, a carboxyl group, an alkoxy group, an aryloxy group, an acyloxy group, a cyano group, or an amino group; and more preferably a halogen atom, an alkyl group, a cyano group or an alkoxy group.

When there are two or more $R_1$ groups that form a ring by bonding together, the ring is preferably a five- to eight-membered ring, more preferably a five- or six-membered ring, and most preferably a six-membered ring.

In formulae (1) and (2), m represents the substitution number of $R_1$ that may vary according to the structure of the ring formed by the groups Z and C—C═C—C or C═C—C═C. m is 0 at the lowest, and 4 at the highest when Z represents two carbon atoms and the ring formed by the groups Z and C—C═C—C or C═C—C═C is not aromatic. m is preferably 0 or 1, more preferably 0.

In formulae (1) and (2), $R_2$ and $R_3$ each independently represent a substituent. Examples thereof include those of $R_1$ described above. $R_2$ and $R_3$ are located in the longitudinal direction of the molecule in the compound represented by formula (1) or (2).

The compound represented by formula (1) or (2) preferably shows liquid crystallinity. As described in "Handbook of Liquid crystals" (Maruzen), Chapter 3, "Molecular structure and liquid crystallinity", it is necessary for the element for expressing liquid crystallinity to have a rigid region so-called core and a flexible region so-called side chain. For that reason, at least one rigid region, i.e., a cyclic region, is preferably present as the substituent for $R_2$ and $R_3$. $R_2$ and $R_3$ preferably represent a substituted or unsubstituted phenyl group, or a substituted or unsubstituted cyclohexyl group. $R_2$ and $R_3$ each preferably represent a phenyl group having a substituent, or a cyclohexyl group having a substituent; more preferably a phenyl group having a substituent at the 4-position, or a cyclohexyl group having a substituent at the 4-position; and further preferably a phenyl group having a 4-substituted benzoyloxy group at the 4-position, a phenyl group having a 4-substituted cyclohexyl group at the 4-position, a cyclohexyl group having a 4-substituted phenyl group at the 4-position, or a cyclohexyl group having a 4-substituted cyclohexyl group at the 4-position.

Further, even though there are stereoisomeric forms, cis- and trans-forms, for the cyclohexyl group having a substituent at the 4-position, the present invention is not limited to any of them and a mixture of those may also be used, and the trans-cyclohexyl group is preferable.

In the formulae (1) and (2), $R_5$ and $R_6$ each independently represent a substituent. Examples thereof include those of $R_1$ described above. Preferably, at least one of $R_5$ and $R_6$ is an electron-withdrawing group having a Hammett's substitutent constant up value of more than zero (0), and it more preferably has an electron-withdrawing group having a up value of 0 to 1.5. Examples of such a group include a trifluoromethyl group, a cyano group, a carbonyl group, and a nitro group. $R_5$ and $R_6$ may bond together to form a ring.

Herein, Hanmett's substituent constants $\sigma_p$ and $\sigma_m$ are described in detail in such books as "Hammett Soku—Kozo to Hannousei—," written by Naoki Inamoto (Maruzen); "Shin-jikken Kagaku-koza 14/Yukikagoubutsu no Gosei to Hanno V," page 2605 (edited by Nihonkagakukai, Maruzen); "Riron Yukikagaku Kaisetsu," written by Tadao Nakaya, page 217 (Tokyo Kagakudojin); and "Chemical Review" Vol. 91, pages 165 to 195 (1991), etc.

In formulae (1) and (2), $A_1$ and $A_2$ each independently represent a group selected from the group consisting of —O—, —NR— (in which R is a hydrogen atom or a substituent), —S—, and —CO—; and preferably —O—, —NR— (in which R represents a substituent, for example, any of those exemplified for $R_1$ described above), or —S—.

In formula (1), X represents a nonmetal atom of any of Groups 14 to 16 in the periodic table of elements. X may have a hydrogen atom or a substituent. X is preferably ═O, ═S, ═NR$_4$, or ═C(R$_5$)R$_6$ (in which R$_4$, R$_5$ and R$_6$ each independently represent a substituent, for example, any of those exemplified for $R_1$ above).

The liquid crystal compound of the present invention has a polymerizable group, which can prevent change in retardation, for example by heat, when used in a retardation sheet or the like. The polymerizable group is preferably bonded at a terminal of the molecule of the compound in interest.

In formulae (1) and (2), at least one of R, $R_1$, $R_2$, $R_3$, $R_5$, and $R_6$ is substituted with a polymerizable group. The number of polymerizable groups is preferably 1 to 6, more preferably 1 to 4, and most preferably 1 to 3. The group preferably substituted with a polymerizable group is $R_2$, $R_3$, $R_5$, or $R_6$.

The polymerizable group substituting on at least one of R, $R_1$, $R_2$, $R_3$, $R_5$, and $R_6$ is preferably a group reactive in addition-polymerization or polycondensation reaction. Such a polymerizable group is preferably a polymerizable ethylenically unsaturated group or a ring-opening polymerizable group. Examples of the polymerizable group are set forth below.

[Chemical formula 8]

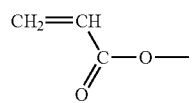

(M-1)

-continued

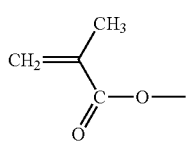
(M-2)

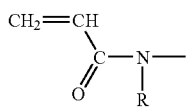
(M-3)

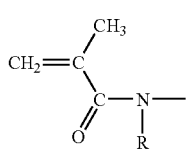
(M-4)

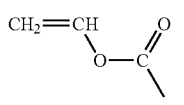
(M-5)

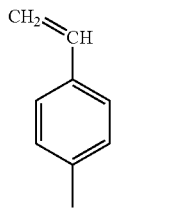
(M-6)

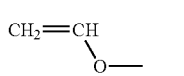
(M-7)

Further, the polymerizable group is more preferably a group that is able to undergo an addition polymerization reaction. Such a polymerizable group is preferably a polymerizable ethylenically unsaturated group or a ring-opening polymerizable group.

The polymerizable group is preferably a group represented by any one of formulae P1, P2, P3, and P4.

[Chemical formula 9]

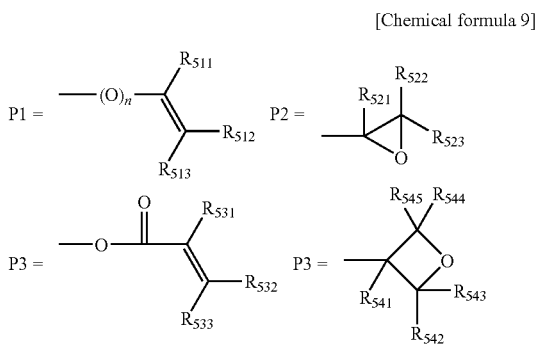

In the formulas, $R_{511}$, $R_{512}$, $R_{513}$, $R_{521}$, $R_{522}$, $R_{523}$, $R_{531}$, $R_{532}$, $R_{533}$, $R_{541}$, $R_{542}$, $R_{543}$, $R_{544}$ and $R_{545}$ each independently represent a hydrogen atom or an alkyl group; and n represents 0 (zero) or 1.

$R_{511}$, $R_{512}$, and $R_{513}$ in the polymerizable group P1, each independently represent a hydrogen atom or an alkyl group.

The group to give, for example, an alkoxy, alkoxycarbonyl or alkoxycarbonyloxy group whose terminal is substituted with the polymerizable group P1, represents an allkyleneoxy group (e.g. an alkyleneoxy group, such as ethyleneoxy, propyleneoxy, butyleneoxy, pentyleneoxy, hexyleneoxy, and heptyleneoxy; and an ether bond-containing substituted allkyleneoxy group, such as ethyleneoxyethoxy), an alkyleneoxycarbonyloxy group (e.g. an alkyleneoxycarbonyloxy group, such as ethyleneoxycarbonyloxy, propyleneoxycarbonyloxy, butyleneoxycarbonyloxy, pentyleneoxycarbonyloxy, hexyleneoxycarbonyloxy, and heptyleneoxycarbonyloxy; and an ether bond-containing substituted alkyleneoxycarbonyloxy group, such as ethyleneoxyethoxycarbonyloxy), or an alkyleneoxycarbonyl group (e.g. an alkyleneoxycarbonyl group, such as ethyleneoxycarbonyl group, propyleneoxycarbonyl group, butyleneoxycarbonyl group, pentyleneoxycarbonyl group, hexyleneoxycarbonyl group, and heptyleneoxycarbonyl group; or an ether bond-containing substituted alkyleneoxycarbonyl group, such as ethyleneoxyethoxycarbonyl group). The polymerizable group P1 may be directly bonded to an aromatic ring. The same is applied to the cases where the terminal substituent is the polymerizable group P2, P3, or P4.

n represents an integer of 0 to 1, preferably n is 1. When n is 1, the polymerizable group P1 represents a substituted or unsubstituted vinyl ether group. The groups $R_{511}$ and $R_{513}$ of the group P1 each independently represent a hydrogen atom, or an alkyl group (e.g. methyl, ethyl, n-propyl, isopropyl, n-butyl, pentyl, hexyl, heptyl, octyl, and nonyl; and preferably a lower alkyl group, such as methyl and ethyl, more preferably methyl). Preferable examples of combination include those in which $R_{511}$ represents a methyl group and $R_{513}$ represents a hydrogen atom, or $R_{511}$ and $R_{513}$ each represent a hydrogen atom.

The group $R_{512}$ represents a hydrogen atom, or a substituted or unsubstituted allyl group (e.g. methyl, ethyl, n-propyl, isopropyl, n-butyl, pentyl, hexyl, heptyl, octyl, nonyl, 2-chloroethyl, 3-methoxyethyl, and methoxyethoxyethyl; and preferably a lower alkyl group, such as methyl and ethyl, more preferably methyl). The group $R_{512}$ is preferably a hydrogen atom or a lower alkyl group, more preferably a hydrogen atom. Therefore, it is preferable to use, as the polymerizable group P1, an unsubstituted vinyloxy group, which is a functional group high in polymerization activity in general.

The polymerizable group P2 represents a substituted or unsubstituted oxirane group. The groups $R_{521}$ and $R_{522}$ of the group P2 each independently represent a hydrogen atom, or an allyl group (e.g. methyl, ethyl, n-propyl, isopropyl, n-butyl, pentyl, hexyl, heptyl, octyl, and nonyl; and preferably a lower alkyl group, such as methyl and ethyl, more preferably methyl). It is preferable that $R_{521}$ and $R_{522}$ each are a hydrogen atom.

The group $R_{523}$ represents a hydrogen atom, or a substituted or unsubstituted alkyl group (e.g. methyl, ethyl, n-propyl, isopropyl, n-butyl, pentyl, hexyl, heptyl, octyl, nonyl, 2-chloroethyl, 3-methoxyethyl, and methoxyethoxyethyl; and preferably a lower alkyl group, such as methyl and ethyl, more preferably methyl). The group $R_{523}$ is preferably a hydrogen atom, or a lower allyl group, such as methyl, ethyl, or n-propyl.

The polymerizable group P3 represents a substituted or unsubstituted acryl group. The groups $R_{531}$ and $R_{533}$ of the group P3 each independently represent a hydrogen atom, or an alkyl group (e.g. methyl, ethyl, n-propyl, isopropyl, n-butyl, pentyl, hexyl, heptyl, octyl, and nonyl; and preferably a lower alkyl group, such as methyl and ethyl, more preferably methyl). Preferable examples of combination include those in which $R_{531}$ represents a methyl group and $R_{533}$ represents a hydrogen atom, or $R_{531}$ and $R_{533}$ each represent a hydrogen atom.

The group $R_{532}$ represents a hydrogen atom, or a substituted or unsubstituted alkyl group (e.g. methyl, ethyl, n-propyl, isopropyl, n-butyl, pentyl, hexyl, heptyl, octyl, nonyl, 2-chloroethyl, 3-methoxyethyl, and methoxyethoxyethyl;

and preferably a lower alkyl group, such as methyl and ethyl, more preferably methyl). The group $R_{532}$ is preferably a hydrogen atom. Therefore, it is preferable to use, as the polymerizable group P3, a functional group high in polymerization activity in general, such as an unsubstituted acryloxy group, a methacryloxy group, or a crotonyloxy group.

The polymerizable group P4 represents a substituted or unsubstituted oxetane group. The groups $R_{542}$, $R_{543}$, $R_{544}$, and $R_{545}$ on the group P4 each independently represent a hydrogen atom, or an allyl group (e.g. methyl, ethyl, n-propyl, isopropyl, n-butyl, pentyl, hexyl, heptyl, octyl, and nonyl; and preferably a lower alkyl group, such as methyl and ethyl, more preferably methyl). It is preferable that $R_{542}$, $R_{543}$, $R_{544}$, and $R_{545}$ each are a hydrogen atom.

$R_{541}$ represents a hydrogen atom, or a substituted or unsubstituted alkyl group (e.g. methyl, ethyl, n-propyl, isopropyl, n-butyl, pentyl, hexyl, heptyl, octyl, nonyl, 2-chloroethyl, 3-methoxyethyl, and methoxyethoxyethyl; and preferably a lower alkyl group, such as methyl and ethyl, more preferably methyl). $R_{541}$ is preferably a hydrogen atom, or a lower alkyl group, such as methyl, ethyl, or n-propyl.

Specific examples of the compound represented by formula (1) or (2) are shown below, but the invention is not meant to be limited to those. In the following description, when the exemplified compounds shown below are referred to, the number X put in parentheses, that is, "(X)" as attached to a chemical structure formula of the exemplified compound is used to express the compound as "Exemplified compound (X)", unless otherwise specified.

[Chemical formula 10]

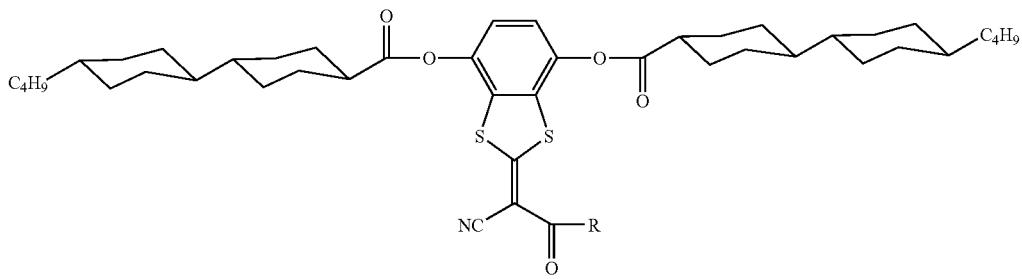

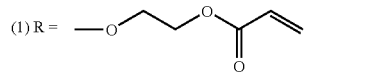

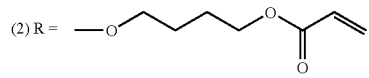

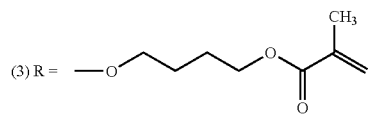

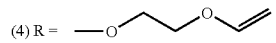

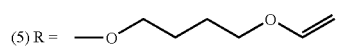

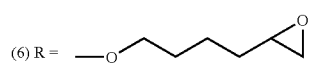

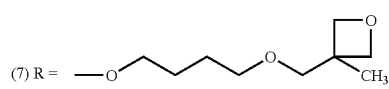

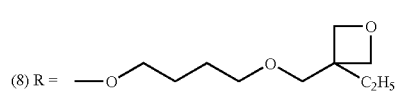

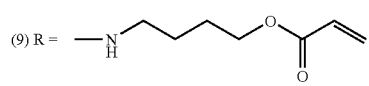

[Chemical formula 11]
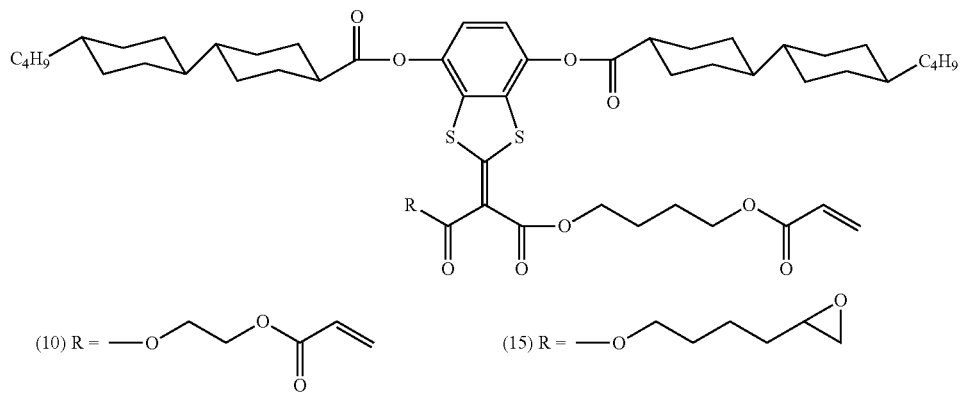
(10) R = —O−CH₂CH₂−O−C(=O)−CH=CH₂
(11) R = —O−(CH₂)₄−O−C(=O)−CH=CH₂
(12) R = —O−(CH₂)₄−O−C(=O)−C(CH₃)=CH₂
(13) R = —O−CH₂CH₂−O−CH=CH₂
(14) R = —O−(CH₂)₄−O−CH=CH₂
(15) R = —O−(CH₂)₄−(epoxide)
(16) R = —O−(CH₂)₄−O−CH₂−(3-methyloxetane)
(17) R = —O−(CH₂)₄−O−CH₂−(3-ethyloxetane)
(18) R = —NH−(CH₂)₄−O−C(=O)−CH=CH₂
(19) R = —CH₃
[Chemical formula 12]
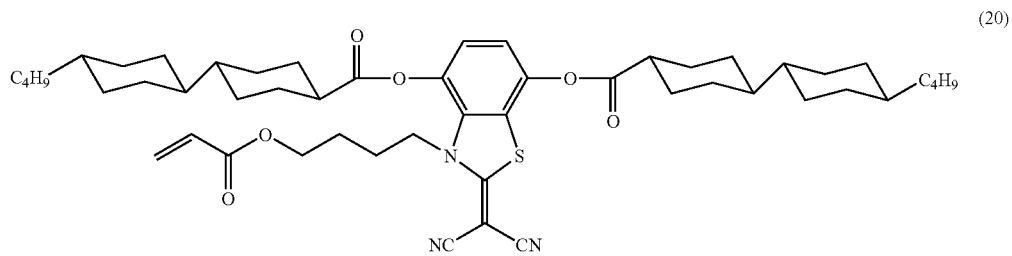
(20)
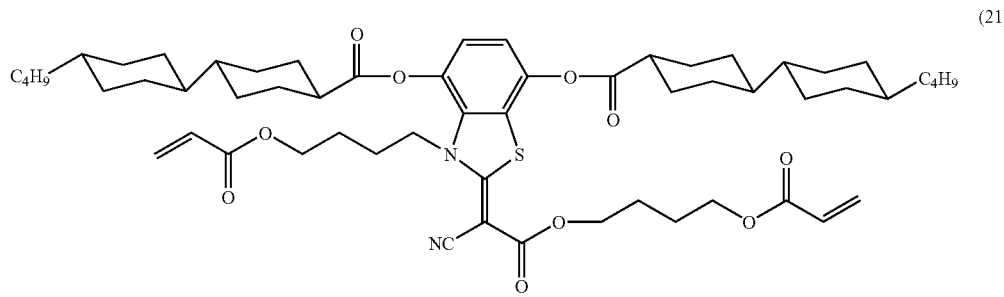
(21)

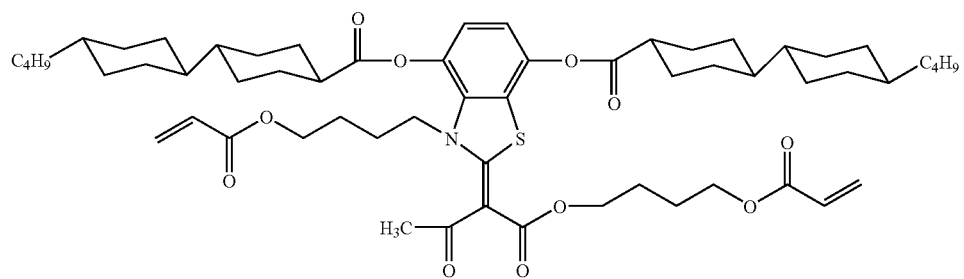
(22)
[Chemical formula 13]
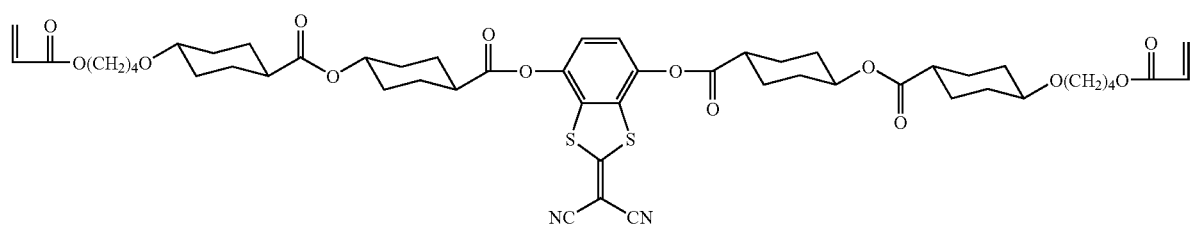
(23)
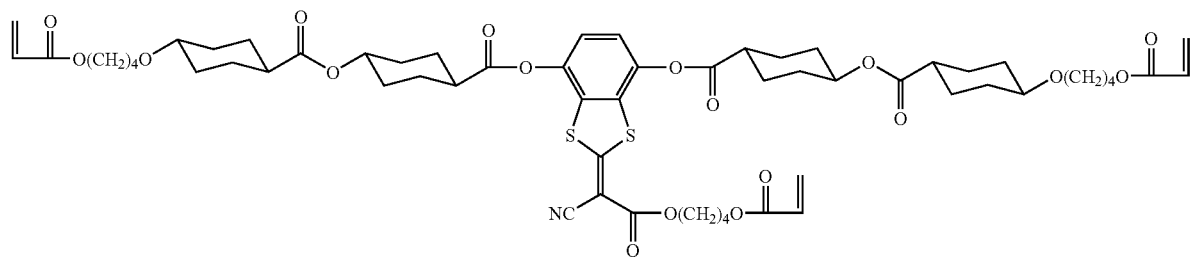
(24)
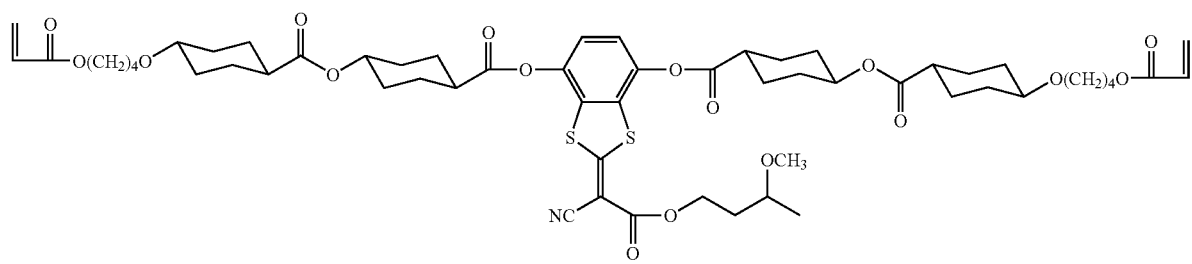
(25)

[Chemical formula 14]
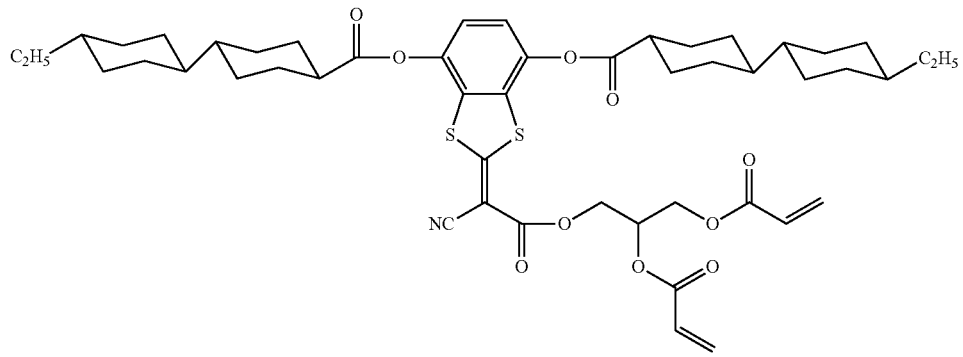
(26)
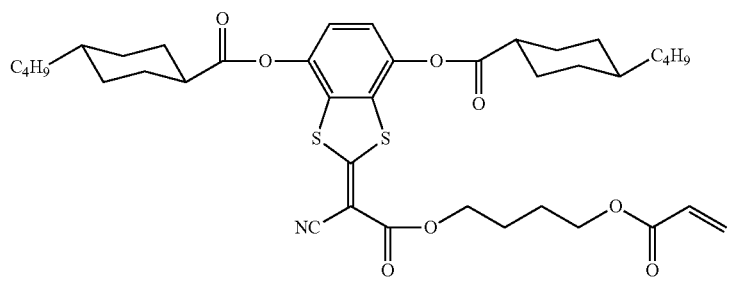
(27)
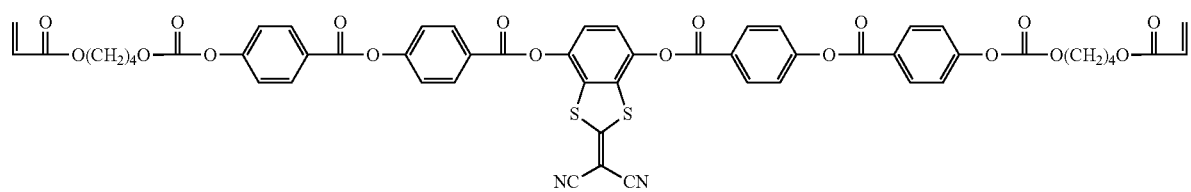
(28)
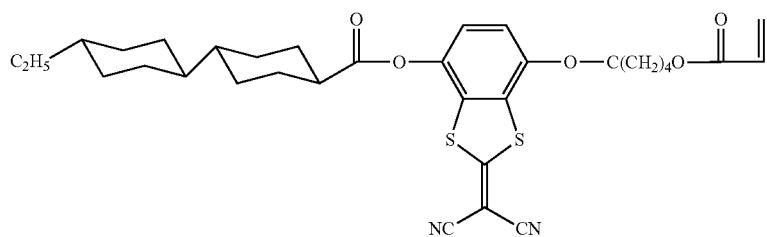
(29)
[Chemical formula 15]
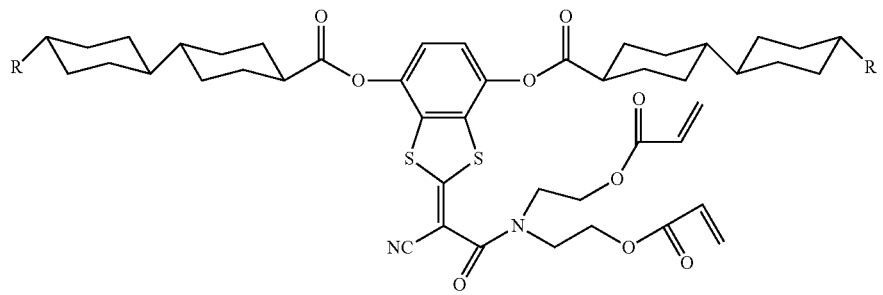
R = —$C_5H_{11}$ (30)
—$C_4H_9$ (31)
—$C_3H_7$ (32)
—$C_2H_5$ (33)

-continued
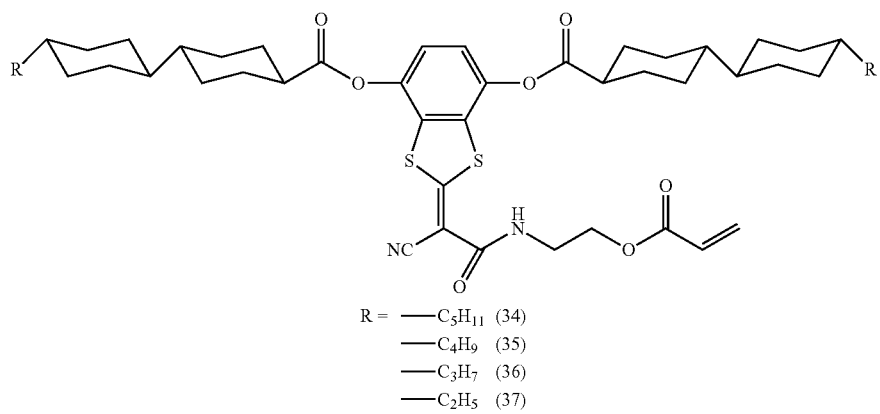
R = —C₅H₁₁ (34)
—C₄H₉ (35)
—C₃H₇ (36)
—C₂H₅ (37)
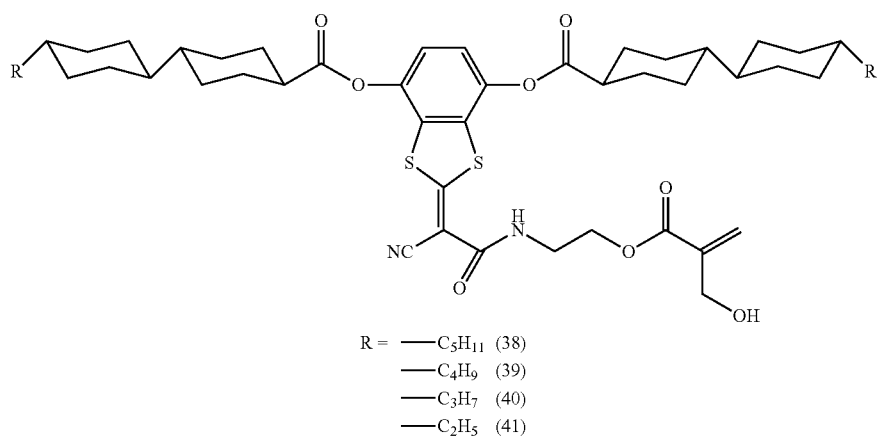
R = —C₅H₁₁ (38)
—C₄H₉ (39)
—C₃H₇ (40)
—C₂H₅ (41)
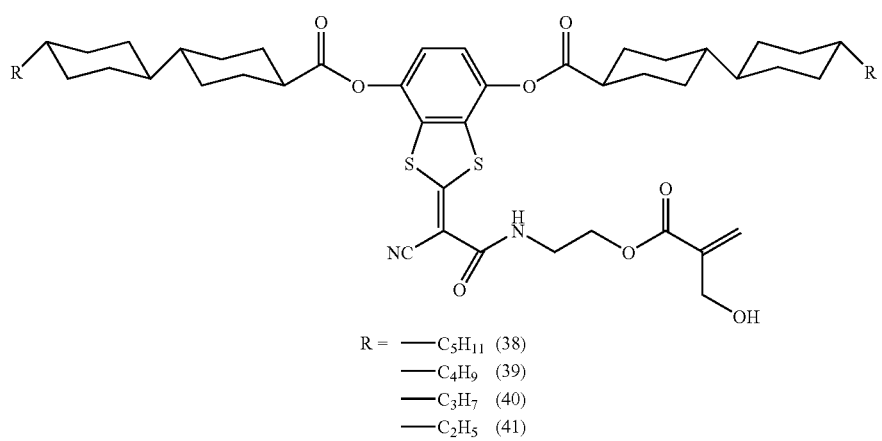
R = —C₅H₁₁ (38)
—C₄H₉ (39)
—C₃H₇ (40)
—C₂H₅ (41)
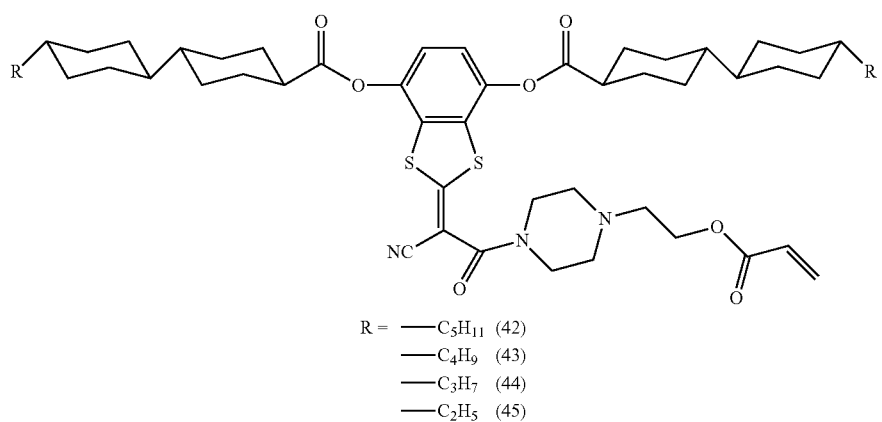
R = —C₅H₁₁ (42)
—C₄H₉ (43)
—C₃H₇ (44)
—C₂H₅ (45)

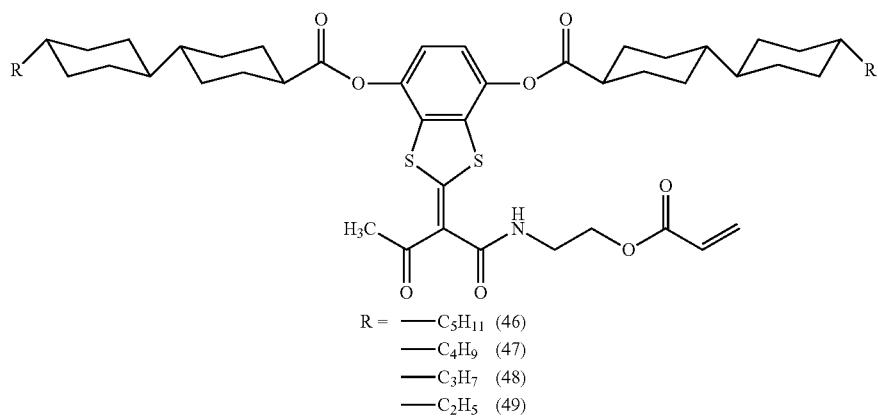
R = —C₅H₁₁ (46)
—C₄H₉ (47)
—C₃H₇ (48)
—C₂H₅ (49)
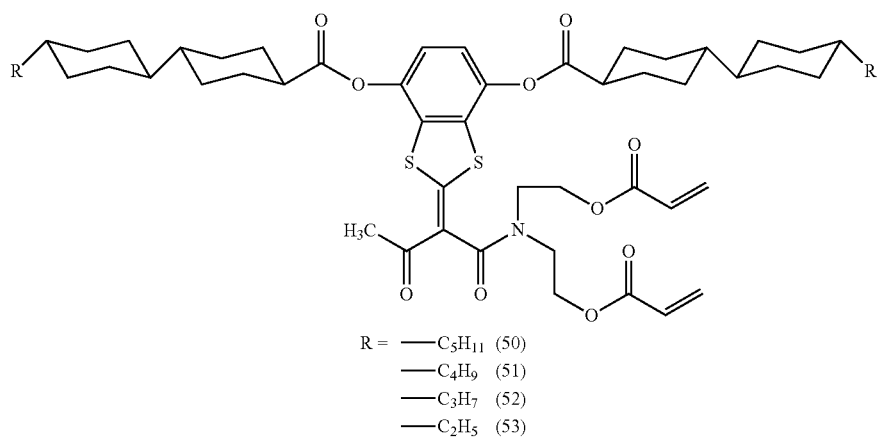
R = —C₅H₁₁ (50)
—C₄H₉ (51)
—C₃H₇ (52)
—C₂H₅ (53)
[Chemical formula 16]
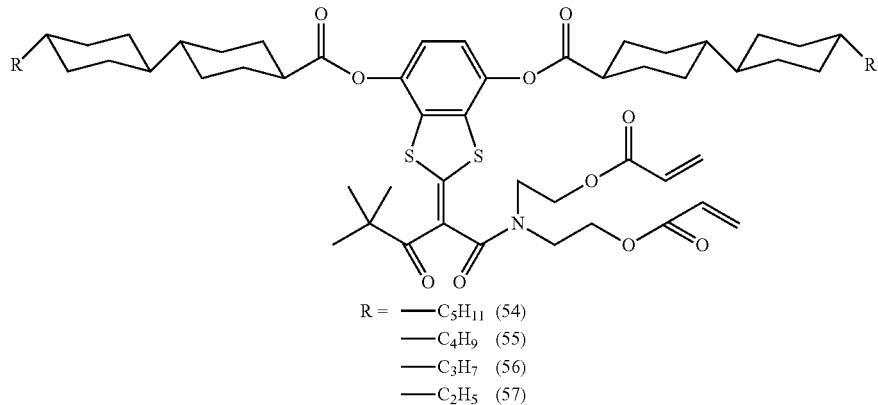
R = —C₅H₁₁ (54)
—C₄H₉ (55)
—C₃H₇ (56)
—C₂H₅ (57)

-continued
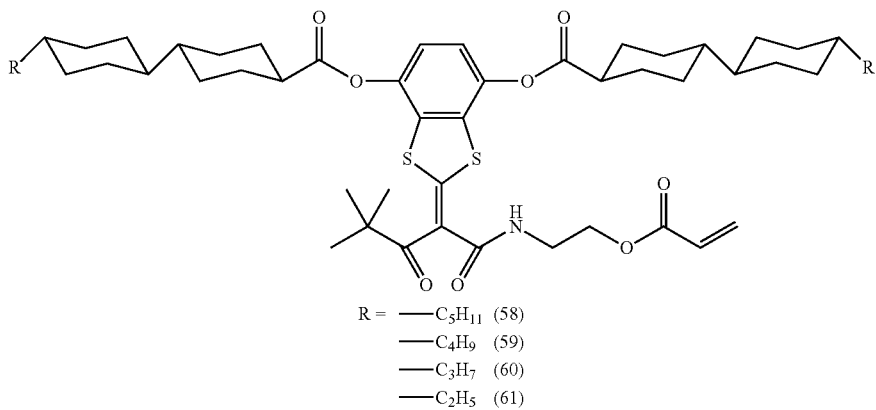
R = —C$_5$H$_{11}$ (58)
—C$_4$H$_9$ (59)
—C$_3$H$_7$ (60)
—C$_2$H$_5$ (61)
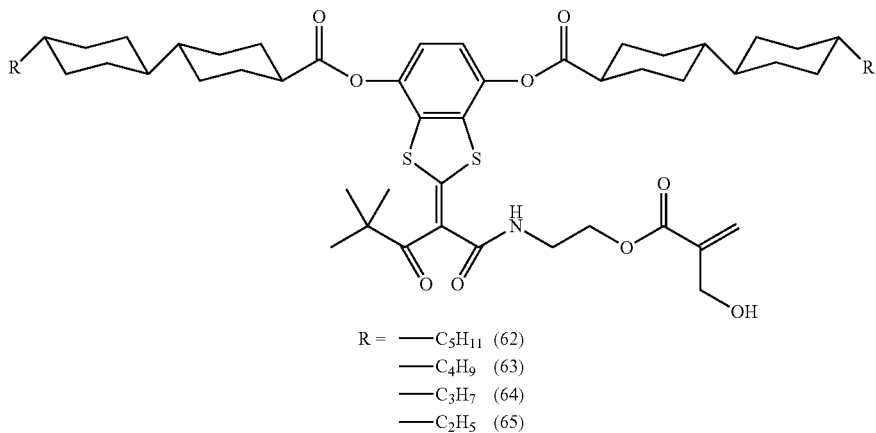
R = —C$_5$H$_{11}$ (62)
—C$_4$H$_9$ (63)
—C$_3$H$_7$ (64)
—C$_2$H$_5$ (65)
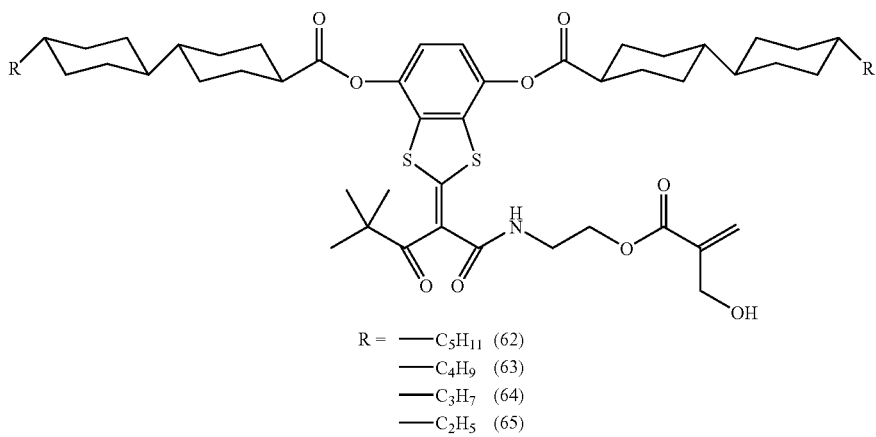
R = —C$_5$H$_{11}$ (62)
—C$_4$H$_9$ (63)
—C$_3$H$_7$ (64)
—C$_2$H$_5$ (65)
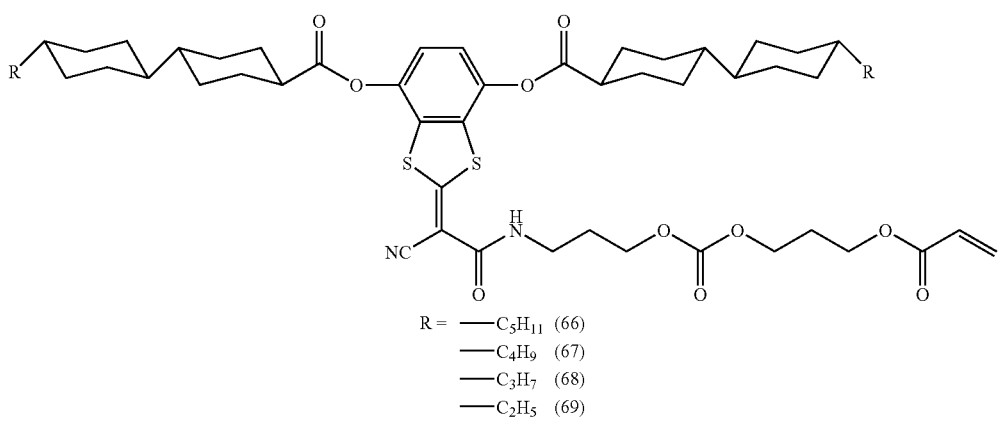
R = —C$_5$H$_{11}$ (66)
—C$_4$H$_9$ (67)
—C$_3$H$_7$ (68)
—C$_2$H$_5$ (69)

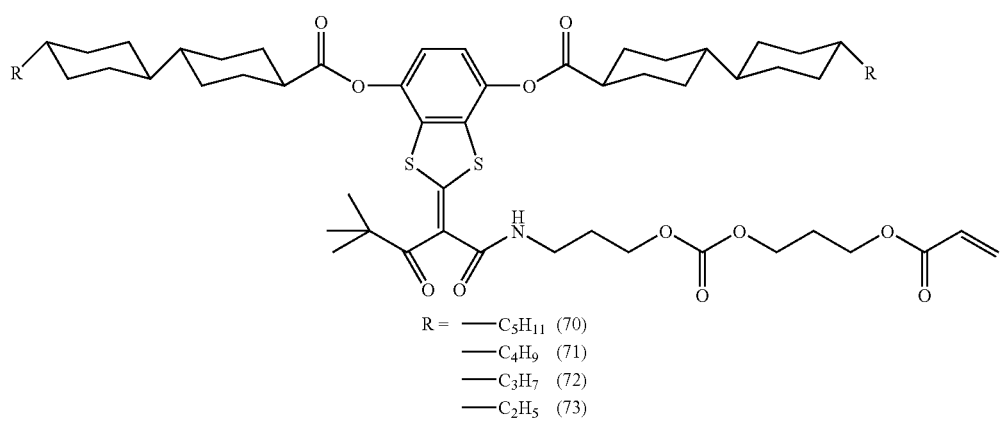
R = —C₅H₁₁ (70)
—C₄H₉ (71)
—C₃H₇ (72)
—C₂H₅ (73)
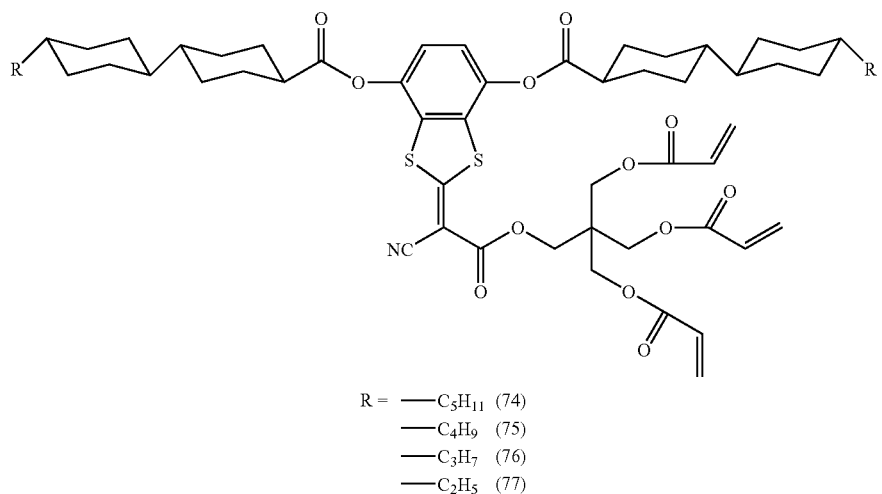
R = —C₅H₁₁ (74)
—C₄H₉ (75)
—C₃H₇ (76)
—C₂H₅ (77)
[Chemical formula 17]
(78)
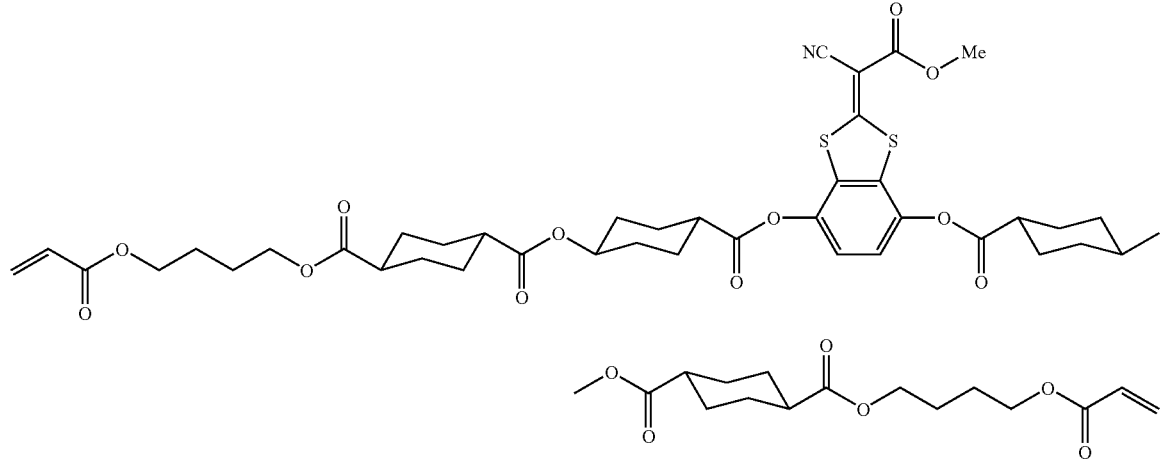

(79)
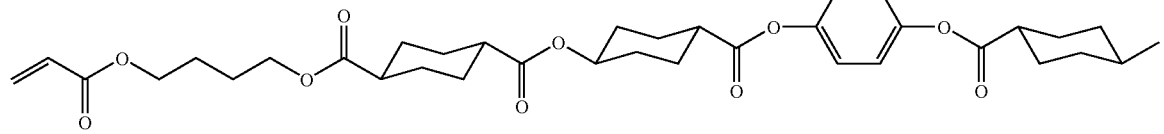
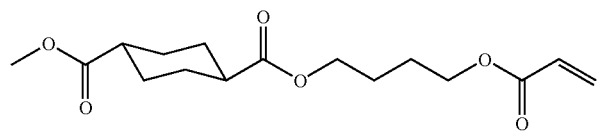
(80)
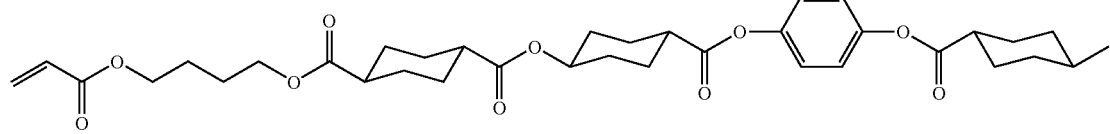
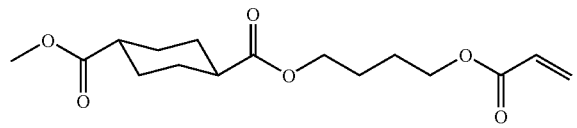
(81)
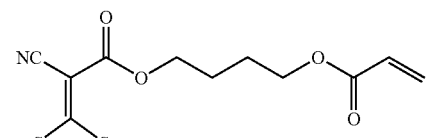
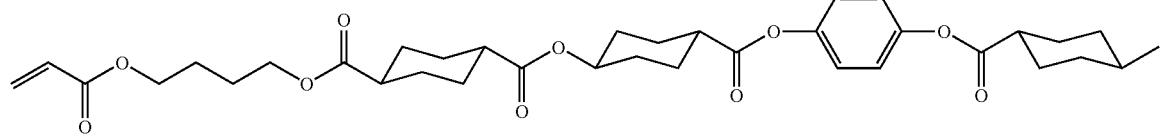
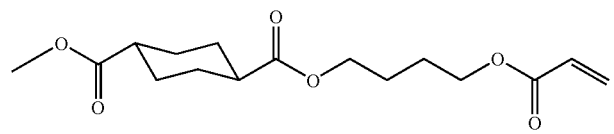

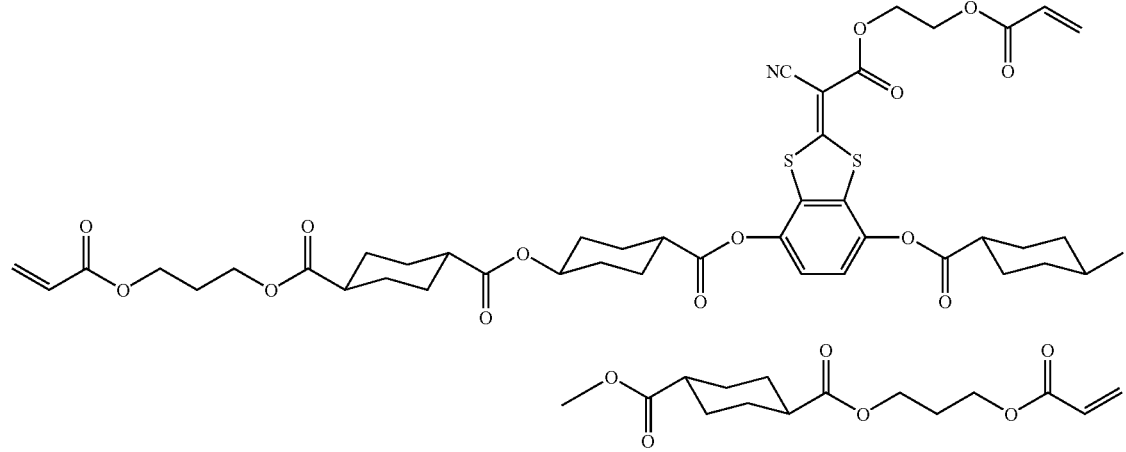
(82)
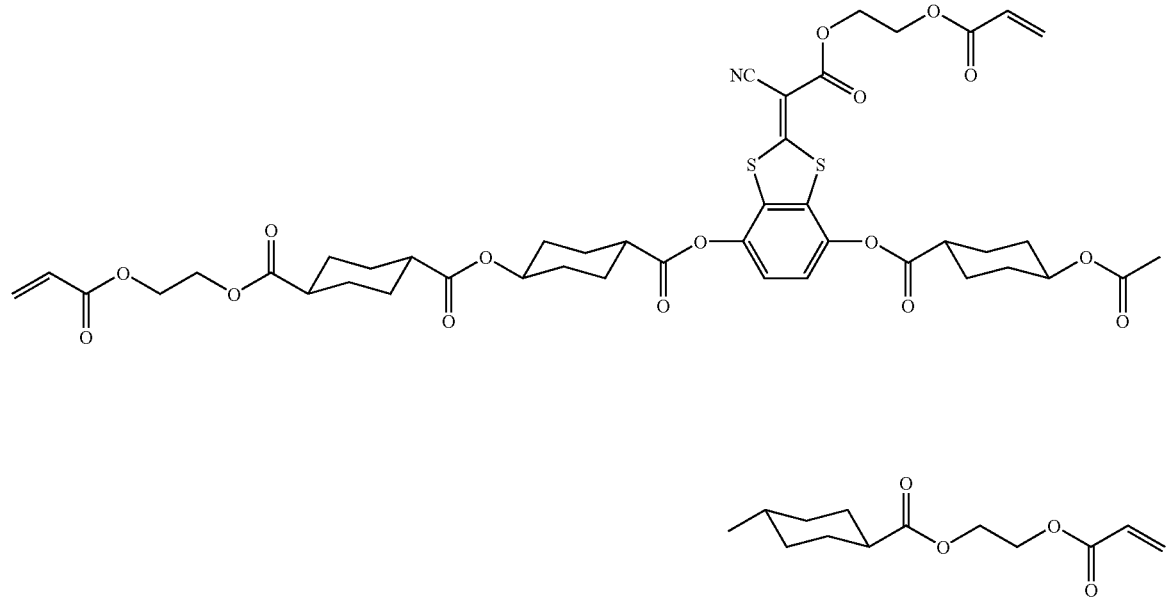
(83)
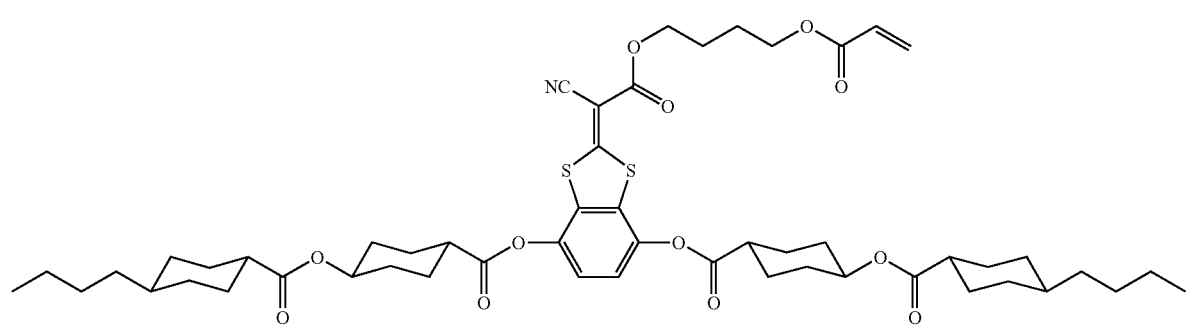
(84)

[Chemical formula 18]
(85)
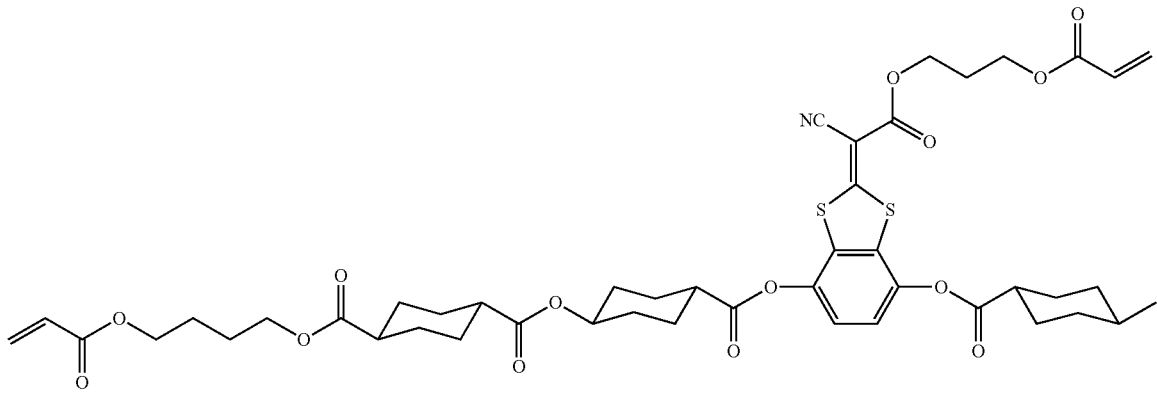
(86)
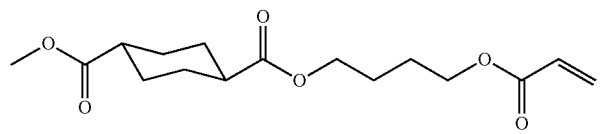
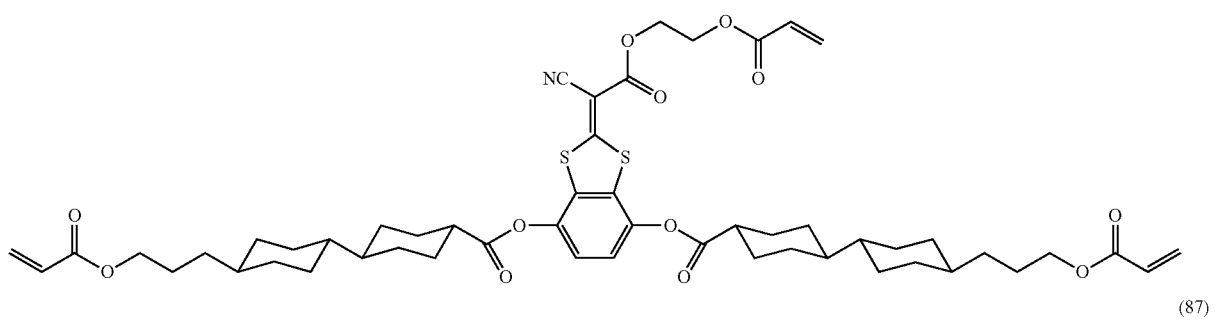
(87)
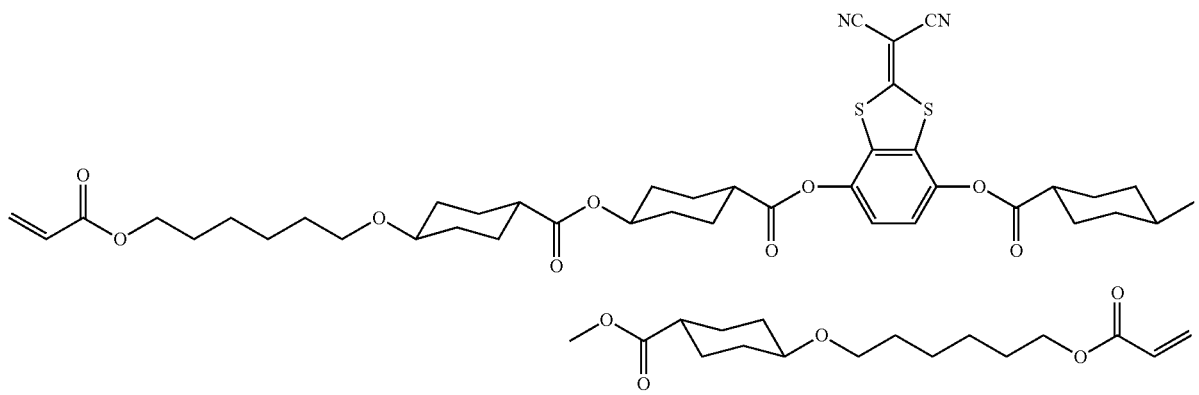
(88)
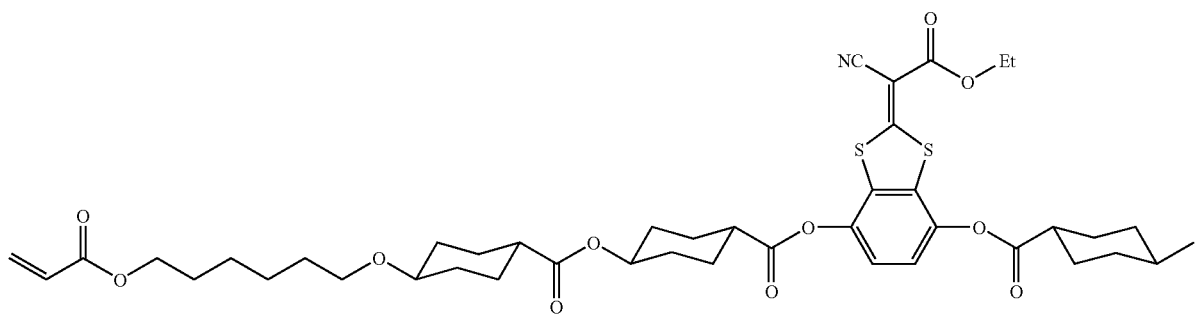

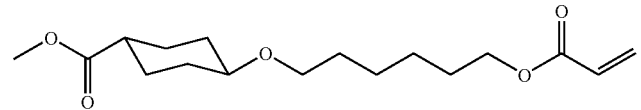
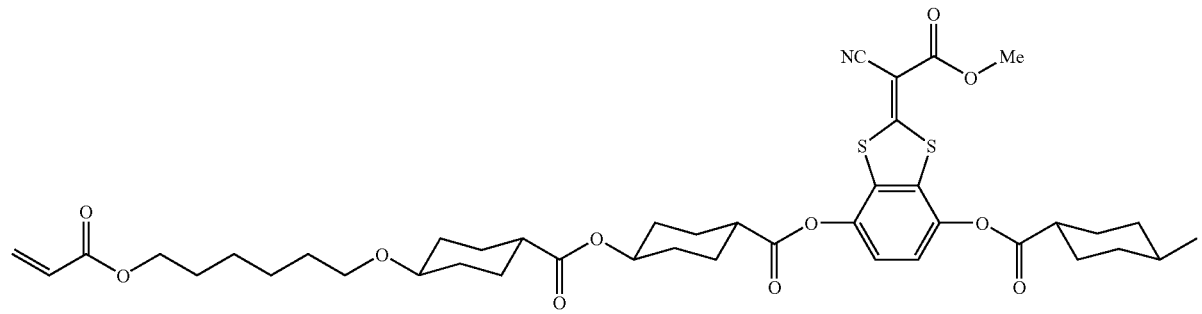
(89)
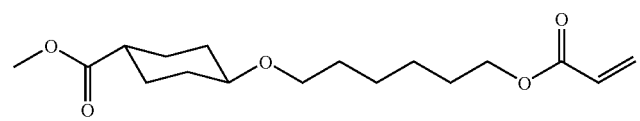
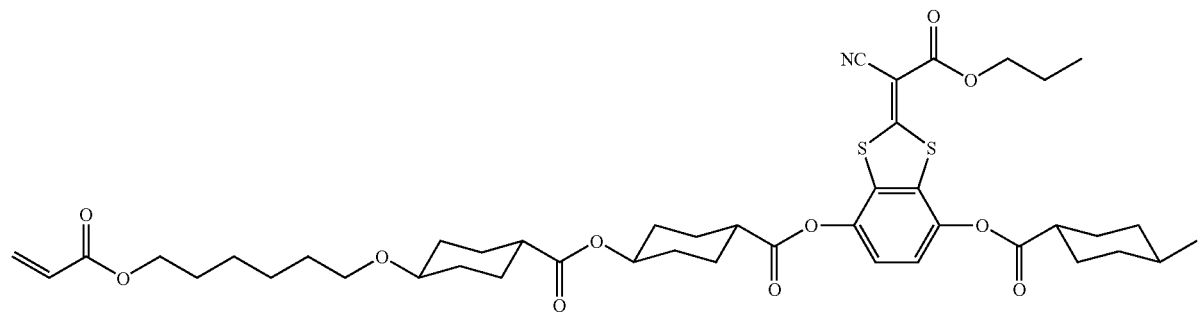
(90)
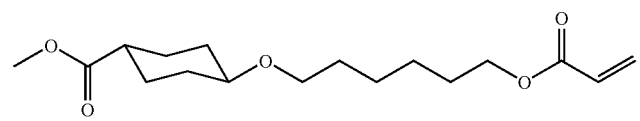

[Chemical formula 19]
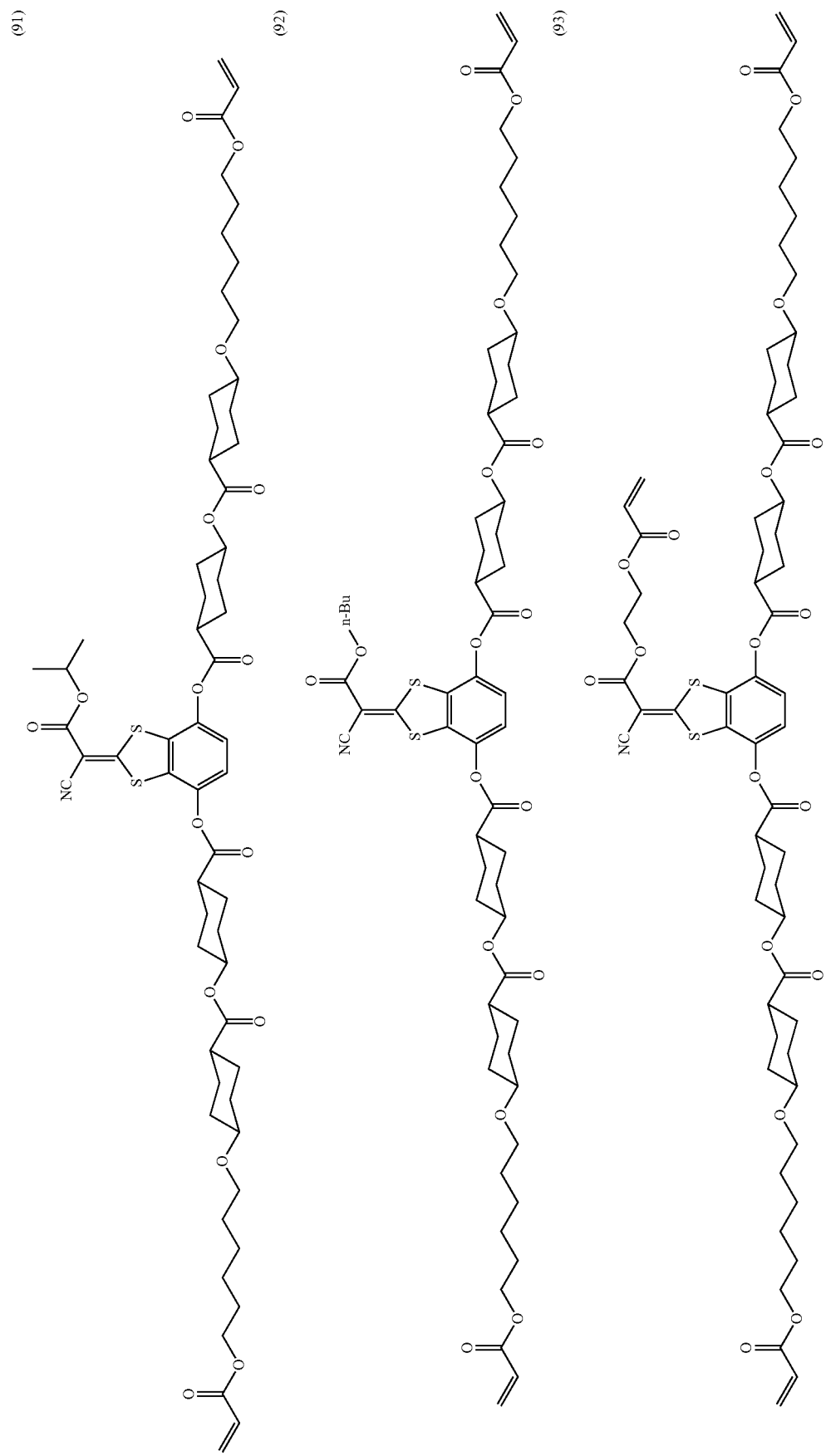

-continued
(93)
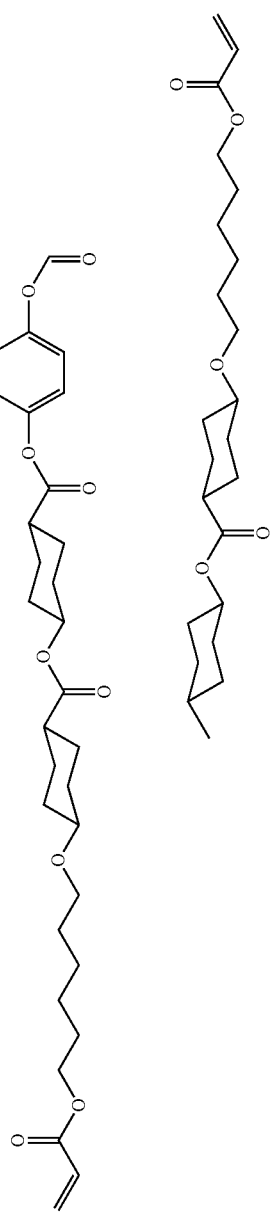
(94)
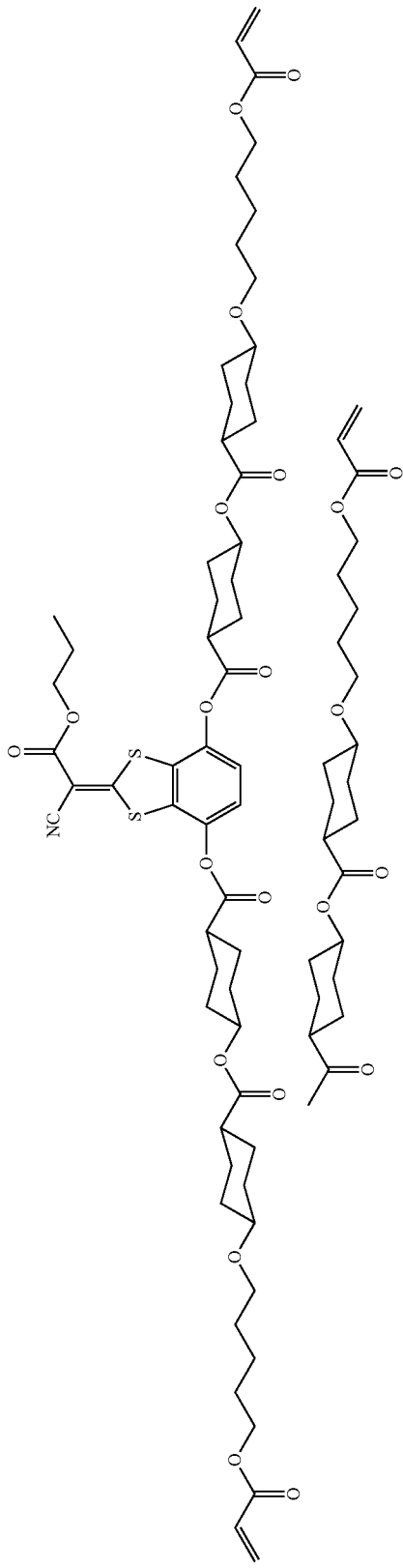

-continued
(95)
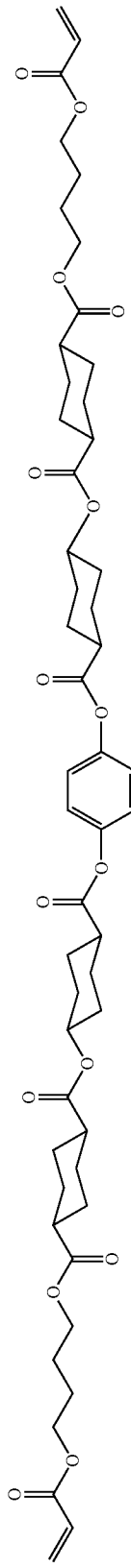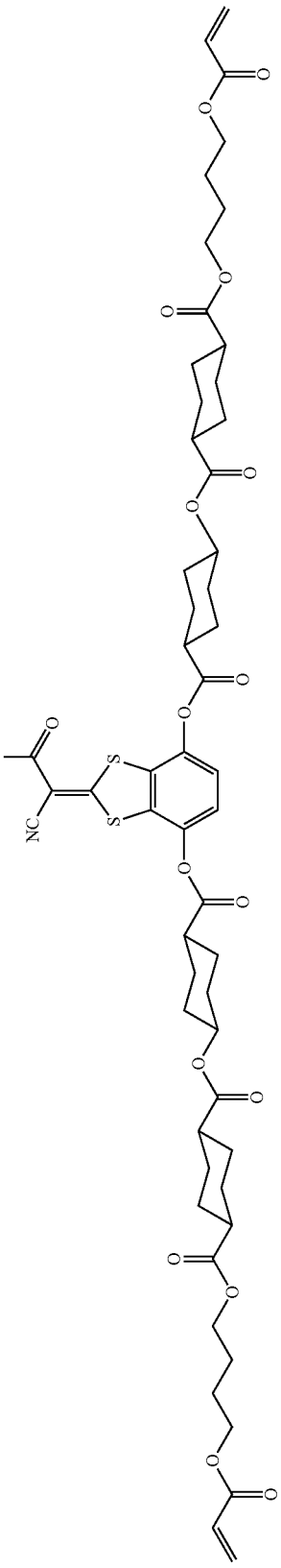

[Chemical formula 20]
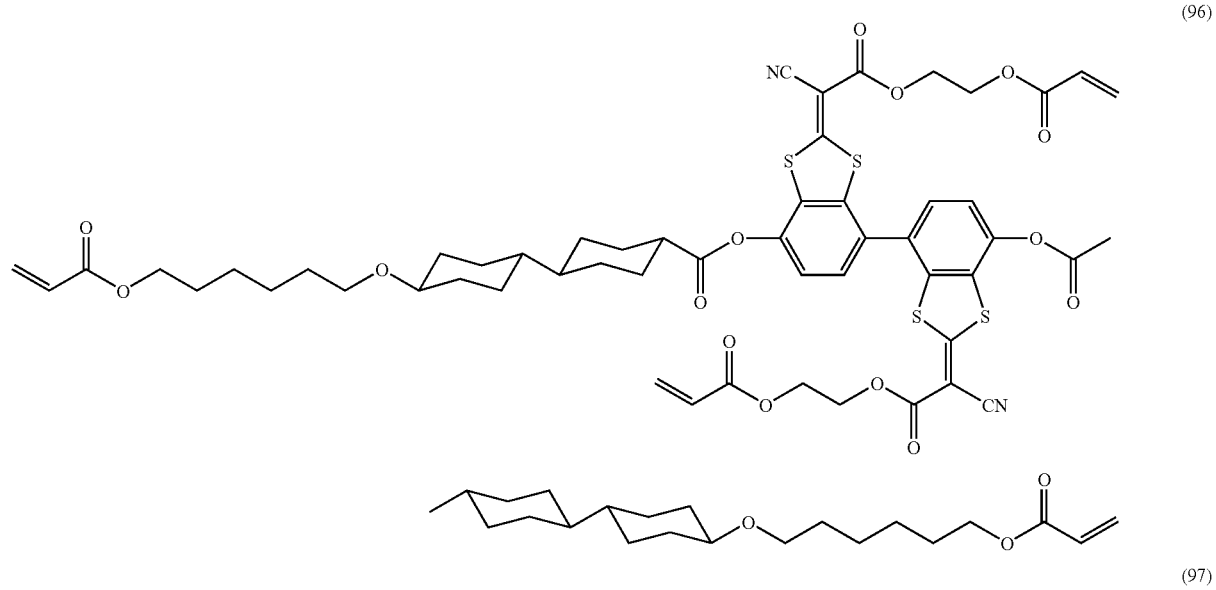
(96)
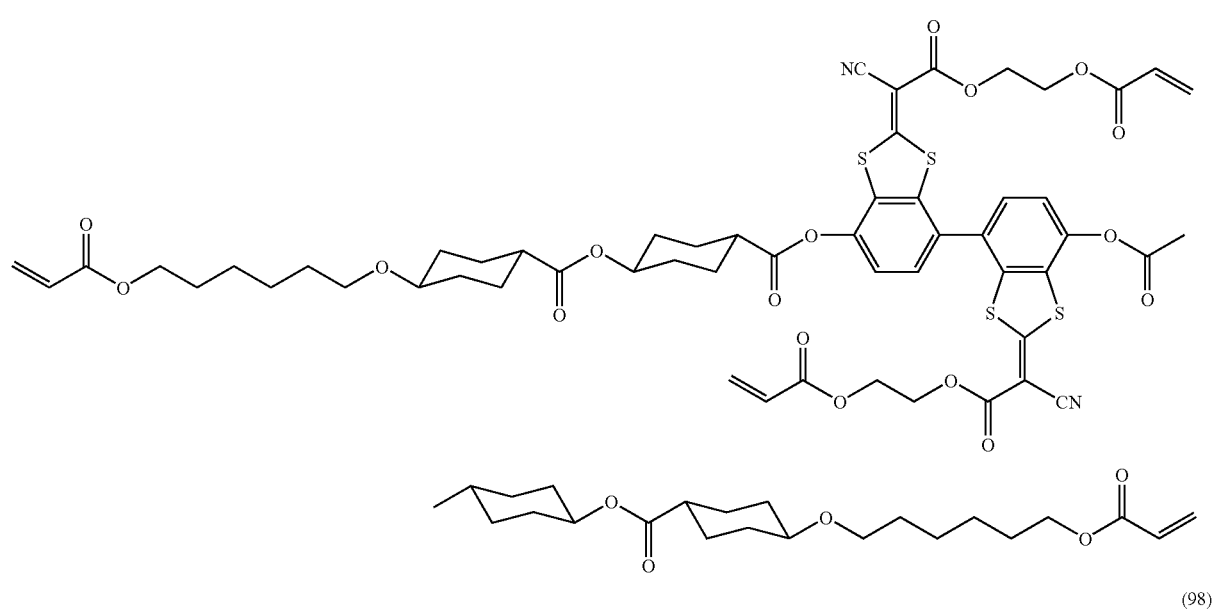
(97)
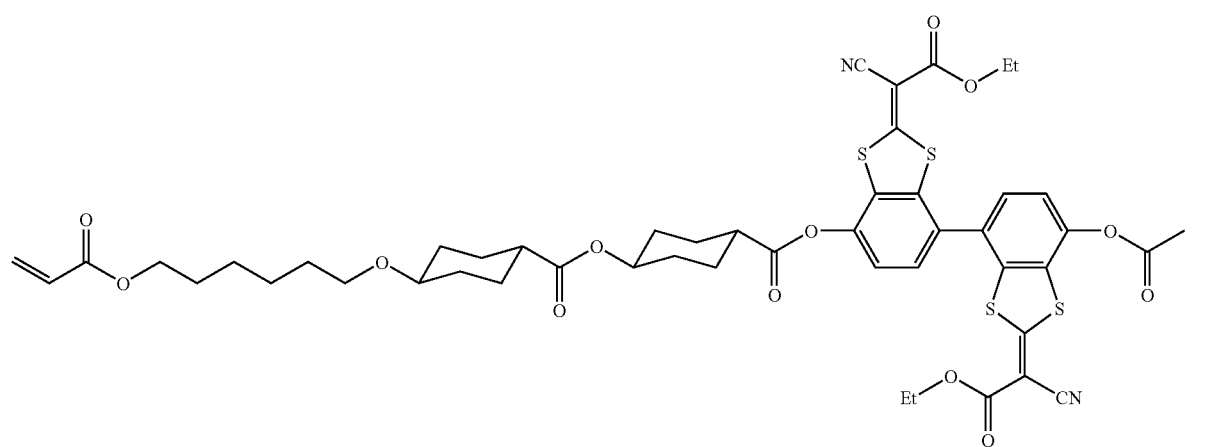
(98)

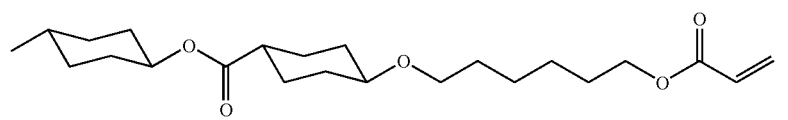
(99)
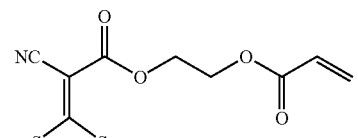
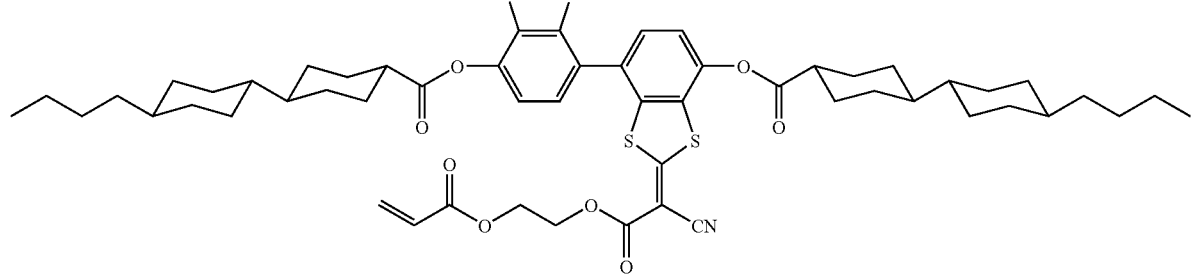
(100)
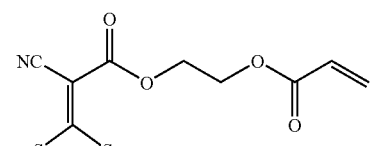
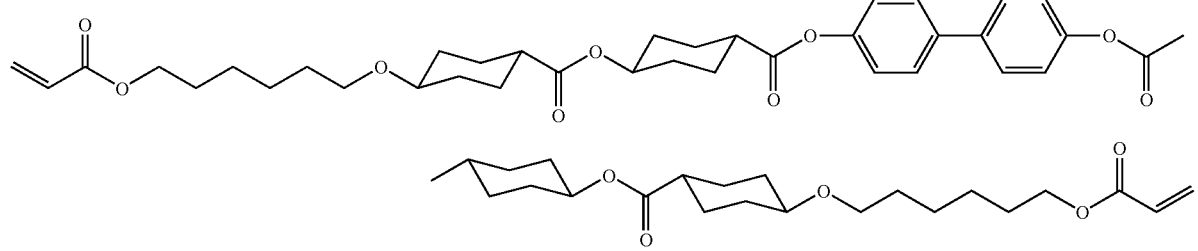
[Chemical formula 21]
(101)
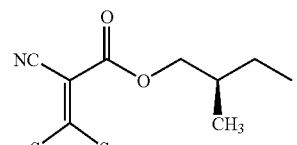
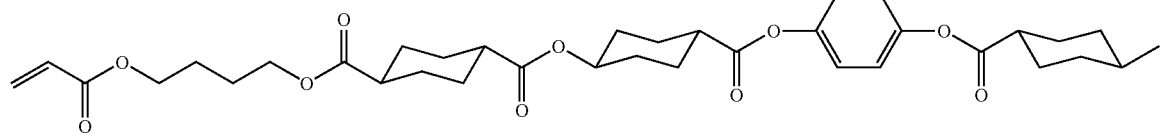
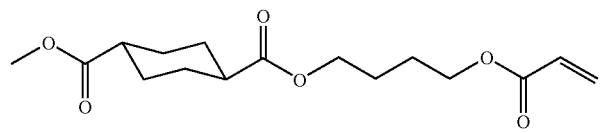

(102)
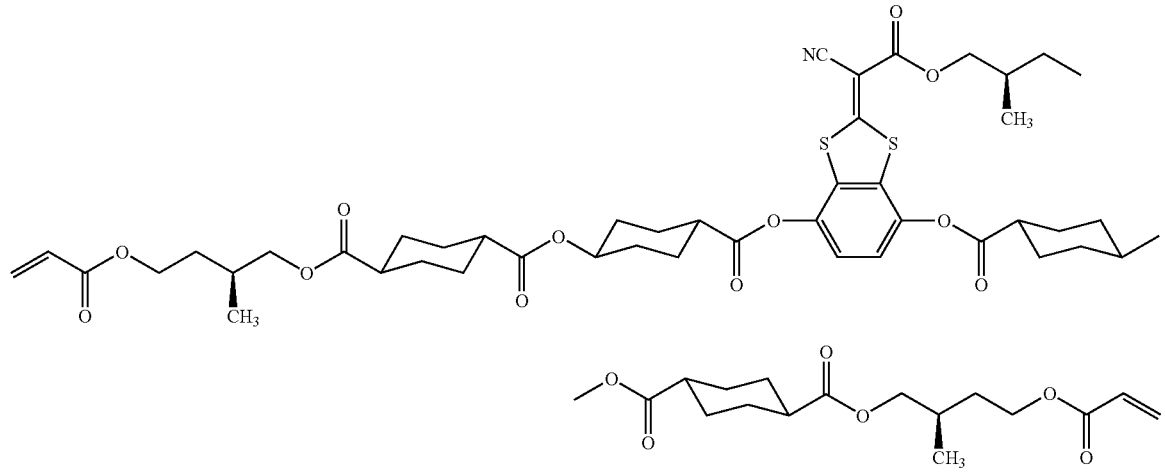
(103)
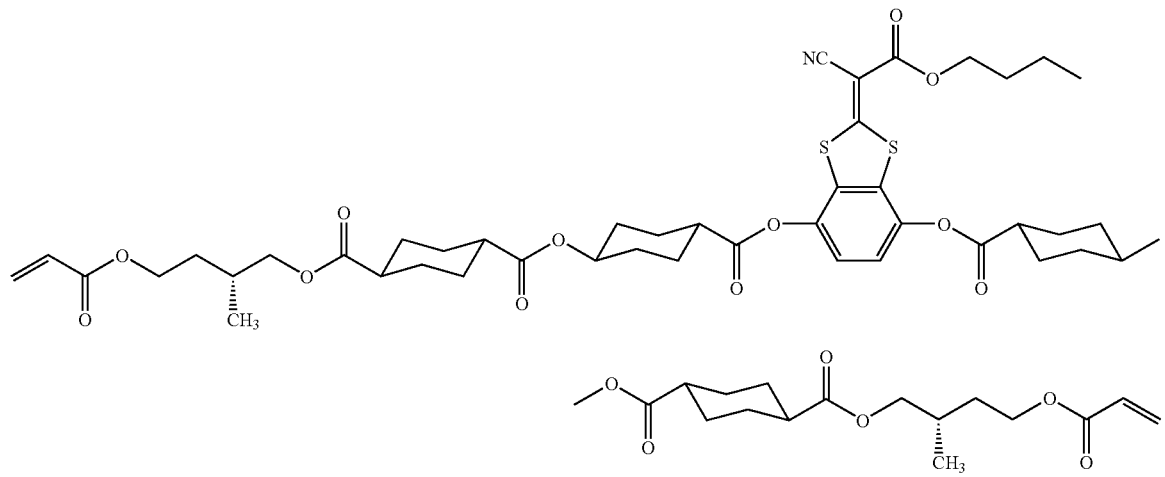
[Chemical formula 22]
(104)
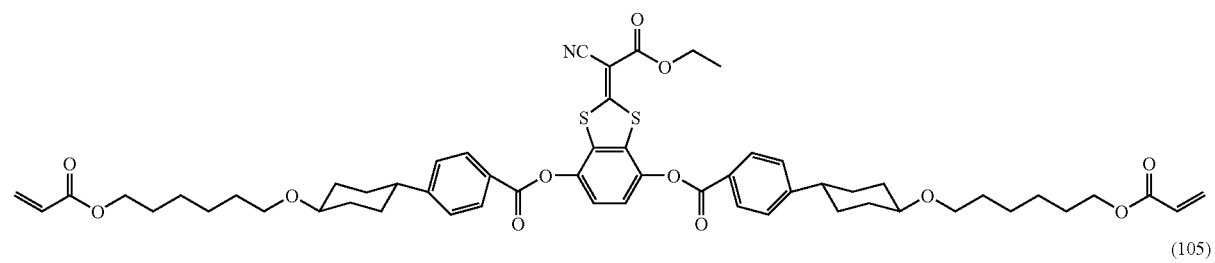
(105)
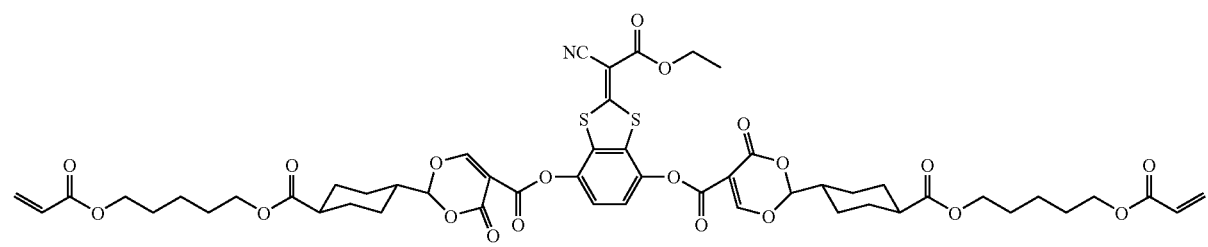

-continued
(106)
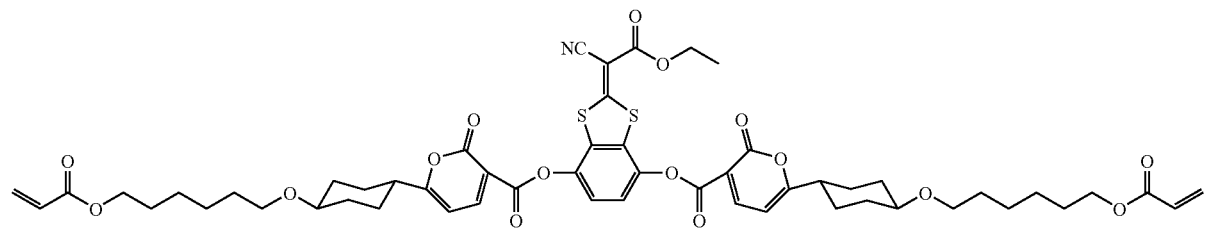
(107)
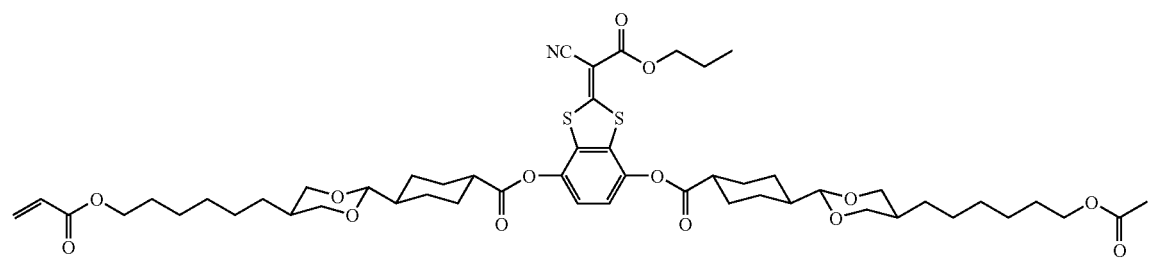
(108)
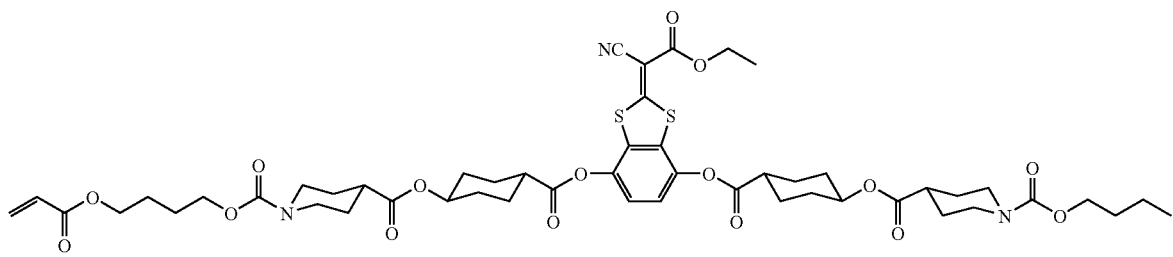
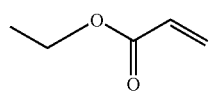
(109)
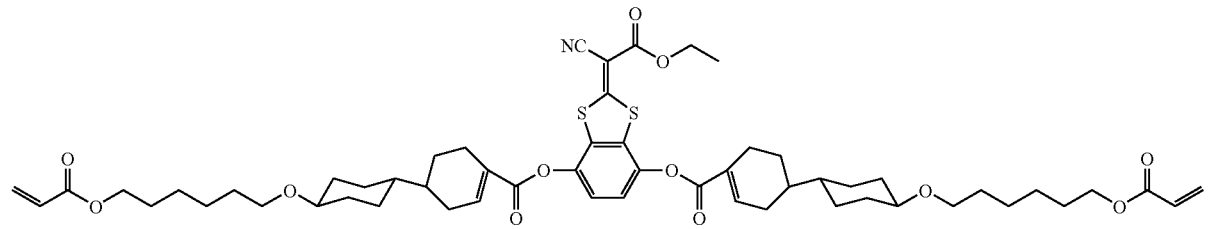

The compound represented by formula (1) or (2) can be produced, with reference to any known synthetic method. For example, the Exemplified compound (2) can be synthesized, in accordance with the following scheme:

(Birefringence)

The polymerizable liquid crystal compound represented by formula (1) or (2) of the present invention preferably has an inherent birefringence Δn of reverse wavelength dispersion, i.e. the wavelength dispersion that satisfies the relation of mathematical formula (3).

[Chemical formula 23]

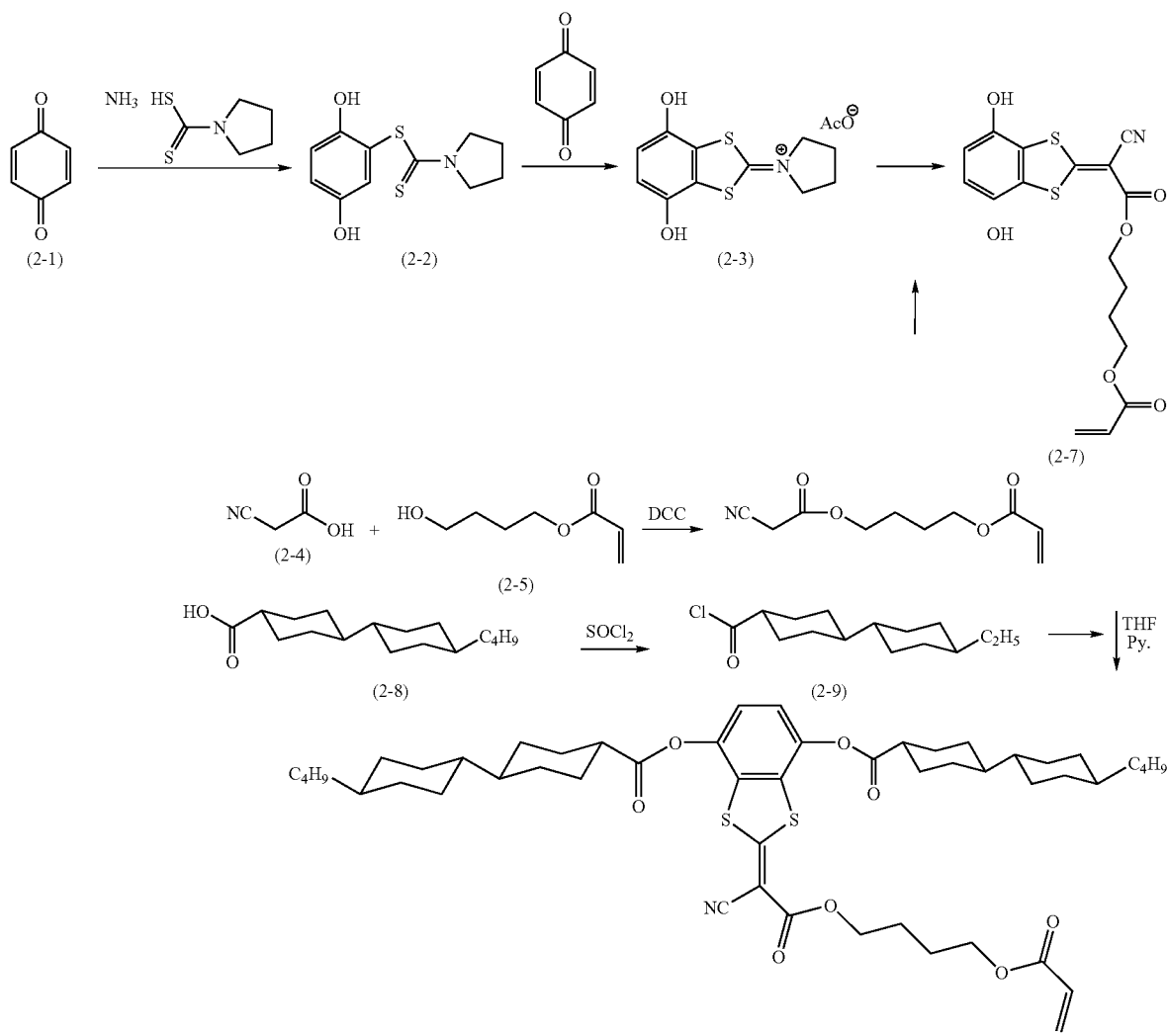

Exemplified compound (2)

In the above scheme, the synthesis of each of compounds (2-1) to (2-3) can be carried out in reference to the methods described in "Journal of Chemical Crystallography" (1997), 27(9), p. 515-526.

Further, as shown in the scheme above, the compound (2-6) is obtained by a usual esterification of the compounds (2-4) and (2-5) by using dicyclohexylcarbodiimide (DCC). The compound (2-7) is obtained, by adding a small amount of polymerization inhibitor (Irganox 1010, trade name, manufactured by Ciba Specialty Chemicals) to an N-methyl-2-pyrrolidone (NMP) suspension of the compounds (2-3) and (2-6), followed by heating the resultant mixture. It is possible to obtain the exemplified compound (2), by adding pyridine (Py), as a base, to a tetrahydrofuran (THF) solution of the compound (2-7), and further adding the compound (2-9) obtained by a usual acid chloride synthesis from compound (2-8) using thionyl chloride.

$\Delta n(450\ nm)/\Delta n(550\ nm) < 1.0$   Mathematical formula (3)

The wavelength dispersion of the liquid crystal compound of the present invention is almost independent of temperature in the same liquid crystalline phase, but, for malting the present invention more distinctive, the value in the mathematical formula (3) will be defined as a value determined at a temperature lower by 20° C. than the upper limit for the phase-change temperature. Alternatively, the value is a value determined at a temperature lower by 10° C. than the upper limit temperature of the liquid crystalline phase when the liquid crystal temperature range is 20° C. or lower, a value determined at a temperature lower by 5° C. than the upper limit temperature of the liquid crystalline phase when the liquid crystal temperature range is 10° C. or lower, and a value determined at a temperature lower by 2° C. than the upper limit temperature of the liquid crystalline phase when the liquid crystal temperature range is 5° C. or lower.

The favorable range of wavelength dispersion of Δn varies according to the application of a liquid crystal compound, and thus, may not be specified to a certain range unequivocally here, but the more favorable range of the wavelength dispersion of Δn preferably satisfies the relationships in mathematical formulae (4) and (5).

$$0.60 < \Delta n(450\ nm)/\Delta n(550\ nm) < 0.99 \quad \text{Mathematical formula (4)}$$

$$1.01 < \Delta n(650\ nm)/\Delta n(550\ nm) < 1.35 \quad \text{Mathematical formula (5)}$$

Further, considering the case where the liquid crystal compound of the present invention is used in a λ/4 plate, it is preferable to satisfy the relationships in mathematical formulae (6) and (7).

$$0.60 < \Delta n(450\ nm)/\Delta n(550\ nm) < 0.95 \quad \text{Mathematical formula (6)}$$

$$1.04 < \Delta n(650\ nm)/\Delta n(550\ nm) < 1.35 \quad \text{Mathematical formula (7)}$$

In formulae (3) to (7), Δn (450), Δn (550), and Δn (650) represent Δn's measured at 450 nm, 550 nm, and 650 nm, respectively. Each value of the measurement wavelength includes an error of ±10 nm.

The Δn of liquid crystal can be measured, for example, using a wedged liquid crystal cell described in "Liquid Crystal Handbook", 2.4.13, published by Maruzen (2000). In the manner described in the publication, the Δn at each wavelength of 450 nm, 550 nm and 650 nm is determined through three kinds of band-pass-filters.

If a liquid crystal compound has a polymerizable group as defined in the present invention, the liquid crystal compound sometimes polymerizes in the wedged liquid crystal cell, thereby to tend to disturb the measurement. In that case, it is preferred to incorporate a polymerization inhibitor, for the measurement. Further, the Δn can be also determined in another manner. First, the molecules of the liquid crystal compound are evenly aligned, and then the phase retardation is measured by means of, for example, KOBRA (manufactured by OJI SCIENTIFIC INSTRUMENTS CO., LTD.) to obtain Re at the respective wavelength. Independently, the thickness of the layer of the aligned molecules is measured, and then the Δn is calculated according to the formula: Δn=Re/d (d: thickness of the layer).

The liquid crystal compound of the present invention may have either positive or negative birefringence, but preferably has positive birefringence.

Liquid crystal phases having positive birefringence are described in detail, for example, in Chapter 2 in "Liquid Crystal Handbook", published by Maruzen (2000). Examples thereof include nematic phase, cholesteric phase, and smectic phase (e.g., smectic A phase, smectic C phase).

When used for an optically anisotropic layer, the liquid crystal compound of the present invention preferably forms such a favorable mono-domain phase that the molecules of the compound can be oriented in even alignment without any defect. If not, a poly-domain structure having plural domains is formed and hence defects in orientation, which scatter light, are formed on the borders among the domains, and consequently the thus-obtained optically anisotropic layer has poor transparence. The liquid crystal compound of the present invention, therefore, preferably forms nematic phase (N phase) or smectic A phase (SA phase), for ensuring the mono-domain structure. It is particularly preferred to form nematic phase.

The liquid crystal compound may be either a compound of low molecular weight or a polymer, but preferably a compound of low molecular weight because low-molecular weight liquid crystalline molecules are easily aligned.

(Preparation of Film with Reverse Wavelength Dispersion)

It is possible to prepare a film with reverse wavelength dispersion, by applying a polymerizable liquid crystal compound represented by formula (1) or (2) of the present invention on an oriented film, followed by orienting and then immobilizing the resultant compound. For example, when the liquid crystal compound of the present invention is oriented almost in the horizontal direction on the oriented film (so-called A plate), the retardation values Re(550 nm) in the orientation direction (hereinafter, referred to as TD direction) and in the direction perpendicular thereto (hereinafter, referred to as MD direction) each are positive, and the retardation Re at a particular wavelength satisfies the relationships in mathematical formulae (8) and (9).

$$0.5 < Re(450\ nm)/Re(550\ nm) < 1.0 \quad \text{Mathematical formula (8)}$$

$$1.05 < Re(650\ nm)/Re(550\ nm) < 1.5 \quad \text{Mathematical formula (9)}$$

In preparing the film that satisfies the relationships in mathematical formulae (8) and (9), it is necessary to adjust the absorption wavelength and the direction of transition moment of the film in the TD direction and the MD direction properly. Here, typical three colors are defined to be blue (450 nm), green (550 nm), and red (650 nm), respectively. It is necessary to adjust retardation, preferably to the optimum, at each wavelength, for improving view angle characteristics. In the present invention, when positive birefringence is applied to the most important green (550 nm), the preferable ranges of the blue (450 nm) and red (650 nm) are within the ranges as specified in mathematical formulae (8) and (9).

Because Re is proportional to the retardation between in the TD and MD directions, i.e., a difference (Δn) of the refractive index in the TD direction subtracted by the refractive index in the MD direction, when the wavelength dispersion of the refractive index in the MD direction is declining more steeply than the wavelength dispersion of the refractive index in the TD direction (in the case of the slope of Δn when the wavelength is shorter in the left and longer in the right), the difference satisfies the relationships in mathematical formulae (10) and (11).

$$1 > |\Delta n(450\ nm)/\Delta n(550\ nm)| \quad \text{Mathematical formula (10)}$$

$$1 < |\Delta n(650\ nm)/\Delta n(550\ nm)| \quad \text{Mathematical formula (11)}$$

The wavelength dispersion of the refractive index is, as represented by the Lorentz-Lorenz expression, closely related to the absorption of a substance. Thus, for allowing the wavelength dispersion in the MD direction to tend downward (declining), it is necessary to make the absorption transition wavelength in the MD direction be shifted to a longer wavelength region than one in the TD direction, and this allows to design a film that satisfies the relationships in mathematical formulae (8) and (9). For instance, in a polymer material subjected to a stretching treatment, the MD direction thereof is perpendicular to a molecular chain. Shifting the absorption transition wavelength in the transverse direction of the polymer to a longer wavelength region is very difficult, by modifying or designing a particular polymer material.

When the liquid crystal compound of the present invention is oriented almost in the vertical orientation (so-called C plate), the retardation Rth (550 nm) in the thickness direction is negative and the retardation Rth at a particular wavelength satisfies the relationships in mathematical formulae (12) and (13).

$$0.6 < Rth(450\ nm)/Rth(550\ nm) < 0.99 \quad \text{Mathematical formula (12)}$$

$$1.01 < Rth(650\ nm)/Rth(550\ nm) < 1.35 \quad \text{Mathematical formula (13)}$$

In preparing the film that satisfies the relationships in mathematical formulae (12) and (13), it is necessary to adjust the absorption wavelength and the direction of transition moment of the film in the in-plane direction and thickness direction properly. Here, typical three colors are defined to be blue (450 nm), green (550 nm), and red (650 nm), respectively. It is necessary to adjust retardation, preferably to the optimum, at each wavelength, for improving view angle characteristics. In the present invention, when positive birefringence is applied to the most important green (550 nm), the preferable ranges of the blue (450 nm) and red (650 nm) are within the ranges as specified in mathematical formulae (12) and (13).

It is possible to prepare a film in which the retardation Rth(550 nm) in the thickness direction is negative and satisfies the relationships in mathematical formulae (12) and (13), by making the refractive index in the thickness direction larger than the refractive index in the in-plane direction and making the absorption transition wavelength in the in-plane direction longer than that in the thickness direction. However, for example, when a polymer material is used, the molecular chains are aligned in the in-plane direction, and it is relatively easier to make the absorption transition wavelength in the in-plane direction longer than that in the thickness direction, but it is very difficult to make the refractive index in the thickness direction larger than the refractive index in the in-plane direction, and thus further difficult to satisfy both of these two conditions simultaneously.

When the liquid crystal compound of the present invention is oriented almost helically and the helical axis is almost vertical to the substrate, the retardation Rth(550 nm) in the thickness direction is positive and the retardation Rth at a particular wavelength satisfies the relationships in mathematical formulae (14) and (15).

$$0.6 < Rth(450\ nm)/Rth(550\ nm) < 0.99 \quad \text{Mathematical formula (14)}$$

$$1.0 < Rth(650\ nm)/Rth(550\ nm) < 1.35 \quad \text{Mathematical formula (15)}$$

In preparing the film that satisfies the relationships in mathematical formulae (14) and (15), it is necessary to adjust the absorption wavelength and the direction of transition moment of the film in the in-plane direction and thickness direction properly.

It is possible to prepare a film in which the retardation Rth(550 nm) in the thickness direction is positive and satisfies the relationships in mathematical formulae (14) and (15), by making the refractive index in the in-plane direction larger than the refractive index in the thickness direction and making the absorption transition wavelength in the thickness direction longer than that in the in-plane direction. However, for example, when a polymer material is used, the molecular chains are aligned in the in-plane direction, and it is relatively easier to make the refractive index in the in-plane direction larger than the refractive index in the thickness direction, but it is very difficult to make the absorption transition wavelength in the thickness direction longer than that in the in-plane direction, and thus further difficult to satisfy both of these two conditions simultaneously.

As described above, by using the method of orienting and then immobilizing the liquid crystal compound of the present invention, it is possible to prepare a film which was very difficult to obtain via the conventional technique by using a polymer material, i.e.

1) a film having a positive retardation, in which the dispersion of the positive retardation is reverse wavelength dispersion, in the film in-plane direction;

2) a film having a negative retardation, in which the dispersion of the negative retardation is reverse wavelength dispersion, in the film thickness direction; or 3) a film having a positive retardation, in which the dispersion of the positive retardation is reverse wavelength dispersion, in the film thickness direction.

[Liquid Crystal Composition]

In addition to the polymerizable liquid crystal compound represented by formula (1) or (2) of the present invention, the liquid crystal composition of the present invention may contain any other additive(s) in combination. Examples of the additives include liquid crystal compounds other than the compounds represented by formula (1) or (2), and the below-described air interface orientation-controlling agent, repulsion inhibitor, polymerization initiator, polymerizable monomer, and others.

(Liquid Crystal Compound)

The liquid crystal composition of the present invention contains the compound represented by formula (1) or (2). When the liquid crystal composition of the present invention is used in a retardation sheet, it is preferred to form such a mono-domain phase that the molecules of the compound can be oriented in even alignment without any defect. If not, a poly-domain structure having plural domains is formed and hence orientation defects, which scatter light, are formed on the borders among the domains, and consequently the thus-obtained retardation sheet has poor transparence. The liquid crystal composition of the present invention, therefore, preferably forms nematic phase (N phase), for ensuring the mono-domain structure.

Further, when the liquid crystal composition of the present invention is used in a retardation sheet, it is preferred to form a liquid crystal phase preferably in the liquid crystal temperature range of 10 to 250° C., more preferably in the range of 10 to 150° C., in consideration of productivity of the retardation sheet. If the temperature range is too low, a cooling procedure for lowering the temperature to a temperature range giving liquid crystal phase may be required. If the temperature range is too high, the composition must be heated higher than the temperature giving a liquid crystal phase so that the composition may be once in isotropic liquid state, thus thermal energy is wasted and the substrate may deform or deteriorate thermally.

In the liquid crystal composition of the present invention, the liquid crystal compound may be used singly or in combination. For example, a polymerizable liquid crystal compound and a non-polymerizable liquid crystal compound can be used in combination. It is also possible to use a liquid crystal compound of low molecular weight and a liquid crystal compound of high molecular weight in combination. Further, two liquid crystal compounds that satisfies the relationship in mathematical formula (3) may be used in combination.

Examples of the liquid crystal compounds other than the compounds represented by formula (1) or (2) include the liquid crystal compounds described, for example, in JP-A-2005-289980.

The liquid crystal compound of the present invention that satisfies the relationship in mathematical formula (3) may be mixed with a liquid crystal compound giving normal wavelength dispersion of Δn. Here, "normal wavelength dispersion" means that the Δn satisfies the relationship as represented by mathematical formula (16).

$$\Delta n(450\ nm)/\Delta n(550\ nm) > 1.0 \qquad \text{Mathematical formula (16)}$$

By mixing the liquid crystal compound of the present invention satisfying the relationship in mathematical formula (3) with a liquid crystal compound having a normal wavelength dispersion of Δn, it is possible to prepare a liquid crystal composition having wavelength dispersion in an intermediate state between those. Specifically, with the conventional liquid crystal compounds, the relationship in mathematical formula (17) has been very difficult to attain. However, it is possible to prepare a liquid crystal composition having a wavelength dispersion in the region represented by mathematical formula (17) in a easier manner, by mixing the liquid crystal compound of the present invention satisfying mathematical formula (3) above with a liquid crystal compound having a normal wavelength dispersion of Δn.

$$1.0 \leq \Delta n(450\ nm)/\Delta n(550\ nm) < 1.1 \qquad \text{Mathematical formula (17)}$$

Since exhibiting liquid crystallinity, the liquid crystal compound of the present invention that satisfies the relation in mathematical formula (3) is highly-possibly mixable in any mixing ratio with a liquid crystal compound giving normal wavelength dispersion of Δn. Thus, it is possible to adjust the mixing ratio so that the target wavelength dispersion can be obtained.

The content of the polymerizable liquid crystal compound represented by formula (1) or (2) in the liquid crystal composition is preferably 10 to 100 mass %, more preferably 40 to 100 mass %. The content of the liquid crystal compound in the liquid crystal composition of the present invention is not particularly limited, as long as the composition shows liquid crystallinity, but preferably 30 to 90 mass %, more preferably 50 to 90 mass %, in the liquid crystal composition.
(Air-Interface Orientation (Alignment) Controlling Agent)

Liquid crystal compounds are known to have different tilt angles (inclination angles) at the air interface, according to the kinds of compounds. The tilt angle at the air interface should be controlled arbitrarily, according to the optical application of the retardation sheet. The tilt angle can be controlled, for example, by an external field, such as an electric field or a magnetic field, or an additive, and the use of an additive is preferable. Such an additive is preferably a compound having a substituted or non-substituted aliphatic group with 6 to 40 carbon atoms, or a substituted or non-substituted aliphatic-group-substituted oligosiloxanoxy group with 6 to 40 carbon atoms, by one or more units within its molecule, and more preferably a compound having such a group by two or more units within its molecule. For example, the compounds described in JP-A-11-352328 and JP-A-2002-20363 may be used as the air interface orientation-controlling agents. Further, the compounds described in JP-A-2002-129162 can also be used. The matters described in JP-A-2004-53981, paragraph numbers [0072] to [0075], can also be applied to the present invention appropriately. Further, it is possible to improve coatability and prevent occurrence of surface irregularity or repellency, by addition of any of those compounds. The compounds described in JP-A-2006-106662 may be used in combination, as the vertical orientation agent.

The additive for controlling orientation at the air interface is preferably employed in an amount of 0.001 to 20 mass %, more preferably 0.01 to 10 mass %, and most preferably 0.1 to 5 mass %, with respect to the liquid crystal composition.
(Anti-Repelling Agent)

In general, in order to prevent repelling of the liquid crystal composition in coating, a polymer material is preferably added to the composition, in addition to the liquid crystal compound to be used. There is no particular restriction on the polymer to be used, as long as it does not give unfavorable effects to the orientation or change in the inclined angle of the liquid crystal compound. JP-A-8-95030 describes examples of the polymer material. Among them, cellulose esters are particularly preferred. Examples of the cellulose esters include cellulose acetate, cellulose acetate propionate, hydroxypropyl cellulose, and cellulose acetate butyrate.

The polymer material for preventing repelling is added in an amount of preferably 0.1 to 10 mass %, more preferably 0.1 to 8 mass %, and filter preferably 0.1 to 5 mass %, based on the amount of the liquid crystal compound, so as not to hinder the orientation of the liquid crystal.
(Polymerization Initiator)

In the present invention, molecules of the liquid crystal compound are preferably oriented and immobilized in monodomain alignment. Namely, the molecules are preferably aligned essentially evenly and immobilized with the even alignment kept. Thus, the polymerizable liquid crystal compound of the present invention is preferably immobilized in monodomain orientation by a polymerization reaction.

The polymerization reaction may be a thermal polymerization reaction caused by a thermal polymerization initiator, a photo-polymerization reaction caused by a photo polymerization initiator, or a polymerization reaction caused by irradiation of electron beam. The photo-polymerization reaction or electron beam-polymerization reaction is preferred for fear that the support or other parts may thermally deform or deteriorate during the thermal polymerization reaction.

Examples of the photopolymerization initiator include α-carbonyl compounds (described in U.S. Pat. Nos. 2,367,661 and 2,367,670), acyloin ethers (described in U.S. Pat. No. 2,448,828), α-hydrocarbon-substituted aromatic acyloin compounds (described in U.S. Pat. No. 2,722,512), polynuclear quinone compounds (described in U.S. Pat. Nos. 3,046,127 and 2,951,758), combinations of a triarylimidazole dimer with p-aminophenyl ketone (described in U.S. Pat. No. 3,549,367), acridine and phenazine compounds (described in JP-A-60-105667 and U.S. Pat. No. 4,239,850), and oxadiazol compounds (described in U.S. Pat. No. 4,212,970).

It is preferable to use the photopolymerization initiator in an amount of from 0.01 to 20 mass %, more preferably from 0.5 to 5 mass %, based on the solid matters in the coating solution.

In the photoirradiation for polymerizing the liquid crystal molecules, it is preferable to use ultraviolet ray. The irradiation energy is preferably from 10 mJ/cm$^2$ to 50 J/cm$^2$, more preferably from 50 to 800 mJ/cm$^2$. To accelerate the photopolymerization reaction, the photoirradiation may be carried out under heating.

Because the oxygen concentration of atmosphere exerts influence on the polymerization degree, if it is not possible to obtain desirable polymerization degree in the air, it is preferable to reduce the oxygen concentration by a method such as nitrogen substitution. The oxygen concentration is preferably 10% or less, more preferably 7% or less, and most preferably 3% or less.
(Polymerizable Monomer)

To the liquid crystal composition, a polymerizable monomer may be added. There is no particular restriction on the polymerizable monomer usable with the liquid crystal compound, as long as it is compatible with the liquid crystal compound and it neither cause conspicuous change of the inclined angle nor disturbing of the orientation of the liquid crystal molecules. Preferred are compounds having polymerizable ethylenically unsaturated groups, such as a vinyl group, a vinyloxy group, an acryloyl group, and a methacryloyl group.

An addition amount of the polymerizable monomer is generally in the range of from 0.5 to 50 mass %, and preferably from 1 to 30 mass %, based on the liquid crystal compound. Particularly preferred is a monomer having two or more reactive functional groups, because adhesion between the aligned or oriented layer and the optically anisotropic layer can be improved.

(Chiral Agent)

In the present invention, it is possible to bring the liquid crystal composition into the cholesteric phase, by adding at least one chiral agent thereto. Any one of known chiral agents (e.g., those described in, edited by Japan Society for the Promotion of Science the 142nd Committee, "Liquid Crystal Device Handbook", Chapter 3, Section 4-3, Chiral Agents for TN and STN, p. 199, 1989) may be used as the chiral agent for use in the present invention.

Chiral agents generally contain an asymmetric carbon atom(s), but axial- or planer-asymmetry compounds containing no asymmetric carbon atom may also be used as the chiral agents. Examples of the axial- or planer-asymmetry compounds include binaphtyl, helicenes, paracyclofan, and the derivatives thereof. The chiral agent may have the liquid crystallinity, and thus, the liquid crystal compound of the present invention may be the chiral agent.

The usage amount of the chiral agent is preferably 0.001 to 200 mol %, to the amount of the liquid crystal compound. The lower amount of the chiral agent is preferable, for reduction of affection on liquid crystallinity. Thus, the chiral agent preferably has a higher torsional force. Examples of the chiral agents having higher torsional force include those described in JP-A-2003-287623.

The negative C plate film obtained by orienting and immobilizing the compound of the present invention in the cholesteric orientation state, can be used as the negative C plate needed for the view angle-adjustable liquid crystal display device described in IDW'06 (LCTp3-31L).

(Coating Solvent)

As the solvent that can be used in preparing the liquid crystal composition, it is preferable to use an organic solvent. Examples of the organic solvent include amides (for example, N,N-dimethylfoimamide), sulfoxides (for example, dimethyl sulfoxide), heterocyclic compounds (for example, pyridine), hydrocarbons (for example, toluene, and hexane), alkyl halides (for example, chloroform, and dichloromethane), esters (for example, methyl acetate, and butyl acetate), ketones (for example, acetone, methyl ethyl ketone, methyl isobutyl ketone, and cyclohexanone), and ethers (for example, tetrahydrofuran, and 1,2-dimethoxyethane). Among these, alkyl halides, esters, and ketones are preferred. It is also possible to use two or more organic solvents in combination.

[Retardation Sheet (Retardation Plate or Phase Retarder)]

The retardation sheet of the present invention has, on a transparent substrate, an oriented film, and at least one optically anisotropic layer containing the compound represented by formula (1) or (2). It is possible to obtain the retardation sheet of the present invention via formation of the optically anisotropic layer, by once heating the liquid crystal composition containing the compound represented by formula (1) or (2) to its liquid crystal phase-forming temperature, and then cooling it while preserving the orientation state, to immobilize the liquid crystal composition without damage on the oriented state of the liquid crystal. Alternatively, the optically anisotropic layer may be formed, by heating the liquid crystal composition to which the polymerizable group-containing liquid crystal compound and a polymerization initiator are added, to its liquid crystal phase-forming temperature, allowing polymerization, and then cooling the resultant polymer. Herein, the "immobilized" state as used in the present invention is typically and most favorably, but not limited to, a state in which the orientation of the liquid crystal compound contained in the optically anisotropic layer is preserved; and specifically the term means a state retaining the immobilized orientation state stably without fluidization of the optically anisotropic layer or without change in the orientation state by external field or force, in a temperature range generally of 0° C. to 50° C., more severely of −30° C. to 70° C.

In the retardation sheet of the present invention, the liquid crystal compound may not have liquid crystallinity any more, if the optically anisotropic layer retains its optical anisotropy when finally formed. For example, the low-molecular-weight biaxial liquid crystal compound may have a group that becomes reactive for example by heat or light, and it consequently polymerizes or crosslinks, while losing its liquid crystallinity by the polymerization reaction by heat or light.

(Optically Anisotropic Layer)

The optically anisotropic layer is formed by the steps of: dissolving or dispersing the liquid crystal composition in the above solvent to prepare a coating solution, applying the coating solution to coat the oriented film, and orienting molecules of the liquid crystal compound. The coating solution can be applied by a known method (for example, a wire-bar coating method, an extrusion coating method, a direct gravure coating method, a reverse gravure coating method, or a die coating method).

The thickness of the optically anisotropic layer formed with the liquid crystal composition is preferably 0.1 to 20 µm, more preferably 0.2 to 15 µm, and most preferably 0.3 to 10 µm.

(Orientation of Liquid Crystal Compound)

Orientation of liquid crystal compounds is described in 'Liquid Crystal Handbook' (Maruzen Co., Ltd.), Chapter 2, "Orientation and Physical Properties of Liquid Crystals" (2000).

In the present invention, the orientation state is immobilized, without disturbing of the orientation state in the liquid crystal state, by a method of heating the liquid crystal composition once to its liquid crystal phase-forming temperature, and then cooling the composition while keeping its orientation state. It is also possible to immobilize the orientation state in the liquid crystal state, by heating the composition containing the liquid crystal composition of the present invention together with a polymerization initiator to its liquid crystal phase-forming temperature, allowing polymerization thereof, and then cooling the mixture. The immobilization of the orientation state in the present invention is preferably performed in the latter polymerization reaction. Examples of the polymerization reaction include thermal polymerization reaction by using a thermal polymerization initiator, photopolymerization reaction by using a photopolymerization initiator, and polymerization reaction by electron beam irradiation, but the polymerization reaction in photopolymerization reaction or by electron beam irradiation is preferable, for prevention of deformation or/and decomposition of the support and other parts by heat.

(Orientation Film (Oriented Film or Alignment Layer))

The orientation film can be provided, by rubbing an organic compound (preferably a polymer), oblique evaporation of an inorganic compound, forming a layer having a microgroove, or accumulation of an organic compound (for example, cotricosanoic acid, or methyl stearate) by the Langmuir-Blodgett method (LB film). Further, there are known orientation films having an orienting function imparted thereto by applying an electrical field, applying a magnetic field, or irradiating with light. Any layer may be used as the orientation film, if it can provide target orientation to the liquid crystal compound in the optically anisotropic layer to be formed on the orientation film to a desirable degree, but, in the present invention, use of an oriented film formed by rubbing or photoirradiation is preferable. An oriented film formed by rubbing a polymer layer is particularly preferred. The rubbing treatment can be conducted by rubbing the surface of a polymer layer with paper or cloth several times in a certain direction, and is preferably conducted in the manner described in "Liquid Crystal Handbook", published by Maruzen (2000). The oriented film preferably has a thickness of 0.01 to 10 μm, more preferably 0.05 to 3 μm.

Polymer materials usable for the oriented film are described in many publications and literatures, and many of them can be commercially available. The oriented film that can be used in the retardation sheet of the present invention, is preferably made of polyvinyl alcohol or a derivative thereof. Particularly preferred is a modified polyvinyl alcohol having a hydrophobic group. Orientation films for discotic liquid crystals can be used as the oriented film for liquid crystals, and are described in WO01/88574A1, p. 43, 1.24 to p. 49, 1.8.

(Rubbing Density of the Alignment Layer)

The tilt angel of liquid crystal compound molecules on the interface between the oriented film and the liquid crystal layer has a relationship to rubbing density of the oriented film. In fact, the higher the rubbing density is, the smaller the tilt angel is. The lower the rubbing density is, the larger the tilt angel is. Thus, the tilt angel can be controlled by controlling the rubbing density in the oriented film. The rubbing density can be controlled in the manner described in "Liquid Crystal Handbook", published by Maruzen (2000). The rubbing density (L) is quantified by mathematical formula (A):

$$L=Nl\{l+((2\pi rn)/(60v))\} \quad \text{Mathematical formula (A)}$$

in which N represents the number of rubbing the layer, l represents the contact length between the layer and a rubbing roller, r represents a radius of the rubbing roller, n represents revolutions of the roller (rpm), and v represents velocity of the moving stage (per second).

According to the mathematical formula (A), the rubbing density can be increased, by repeating the rubbing treatment (i.e. increasing the number of rubbings to be conducted), by increasing the contact length to the rubbing roller, by enlarging the radius of roller, by revving up the roller, or by moving the stage more slowly. Naturally, in the case where the rubbing density is wanted to decrease, these may be inversely operated.

(Vertically Oriented Film)

For vertical orientation of the liquid crystal compound on the oriented film side, effective is a method of reducing the surface energy of the oriented film or a method of vertically orienting the liquid crystal by the rejected-volume effect. For lowering the surface of the oriented film, a functional group may be introduced to the polymer.

To attain the above lowering, a hydrophobic functional group or atom is effective, and specifically a fluorine atom and a hydrocarbon group containing 10 or more carbon atoms can be effectively used as the functional group or atom. The hydrocarbon group or fluorine atom is introduced into a side chain of a polymer rather than a main chain, to arrange the hydrocarbon group or the fluorine atom on the surface of the orientation film. The fluoropolymer contains fluorine atoms preferably in an amount of 0.05 to 80 mass %, more preferably in an amount of 0.1 to 70 mass %, further preferably in an amount of 0.5 to 65 mass %, and most preferably in an amount of 1 to 60 mass %. The hydrocarbon group is an aliphatic group, an aromatic group, or a combination thereof. The aliphatic group can have a straight-chain, branched or cyclic structure. The aliphatic group preferably is an alkyl group (including a cycloalkyl group) or an alkenyl group (including a cycloalkenyl group). The hydrocarbon group can have a substituent group that is not strongly hydrophilic, such as a halogen atom. The hydrocarbon group contains preferably 11 to 100 carbon atoms, more preferably 10 to 60 carbon atoms, and most preferably 10 to 40 carbon atoms. The polymer preferably has a main chain of a polyimide structure or a polyvinyl alcohol structure.

The polyimide is usually synthesized by a condensation reaction of a tetracarboxylic acid and a diamine. Two or more tetracarboxylic acids, or two or more diamines can be used to synthesize a copolymerized polyimide. The hydrocarbon group can be present in repeating units derived from the tetracarboxylic acids, in repeating units derived from the diamines, or in both of the repeating units. The fluorine atom can also be present in the tetracarboxylic acid repeating units, in the diamine repeating units, or in both of the repeating units. In the case where the hydrocarbon group is introduced into the polyimide, the polymer preferably has a steroid structure in its side chain or its main chain. The steroid structure that is present in the side chain corresponds to the hydrocarbon group having 10 or more carbon atoms. Therefore, the steroid structure in the side chain has a function of orientating or aligning liquid crystal molecules essentially vertically. In the present specification, the steroid structure means a cyclopentanohydrophenanthrene ring, or a ring structure obtained by replacing a part of single bonds of the cyclopentanohydrophenanthrene ring with a double bond so long as the ring is aliphatic at that site (not forming any aromatic ring). Rigid substituents, such as the aforementioned steroid structure, alkyl chains, and the like, which show the rejected-volume effect on the liquid crystal molecules to be oriented, are more preferable.

Further, as another means of vertically orienting the liquid crystal compound, use may be preferably made of a method of mixing an organic acid with a polymer, such as polyvinylalcohol, modified polyvinylalcohol, or polyimide. Exampled of the acid preferably mixed include carboxylic acids, sulfonic acids, and amino acids. Acidic compounds among the air interface orientation agents described above may be used. Alternatively, quaternary ammonium salts can also be used favorably. The mixing rate is preferably 0.1 mass % to 20 mass %, more preferably 0.5 mass % to 10 mass %, with respect to the polymer. The polyvinyl alcohol (PVA) usable in the invention has a saponification degree in the range of, preferably 70 to 100%, more preferably 80 to 100%. The preferable polymerization degree of the polyvinyl alcohol is from 100 to 5,000.

By forming the oriented film by using a polymer having a side chain which contains a crosslinkable functional group bonded to the main chain or a polymer having a side chain which contains a crosslinkable functional group and has a function to orient liquid crystal molecule, and additionally forming a retardation film thereon by using a composition which contains a multifunctional monomer, it is possible to copolymerize the polymer in the oriented film and the multifunctional monomer in the retardation film formed thereon. As a result, covalent bonds are formed not only among multifunctional monomers, but also among oriented film polymers, and among multifunctional monomers and oriented film polymers, and thus, the oriented film and the retardation film bond to each other tightly. It is thus possible to improve the strength of the optical compensation sheet significantly, by forming an oriented film by using a polymer having crosslinkable functional groups. The crosslinkable functional group of the orientation film polymer preferably contains a polymerizable group, in the same manner as the polyfunctional monomer. Specific examples thereof are described in JP-A-2000-155216, paragraph Nos. [0080] to [0100].

The orientation film polymer can be crosslinked with a crosslinking agent, separately from the above-mentioned crosslinkable functional group. Examples of the crosslinking agent for the polymer include aldehydes, N-methylol compounds, dioxane derivatives, compounds that work when the carboxylic group is activated, active vinyl compounds, active halogen compounds, isooxazoles, and dialdehyde starch. Two or more crosslinking agents may be used in combination. Specifically, compounds described in, e.g., JP-A-2002-62426, paragraph Nos. [0023] to [0024], can be used. Highly reactive aldehydes are preferred, and glutaraldehyde is particularly preferred.

The addition amount of the crosslinking agent is in the range of preferably 0.1 to 20 mass %, more preferably 0.5 to 15 mass %, based on the amount of the polymer. The amount of non-reacted crosslinking agent remaining in the orientation film is preferably 1.0 mass % or less, more preferably 0.5 mass % or less. The adjustment as described above makes it possible to give a sufficient endurance to the orientation film without generating any reticulation even if the orientation film is used in a liquid crystal display device for a long period of time or is allowed to stand in high-temperature and high-humidity atmosphere for a long period of time.

The orientation film can be basically formed by applying the composition containing the polymer (i.e. the orientation film-forming material) and the cross-linking agent as recited above on a transparent support, drying by heating (to cause cross-linking reaction), and rubbing the coated surface if necessary.

Rubbing is preferably avoided for vertical orientation of rod-shaped liquid crystal compounds. The cross-linking reaction, as mentioned above, may be carried out in an arbitrary stage, after coating the transparent support with the composition. In the case of using a water-soluble polymer, such as PVA, as the orientation film forming material, a mixture of water with an organic solvent having a defoaming action, such as methanol, is preferably employed as the mixed solvent of the coating solution. The suitable ratio of water to methanol is preferably from 0:100 to 99:1, more preferably from 0:100 to 91:9, by mass. By the use of such a mixed solvent, the generation of foams can be prevented, to ensure markedly decreased defects in the orientation film, especially the surface of the retardation layer.

Preferred examples of a coating method for forming the orientation film include a spin coating method, an inkjet method, a dip coating method, a curtain coating method, an extrusion coating method, a rod coating method, and a roll coating method. Of these methods, the rod coating method and the inkjet method are particularly preferred over the others. The preferable thickness of the film after drying is from 0.1 to 10 µm. The drying by heating can be performed at a temperature of 20° C. to 110° C. In order to form cross-links to a satisfactory extent, the drying temperature is preferably from 60° C. to 100° C., more preferably from 80° C. to 100° C. The drying time is preferably from 1 minute to 36 hours, more preferably from 1 to 30 minutes. Further, it is preferable to adjust the pH to an optimum value for the cross-linking agent to be used. In the case of using glutaraldehyde as the cross-linking agent, the preferable pH is from 4.5 to 5.5, particularly preferably 5.

The retardation film according to the present invention per se after applying and forming under heat is sufficiently adhesive to a glass substrate, or a color filter, orientation film, overcoat (OC) layer, or reflector, each of which is formed on a glass substrate, and it is possible to adjust the adhesive force according to application by the following method. Specific examples of such a method include surface activation, surface modification, or addition of an adhesion accelerator to the retardation film-coating solution.

Examples of the surface activation method include chemical treatment of the surface with an acid or alkali, mechanical treatment, corona discharge treatment, flame treatment, UV treatment, high-frequency wave treatment, glow discharge treatment, active plasma treatment, and ozone oxidation. The glow discharge treatment referred to herein may be a treatment with low-temperature plasma generated in a low-pressure gas having a pressure of $10^{-3}$ to 20 Torr, or preferably with plasma under the atmospheric pressure. A plasma excitation gas is a gas which can be excited to plasma under conditions as described above, and examples thereof include argon, helium, neon, krypton, xenon, nitrogen, carbon dioxide, flons such as tetrafluoromethane, and a mixture thereof. Details thereof are described in "Hatsumei Kyokai Kokai Giho" (Kogi No. 2001-1745, published Mar. 15, 2001, Japan Institute of Invention and Innovation), pp. 30 to 32, which detailed techniques can be preferably used in the present invention. In the plasma treatment under the atmospheric pressure, to which attention has been paid in recent years, for example, a radiating energy of 20 to 500 kGy is used under the condition of 10 to 1,000 keV, and preferably a radiating energy of 20 to 300 kGy is used under the condition of 30 to 500 keV.

Examples of the surface modification method include formation of an undercoat layer, silane coupling treatment with a silane-coupling agent described below, and formation of an anchor coat layer. Details of the undercoat layer are described in "Hatsumei Kyokai Kokai Gihou" Kogi No. 2001-1745, Mar. 15, 2001, p. 32.

Preferable examples of the adhesion accelerator that can be used in the method of adding said adhesion accelerator to the retardation film-coating solution include those described, for example, in JP-A-5-11439, JP-A-5-341532, and JP-A-6-43638. Specific examples thereof include benzimidazole, benzoxazole, benzothiazole, 2-mercaptobenzimidazole, 2-mercaptobenzoxazole, 2-mercaptobenzothiazole, 3-morpholinomethyl-1-phenyl-triazol-2-thione, 3-morpholinomethyl-5-phenyl-oxadiazol-2-thione, 5-amino-3-morpholinomethyl-thiadiazol-2-thione, and 2-mercapto-5-methylthio-thiadiazole, triazole, tetrazole, benzotriazole, carboxybenzotriazoles; amino-group-containing benzotriazoles, polymerizable organometal compounds having a hydrolytic group, a radical polymerization group, or the like; α,β-ethylenically unsaturated carboxylic esters, silane-coupling agents, and titanium coupling agents.

Examples of the silane-coupling agent include N-β-(aminoethyl)-γ-aminopropyltrimethoxysilane, γ-methacryloxypropyltrimethoxysilane, vinyltrichlorosilane, vinyl-tris(β-methoxyethoxy)silane, vinyltriethoxysilane, vinyltrimethoxysilane, γ-aminopropyltriethoxysilane, γ-aminopropyltrimethoxysilane, γ-aminopropyltripropoxysilane, γ-aminopropyltributoxysilane, γ-aminoethyltriethoxysilane, γ-aminoethyltrimethoxysilane, γ-aminoethyltripropoxysilane, γ-aminoethyltributoxysilane, γ-aminobutyltriethoxysilane, γ-aminobutyltrimethoxysilane, γ-aminobutyltripropoxysilane, and γ-aminobutyltributoxysilane; and examples of the titanium coupling agent include γ-aminopropyltriethoxyltitanium, γ-aminopropyltrimethoxytitanium, γ-aminopropyltripropoxytitanium, γ-aminopropyltributoxytitanium, γ-aminoethyltriethoxyltitanium, γ-aminoethyltrimethoxytitanium, γ-aminoethyltripropoxytitanium, γ-aminoethyltributoxytitanium, γ-aminobutyltriethoxyltitanium, γ-aminobutyltrimethoxytitanium, γ-aminobutyltripropoxytitanium, and γ-aminobutyltributoxytitanium. These compounds may be used in combination of two or more thereof.

The content of the adhesion accelerator is preferably 0.001 mass % to 20 mass %, more preferably 0.01 mass % to 10 mass %, and particularly preferably 0.1 mass % to 5 mass %, with respect to the total components in the retardation layer.

It is also possible to control the adhesiveness by using a polymerization initiator. Examples of the polymerization initiator include halogenated hydrocarbon derivatives (such as those having a triazine skeleton and those having an oxadiazole skeleton), hexaarylbiimidazoles, oxime derivatives, organic peroxides, thio compounds, ketone compounds, acylphosphine oxide compounds, aromatic onium salts, metallocenes, and the like. Among them, triazine skeleton-containing halogenated hydrocarbons, oxime derivatives, ketone compounds, and hexaarylbiimidazole compounds are preferable, from the viewpoints of sensitivity, storage life, adhesiveness, and others.

(Transparent Support)

There is no particular restriction on the material of the support (e.g. preferably a transparent support) of the phase retarder of the present invention as long as it is optically isotropic and has a transmittance of 80% or more, but a polymer film is preferably used. Examples of the polymer include cellulose esters (e.g., cellulose diacetate, cellulose triacetate), norbornene-based polymers, and poly(meth)acrylates. Many commercially available polymers can be preferably used. In consideration of optical characters, cellulose esters are preferred, and cellulose esters of lower fatty acids are more preferred. The term "lower fatty acids" means fatty acids having 6 or less carbon atoms. The number of carbon atoms is preferably 2 (cellulose acetate), 3 (cellulose propionate) or 4 (cellulose butyrate). Cellulose triacetate is particularly preferred. Cellulose esters of mixed fatty acids, such as cellulose acetate propionate, and cellulose acetate butyrate, are also usable. Further, any polymer that tends to show birefringence (e.g., polycarbonate, polysulfone) can be also used, if the molecule of the polymer is modified in the manner described in WO00/26705 to reduce the birefringence.

In the present invention, the transparent support and the orientation film are essential in the step(s) of forming the retardation film, but once the retardation film is prepared, which may be transferred onto another substrate, or the transparent support and/or the orientation film may be removed, for example, by peeling off the same.

Cellulose esters (particularly cellulose triacetate) that can be preferably used for the transparent support are described below in detail. As the cellulose ester, cellulose acetate having an acetylation degree of 55.0 to 62.5% is preferably used. The acetylation degree is more preferably in the range of 57.0 to 62.0%. The acetylation degree means the amount of an acetic acid component bonded per the unit mass of cellulose. The acetylation degree is determined, according to the Measurement and Calculation of Acetylation Degree, as described in ASTM:D-817-91 (Test Method of Cellulose acetate, etc.). The cellulose ester has a viscosity average polymerization degree (DP) of preferably 250 or more, more preferably 290 or more. The cellulose ester for use in the present invention preferably has a narrow molecular mass distribution in terms of Mw/Mn (Mw is a mass average molecular mass, and Mn is a number average molecular mass) as measured by gel permeation chromatography. Specifically, the value of Mw/Mn is preferably from 1.0 to 4.0, more preferably from 1.3 to 3.5, and most preferably from 1.4 to 3.0.

In cellulose triacetate, hydroxyl groups at 2-, 3- and 6-positions of cellulose are not equally substituted (namely, the substitution degree at each position is not equal to one third of the total substitution degree), and the substitution degree at 6-position is apt to be relatively small. In the cellulose (tri) acetate for use in the present invention, however, the substitution degree at 6-position hydroxyl group is preferably larger than those at 2- and 3-positions. The substitution degree of the hydroxyl group by an acyl group at 6-position is preferably 30% to 40%, more preferably 31% to 40%, most preferably 32% to 40%, based on the total substitution degree. Further, the substitution degree at 6-position is preferably 0.88 or more. The hydroxyl group at 6-position may be replaced with an acyl group having 3 or more carbon atoms other than acetyl group (e.g., propionyl, butylyl, valeronyl, benzoyl, acryloyl). The substitution degree at each position can be measured by means of NMR. A cellulose ester having a high substitution degree at 6-position can be prepared, according to the methods described in JP-A-11-5851, paragraph Nos. 0043 to 0044 (Synthesis example 1), 0048 to 0049 (Synthesis example 2), and 0051 to 0052 (Synthesis example 3).

The polymer film, particularly the cellulose acetate film, that can be used as the transparent support may contain a retardation-increasing agent, to have a proper retardation. The retardation-increasing agent is preferably an aromatic compound having at least two aromatic rings. The retardation-increasing agent is incorporated in an amount of preferably 0.01 to 20 mass parts, more preferably 0.05 to 15 mass parts, and most preferably 0.1 to 10 mass parts, based on 100 mass parts of the cellulose acetate. Two or more aromatic compounds may be used in combination. The aromatic ring in the aromatic compound may be an aromatic hydrocarbon ring or an aromatic heterocycle.

As the aromatic hydrocarbon ring that the aromatic compound as the retardation-increasing agent has, a six-membered ring (namely, a benzene ring) is particularly preferred. The aromatic heterocycle is generally unsaturated. The aromatic heterocycle is preferably a five-, six- or seven-membered ring, and more preferably a five- or six-membered ring. The aromatic heterocycle generally has double bonds in the highest number. The hetero-atom in the ring preferably is nitrogen atom, oxygen atom or sulfur atom, and more preferably is nitrogen atom. Examples of the aromatic heterocycle include furan ring, thiophene ring, pyrrole ring, oxazole ring, isoxazole ring, thiazole ring, isothiazole ring, imidazole ring, pyrazole ring, furazane ring, triazole ring, pyran ring, pyridine ring, pyridazine ring, pyrimidine ring, pyrazine ring, and 1,3,5-triazine ring. Preferred aromatic rings are benzene ring, furan ring, thiophene ring, pyrrole ring, oxazole ring, thiazole ring, imidazole ring, triazole ring, pyridine ring, pyrimidine ring, pyrazine ring, and 1,3,5-triazine ring. Benzene ring and 1,3,5-triazine ring are more preferred. The aromatic compound particularly preferably contains at least one 1,3,5-triazine ring. The number of aromatic rings in the aromatic compound is preferably in the range of 2 to 20, more preferably in the range of 2 to 12, further preferably in the range of 2 to 8, and most preferably in the range of 2 to 6.

The relation of the two or more aromatic rings that the aromatic compound as the retardation-increasing agent have is categorized into three cases, namely (a) the case in which the aromatic rings form a condensed ring, (b) the case in which the aromatic rings are connected through a single bond, and (c) the case in which the aromatic rings are connected through a linking group. (In this case, a spiro-bonding is not formed because the rings are aromatic.) The relation of the aromatic rings may be any of the cases (a) to (c). The retardation-increasing agents as above are described, for example, in WO01/88574A1, WO00/2619A1, JP-A-2000-111914, JP-A-2000-275434, and JP-A-2002-363343.

The cellulose acetate as the transparent support may be a single film or may consist of two or more layers. For example, in the case of the cellulose triacetate, a single film of cellulose triacetate can be prepared by the drum-casting method or by the band-casting method, as disclosed in, for example, JP-A-7-11055. A cellulose triacetate support consisting of two or more layers can be prepared by the cooperative casting method described in, for example, JP-A-61-94725 and JP-B-62-43846 ('JP-B' means examined Japanese patent publication). That is, in those methods, first, flakes of the raw materials are dissolved in a solvent, such a halogenated hydrocarbon (e.g., dichloromethane), an alcohol (e.g., methanol, ethanol, butanol), an ester (e.g. methyl formate, methyl acetate) or an ether (e.g. dioxane, dioxolane, diethyl ether). To the resultant solution, any of various additives, such as a plasticizer, an ultraviolet absorber, a deterioration inhibitor, a slipping agent, and a releasing aid, is added, if desired. The thus-prepared solution (referred to as "dope") is then cast onto a support (a horizontal endless metal band or a rotating drum) from a dope-supplying means (referred to as "die"). If a single film is to be formed, a single dope is cast as a single layer. If two or more layers are to be formed, a highly concentrated cellulose ester dope and a low concentrated one are cooperatively cast so that the highly concentrated dope and the low concentrated one may be side-by-side spread. If desired, one high-concentration dope layer is cast so that it would be sandwiched with two low-concentrated dope layers on the both sides thereof, to give a three-layered film. The spread dope(s) are dried on the support until a rigid film is formed. The film is then peeled off and transferred by any transferring means through a drying zone, to remove the solvent.

As described in the above, a typical solvent for dissolving cellulose triacetate is dichloromethane, but in consideration of protecting the global environmental conditions and working conditions, the solvent preferably contains essentially no halogenated hydrocarbon, such as dichloromethane. The "containing essentially no (or free from) halogenated hydrocarbon" means that the content of halogenated hydrocarbon in the organic solvent to be used is preferably less than 5 mass % (more preferably less than 2 mass %). In order to prepare a dope of cellulose triacetate from a solvent containing essentially no halogenated hydrocarbon, such as dichloromethane, a particular dissolving method described in the below is needed. That dissolving method is referred as "cooling dissolving method" or "heating dissolving method". The cellulose (tri)acetate film essentially free from halogenated hydrocarbon, such as dichloromethane, and the preparation process thereof are described in Japan Institute of Invention and Innovation, Technical report (Kogi) No. 2001-1745, published on Mar. 15, 2001.

Additives for improving various physical characteristics of cellulose acetate are also described in the aforementioned Kogi No. 2001-1745, and are preferably usable in the present invention.

If made of cellulose acetate, the transparent support is preferably subjected to the saponification treatment so that an adhesive layer may adhere well to another functional layer(s) and the support upon adhering, in which the adhesive layer may be provided on one surface side of the support. The saponification treatment can be performed in the known manner. For example, a film of cellulose acetate is immersed in an alkaline solution in a proper period of time. The thus-immersed film is then preferably washed with water well or neutralized with a diluted acid (e.g. by immersing the film into the diluted acid), so as to remove alkaline component in the film. The saponification treatment makes the surface of the transparent support hydrophilic, and the hydrophilic surface is particularly effective in improvement on adhering onto an oriented film (a polarizing membrane) mainly made of polyvinyl alcohol. Further, dust in the air seldom attaches on the hydrophilic surface, and is therefore prevented from getting into between the transparent support and the polarizing membrane upon adhering the support and the polarizing membrane. Consequently, the saponification treatment is effective in prevention of the dust from causing spot defects.

The saponification treatment is performed so that the surface of the transparent support would give a contact angle of preferably less than 40 degrees, more preferably less than 30 degrees, further preferably less than 20 degrees, to water.

Specifically, the alkali saponification is performed according to one selected from the following two methods. The following method (1) is favorable because it is performed in the process same as that for commonly-used cellulose acetate films, but may possibly cause such problems that deterioration of the film may occur due to surface alkali hydrolysis by saponification to the optically anisotropic layer surface and that contamination may occur by the remaining saponification solution, if any. In such a case, the following method (2) is favorable, although it is rather a special step.

(1) After an optically anisotropic layer is formed on the transparent support, the thus-laminated film is immersed in an alkali solution at least one time, to saponify the back surface of the film.

(2) Before or after an optically anisotropic layer is formed on the transparent support, an alkali solution is spread to coat the back surface of the transparent support (i.e. the surface opposite to one on which the optically anisotropic layer is to be provided or already provided), and the thus-coated support is then heated, washed with water and/or neutralized, to saponify only the backing surface of the transparent support.

The surface energy of the cellulose acetate film is preferably not less than 55 mN/m, more preferably in the range of 60 to 75 mN/m. The surface energy of a solid can be determined by the contact angle method, the wet heating method, or the adsorption method. These methods are described in "The basic theory and application of wetting", published by Realize Co., Ltd, on Dec. 10, 1989. For measuring the cellulose acetate film in the present invention, the contact angle method is preferred to use. In that method, specifically, two solutions having known surface energies are dropped onto the cellulose acetate film. The contact angle of each drop is measured, and the surface energy of the film is calculated from the measured contact angles. The contact angle is defined to be an angle, which angle is formed by including the droplet, and is formed between the film surface and the tangent to the droplet surface, at the crossing point of the droplet surface and the film surface.

The cellulose acetate film has a thickness generally in the range of 5 to 500 µm, preferably in the range of 20 to 250 µm, more preferably in the range of 30 to 180 µm, particularly preferably in the range of 30 to 110 µm.

(Wavelength Dispersion)

The retardation sheet of the present invention preferably gives wavelength dispersion, as the preferable ranges, for satisfying the relationships as represented by formulas (A-1) and (A-2):

$$0.60 < R(450)/R(550) < 0.99 \quad \text{Formula (A-1)}$$

$$1.01 < R(650)/R(550) < 1.35 \quad \text{Formula (A-2)}$$

In the formulae, R(450), R(550), and R(650) are retardation values measured at 450 nm, 550 nm, and 650 nm, respectively. Each value of the measurement wavelength includes an error of ±10 nm.

At the outside of the above ranges, for example, the phase retarder when used as a λ/4 plate may convert a incident linearly polarized light of 400 to 700 nm into a completely circularly polarized light, as a resultant polarized state, at a particular wavelength. At the wavelengths other than the above particular wavelength, however, the converted light is often far from the circularly polarized light, which is a problem. In consideration of this, the phase retarder more preferably gives wavelength dispersion for satisfying the relationship in formulas (A-3) and (A-4):

$$0.60 < R(450)/R(550) < 0.95 \quad \text{Formula (A-3)}$$

$$1.04 < R(650)/R(550) < 1.35 \quad \text{Formula (A-4)}$$

In the formulas, R(450), R(550), and R(650) are retardation values measured at 450 nm, 550 nm, and 650 nm, respectively. Each value of the measurement wavelength includes an error of ±10 nm.

[Polarizing Plate]

The retardation sheet of the present invention is particularly useful for a polarizing plate protective film. When the sheet is used as a polarizing plate-protective film, the production method of polarizing plate is not particularly limited, but the polarizing plate may be produced in a usual manner. For example, there is a method of producing a polarizing plate, comprising the steps of: alkali-treating the obtained cellulose (cellulose acylate) film; and sticking, with using an aqueous solution of completely saponificated polyvinyl alcohol, the alkali-treated film one by one onto each side of a polarizer produced by dipping a polyvinyl alcohol film in an iodine solution, followed by stretching. In place of the alkali treatment, an enhanced adhesion processing, as described in JP-A-6-94915 and JP-A-6-118232, may be adopted to the aforementioned production method.

Examples of the adhesive that can be used in bonding between the treated side of the protective film and the polarizer, include polyvinyl alcohol-series adhesives, such as polyvinyl alcohol and polyvinyl butyral; and vinyl-series latexes, such as butyl acrylate.

A polarizing plate is generally composed of a polarizer and protecting films to protect both surfaces of the polarizer, and the thus-prepared polarizing plate may be further provided with a protect film stuck to one surface of the polarizing plate, and a separation film stuck to the opposite surface of the polarizing plate. The protect film and the separation film are used, in order to protect the polarizing plate when the polarizing plate is shipped and subjected to a product testing or the like. In this case, the protect film is stuck in order to protect the surface of a polarizing plate, and the film is used at the side of the surface opposite to the surface with which the polarizing plate is stuck to a liquid crystal plate. Meanwhile, the separation film is used to cover an adhesive layer to be stuck to the liquid crystal plate, and the film is used at the same side as the surface with which the polarizing plate is stuck to a liquid crystal plate.

In a liquid crystal display device, usually, a substrate containing liquid crystals is disposed between two polarizing plates. A polarizing-plate protective film to which the cellulose (cellulose acylate) film according to the present invention is applied can exhibit excellent display performances, regardless of the site the film is to be disposed. In particular, because a transparent hard coat layer, an anti-glare layer, an anti-reflection layer, and the like layers are disposed to a polarizing-plate protective film to be disposed at the outermost surface at the displaying side of the liquid crystal display device, employment of the aforementioned polarizing-plate protective film of the present invention at this site is especially preferable.

When the optical film containing the liquid crystal compound of the present invention is used as a protection film for a polarizing plate, its photoelasticity is preferably $0.5 \times 10^{-13}$ to $9.0 \times 10^{-13}$ [cm$^2$/dyn] and its moisture permeability (a value estimated at a film thickness of 80 µm) is preferably 180 to 435 [g/cm$^2 \cdot$24 h]. The photoelasticity is more preferably $0.5 \times 10^{-13}$ to $7.0 \times 10^{-13}$ [cm$^2$/dyn], still more preferably, $0.5 \times 10^{-13}$ to $5.0 \times 10^{-13}$ [cm$^2$/dyn]. The moisture permeability (a value estimated at a film thickness of 80 µm) is more preferably 180 to 400 [g/cm$^2 \cdot$24 h], still more preferably 180 to 350 [g/cm$^2 \cdot$24 h]. If the film according to the present invention has such properties, it is possible to reduce deterioration in performance under influence of humidity, when used as a protection film for a polarizing plate.

The optically anisotropic film (optically anisotropic film (A)) prepared by orienting and immobilizing the liquid crystal compound of the present invention almost in the vertical direction can be used as a brightness-improving film or an optical compensation film for IPS.

The optically anisotropic film (A) according to the present invention can be used in combination with a polarizing film in the application for an elliptical polarizing plate. Further, it is possible to expand the view angel of a liquid crystal display device, by using it in combination with a polarizing film in a transmission liquid crystal display device.

The optically anisotropic film (A) according to the present invention may have an adhesive layer. The adhesive layer can be used for adhesion to the liquid crystal cell and also for lamination with another optically anisotropic film (optically anisotropic film (B)) or the like.

The adhesive layer can be formed on one side or both sides of a polarizing plate or an optical film, as a superposed layer with a film different in composition or kind. When formed on both sides, the adhesive layers may be different in composition, kind, thickness, and the like, on the top and bottom surfaces of the polarizing plate or optical film. The thickness of the adhesive layer may vary according to the application, adhesive strength, and others, but it is preferably 1 to 500 µm, more preferably 5 to 200 µm, and still more preferably 10 to 100 µm.

The exposed adhesive layer is temporarily covered with a separator for prevention of contamination and the like, till provided for the practical use. It is thus possible to prevent contact to the adhesive layer under normal handling condition. Any one of usual separators excluding the thickness condition may be used as the separator, and examples thereof include films of plastic film, rubber sheet, paper, cloth, nonwoven fabric, net, foamed sheet, metal foil, a laminate thereof, and a coated product thereof coated if necessary with, for example, a proper release agent, such as a silicone-based, long-chain alkyl-based, or fluorine-based agent, or molybdenum sulfide.

[Brightness-Improving Film According to the Present Invention]

To a liquid crystal display device displaying image by using the change in polarization state by movement of liquid crystal, a polarizing plate is necessary, and, because of it, more than half of the backlight irradiated is absorbed by the polarizing plate and not used in displaying the image. The brightness-improving film has a function to reflect the thus-absorbed polarized light back toward the backlight side, and the thus-reflected polarized light is reflected again or modified in its polarization state by an optical part in the backlight side and transmitted through the polarizing plate and incident into the liquid crystal display device. Thus, it is possible to use the light absorbed by the polarizing plate and not used in displaying in the conventional technique, and consequently, to improve the brightness of the display of the liquid crystal display device.

(Configuration)

The brightness-improving film is preferably used, as it is bonded to the polarizing plate of the back side of a liquid crystal display device. The brightness-improving film according to the present invention is formed by placing the optically anisotropic film (A) between a cholesteric liquid crystal film and a quarter-wavelength plate. The cholesteric liquid crystal layer has a function to reflect one of the right- and left-circularly polarized light components and allow transmission of the other component in that sense. The transmitted circularly polarized light is converted to a linearly polarized light by using a quarter-wavelength plate for more efficient transmission through the polarizing plate. The quarter-wavelength plate is placed between the polarizing plate and the cholesteric liquid crystal film for that purpose. However, the light obliquely entering into and obliquely going out from the cholesteric liquid crystal layer is influenced by the retardation in the thickness direction of the cholesteric liquid crystal layer for elliptical polarization, causing color development of the layer and the loss in the efficiency of using the light when seen from an oblique direction. The optically anisotropic film (A) has a function to compensate the retardation in the thickness direction of the cholesteric liquid crystal layer, and thus, reduces the color development and prevents the loss in use efficiency. With respect to the Re of the optically anisotropic film (A), the in-plane retardation (Re) is preferably 40 nm or less, more preferably 20 nm or less, and still more preferably 10 nm or less. On the other hand, the retardation in the thickness direction (Rth) is preferably −100 nm to −600 nm, more preferably −150 nm to −450 nm, and fisher preferably −200 nm to −350 nm, from the viewpoint of optical compensation effect. The cholesteric liquid crystal film and the quarter-wavelength plate are used as selected from various films used as brightness-improving films without any restriction.

The brightness-improving film can be formed, for example, by laminating an optically anisotropic film (A) formed on the low-Rth transparent substrate between a cholesteric liquid crystal film and a quarter-wavelength plate with an adhesive.

The brightness-improving film may alternatively formed, by forming an optically anisotropic film (A) according to the present invention by using a quarter-wavelength plate as the support, and bonding a cholesteric liquid crystal film onto the optically anisotropic film (A) via an adhesive layer.

Yet alternatively, the brightness-improving film may be prepared, by transferring an optically anisotropic film (A) formed on a support onto one of cholesteric liquid crystal film or quarter-wavelength plate via an adhesive layer, and bonding, onto the thus-transferred film (A), to the other of the cholesteric liquid crystal film or quarter-wavelength plate, which has not been used for transferring in the above, via an adhesive layer.

The adhesive for forming the adhesive layer is not particularly limited, and use may be made by selecting properly, for example, from acrylic polymers, silicone polymers, polyesters, polyurethanes, polyamides, polyethers, and polymers containing a fluorine- or rubber-based polymer as base polymer. In particular, use may be preferably made, for example, of an acrylic adhesive, which is excellent in optical transparency, is favorable in adhesion properties, such as wettability, cohesiveness and adhesiveness, is excellent in weather resistance and heat resistance, and others.

The adhesive layer is formed properly by any method. For example, the adhesive layer is formed, by preparing an adhesive solution by dissolving or dispersing a base polymer or a composition thereof in a suitable solvent, such as toluene or ethyl acetate, or a mixed solvent thereof to a concentration of about 10 to 40 mass %, and applying the resultant mixture on a substrate or a liquid crystal film directly by a proper application method, such as casting or coating, thereby to provide the adhesive layer; or the adhesive layer is formed, by forming an adhesive layer on a separator in the same manner as above, and transferring the resultant layer onto the liquid crystal layer. The adhesive layer may contain various additives, for example, resins of natural and synthetic products, such as tackifier resin; fillers, such as glass fiber, glass bead, metal powder, and other inorganic powders; and other additives that can be added to the adhesive layer, such as pigment, colorant, and antioxidant. Further, the adhesive layer may have optical diffusing property, by containing fine particles therein.

In transferring, via an adhesive layer, the optically anisotropic film (A) formed on a substrate, the optically anisotropic film (A) is preferably surface-treated. The surface treatment method is not particularly limited, and preferable examples thereof include corona discharge, sputtering, low-pressure UV irradiation, and plasma treatment, which allow preservation of the transparency of the optically anisotropic film (A). Among the surface treatment methods above, corona discharge treatment is more preferable.

(Cholesteric Liquid Crystal Film)

The cholesteric liquid crystal film preferably reflects either right-handed circularly polarized light or left-handed circularly polarized light in a wide wavelength range of visible light. A film reflecting the light entering in the normal direction of the film in a wavelength range of 400 nm to 1,100 nm is preferable, more preferably that in a wavelength range of 430 nm to 800 nm.

The wavelength of the reflected light is dependent on the product of the helical cycle (pitch) of the cholesteric liquid crystal and the average refractive index of the cholesteric liquid crystal, in the direction of the light entering in the normal direction, and thus, a film having a helical pitch of 250 nm to 800 nm can be used. However, the width of the reflection wavelength region of circularly polarized light, due to the cholesteric liquid crystal, is dependent on the product of the refractive index anisotropy of the cholesteric liquid crystal and the pitch, and thus, common liquid crystal materials hardly have a reflection wavelength region width of over 200 nm. Thus, for assuring a wide reflection band over the visible light range, any of the following methods is taken. That includes: a method of using a lamination structure of two, three or more films different in reflection wavelength; and a method of laminating cholesteric liquid crystal films having reflection bands respectively of about 400 mm and 900 nm, diffusing the cholesteric liquid crystal components in the film thickness direction under heating, thereby to form continuous distribution of pitches in the thickness direction, and thus to widen the reflection band. Other examples of the method of forming continuous distribution of pitches in the thickness direction include: a method of orienting a cholesteric liquid crystal by using a UV absorbent and a photoisomerization chiral agent as components for the cholesteric liquid crystal, and irradiating the film with UV ray; and a method of adding a monomer different in polymerization reaction rate and a UV absorbent, as an additional component for the cholesteric liquid crystal, and irradiating the film with low-illuminance UV ray.

The cholesteric liquid crystal film is formed, by providing a support on which an oriented film is formed and rubbed, orienting a cholesteric polymer liquid crystal or a polymerizable cholesteric liquid crystal such that the helical axis of the cholesteric polymer liquid crystal or the polymerizable cholesteric liquid crystal is oriented in the direction almost parallel to the normal direction of the support, and immobilizing the thus-oriented liquid crystal on the support. The cholesteric liquid crystal is obtained, for example, by mixing a rod-shaped liquid crystal compound with an optically active compound. The rod-shaped liquid crystal compound preferably has a plurality of polymerizable groups. A polymer having an optically active group may be used for the cholesteric polymer liquid crystal. Increase in the amount of the optically active compound to be mixed leads to shortening of the cholesteric liquid crystal pitch in proportion to the blending amount, and thus, it is possible to adjust the reflection band easily by using this relationship.

The thickness of the cholesteric liquid crystal film is preferably 1 to 30 μm, more preferably 2 to 15 μm. The cholesteric liquid crystal film may contain one or more additives as needed, and examples thereof include inorganic compounds, organic compounds, metals, and compounds thereof, such as polymer, air-interface orienting agent, surfactant, stabilizer, and plasticizer.

(Quarter-Wavelength Plate)

As a quarter-wavelength plate, use may be made of an arbitrarily retardation sheet suitable for a target application use. The optical properties of the quarter-wavelength plate, such as retardation, can be controlled, by laminating two or more retardation sheets. Examples of the retardation sheets include birefringent films prepared by stretching a film of an arbitrarily polymer, such as of polycarbonate, norbornene-based resin, polyvinylalcohol, polystyrene, polymethyl methlacrylate, polypropylene or other polyolefin, polyarylate, or polyamide; oriented films of liquid crystal material, such as liquid crystal polymer; and films carrying an orientation layer of liquid crystal material. The thickness of the quarter-wavelength plate is preferably 0.5 to 200 μm, more preferably 1 to 100 μm.

A retardation sheet functioning as a quarter-wavelength plate in a wide wavelength range, for example, in the visible light region, can be prepared, for example, by laminating a retardation layer functioning as a quarter-wavelength plate to a pale-colored light at a wavelength of 550 nm with another retardation layer showing other retardation characteristics, such as a retardation layer functioning as a half-wavelength plate. Thus, the retardation sheet placed between the polarizing plate and the brightness-improving film may be one layer or two or more layers of retardation films.

[Structure and Forming Method of the Optical Film of the Present Invention]

The optical film of the present invention can be applied to liquid crystal display devices of various display modes, for example, TN (Twisted Nematic), FFS (Fringe-Field Switching), IPS (In-Plane Switching), FLC (Ferroelectric Liquid Crystal), OCB (Optically Compensatory Bend), STN (Super Twisted Nematic), VA (Vertically Aligned), and HAN (Hybrid Aligned Nematic). The optical film according to the present invention has an action to compensate, for example, the color development, and the change in view angle, of various wavelength plates and liquid crystal layers caused by birefringence.

The optical film of the present invention is also effective in reducing the light leakage, as observed when the quadrature polarizing plate is seen from an oblique angle, caused by deviation of the polarization-axis crossing angle from the right-crossing direction.

The liquid crystal display device of the present invention preferably has the optically anisotropic film (A) and at least one or more optically anisotropic films (B).

The optical film according to the present invention may be a laminate optical film, for example, prepared by applying an optically anisotropic film (A) on a support of an optically anisotropic film (B), followed by orienting and immobilizing the film (A).

Alternatively, the optically anisotropic film (A) formed on a support may be transferred via an adhesive layer onto an optically anisotropic film (B), to give a lamination. Yet alternatively, the optically anisotropic film (A) formed on a low-Rth transparent support may be bonded and laminated onto an optically anisotropic film (B) with an adhesive.

(Optically Anisotropic Film (B))

As the optically anisotropic film (B), use may be made, for example, of a film for compensation of, for example, color development and change in view angle, caused by birefringence of various wavelength plates and liquid crystal layers; and it is possible to control the optical properties, such as retardation, by laminating two or more optically anisotropic films (B) including an optically anisotropic film (B) suitable for the intended application. Examples of the optically anisotropic film (B) include birefringent films prepared by stretching (drawing) a film of an arbitrarily polymer, such as polycarbonate, norbornene-based resin, polyvinylalcohol, polystyrene, polymethyl methacrylate, polypropylene or other polyolefin, polyarylate, or polyamide; oriented films of a liquid crystal compound, such as liquid crystal polymer; films carrying an orientation layer of liquid crystal material; and the like. Alternatively, use may also be made of a biaxially oriented film, such as a birefringent film biaxially oriented or oriented in two directions perpendicular to each other, or an inclined-orientation film. Examples of the inclined-orientation film include films prepared, by bonding a heat shrinkable film onto a polymer film, and allowing orientation or/and shrinkage of the polymer film under the shrinkage force by heating; films prepared, by orienting a liquid crystal polymer in an oblique direction, and the like. In particular, the transparent optically anisotropic film and the low-Re cellulose acylate film described below are used preferably in combination with the optically anisotropic film (A), as an optically anisotropic film (B) showing higher-performance optical properties.

<<Transparent Optically Anisotropic Film>>

As the transparent optically anisotropic film for the optically anisotropic film (B), use may be preferably made of transparent optically anisotropic film of polycarbonate, norbornene-based resin, or cellulose acylate having an in-plane retardation (Re) of 0 nm to 250 nm and a thickness-direction retardation (Rth) of 0 nm to 350 nm.

For effective reduction of the light leakage from the polarizing plate in the oblique direction, Re is more preferably 40 nm to 250 nm, and still more preferably 60 nm to 200 nm. For effective reduction of the light leakage in the oblique direction, Rth is more preferably 10 nm to 300 nm, and still more preferably 20 nm to 250 mm. The transparent optically anisotropic film may be optical uniaxial or biaxial, if these values are in the ranges above. Use of a positive A plate film for optically anisotropic film (B) in combination with a positive C plate film for optically anisotropic film (A) is suitable for improvement in contrast of liquid crystal display devices for IPS, and the positive A plate film (B) preferably has a Re (550 nm) of 40 to 250 nm, more preferably 70 to 230 nm, and still more preferably 100 to 180 nm. Further, the wavelength dispersion $\Delta n(450\ nm)/\Delta n(550\ nm)$ is generally 0.6 to 1.0, preferably 0.65 to 0.95, and more preferably 0.7 to 0.9. $\Delta n(650\ nm)/\Delta n(550\ nm)$ is generally 1.0 to 1.3, preferably 1.01 to 1.25, and more preferably 1.02 to 1.23. The optically anisotropic film (A) preferably has a Re (550 nm) of 0 to 40 nm, more preferably 0 to 20 nm, and still more preferably 0 to 10 nm. Rth (550 nm) is preferably −10 to −300 nm, more preferably −30 to −250 nm, and still more preferably −50 to −200 nm. The wavelength dispersion preferably satisfies the relationships in mathematical formulae (12) and (13). An optical compensation film having a positive A plate film and a positive C plate film for improvement of the contrast of liquid crystal display devices for IPS is described in WO2005/038517, but the wavelength dispersion of the positive C plate is not described therein.

Fundamentally, the materials and shape of the transparent optically anisotropic film are not particularly limited, if it has favorable optical properties as described in the above. For example, use may be made of any one of a retardation film of birefringent polymer film, a film obtained by applying a polymer compound on a transparent support and stretching the film under heat, and a retardation film having a retardation layer formed by applying or transferring a low-molecular-weight or polymer liquid crystal compound onto a transparent support. Alternatively, these films may be used as laminated two or three thereof.

The birefringent polymer film is preferably one excellent in controllability of the birefringent characteristics, and in transparency and heat resistance. In such a case, the polymeric material for use is not particularly limited, if it is a polymer allowing uniform uniaxial or biaxial orientation, but known polymers that are used in solution casting or extrusion to form a target film are preferable; and examples thereof include norbornene-based polymers, polycarbonate-based polymers, polyarylate-based polymers, polyester-based polymers, aromatic polymers such as polysulfone, cellulose acylate, mixed polymers of two or more of these polymers, and the like. Among them, those containing a polycarbonate-based, norbornene-based, or cellulose acylate film are more preferable, from the viewpoints of optical performances such as transparency and uniformity. The method described in the section of the support may be used in preparation of the film.

Biaxial orientation of the film is performed by stretching a thermoplastic resin film, for example, by machine-direction orientation with rolls, transverse-direction orientation with a tenter, or biaxial orientation (by appropriate combination thereof, if necessary), in which the thermoplastic resin film is prepared by a suitable method, such as extrusion forming or casting. The machine-direction orientation with rolls may be performed under suitable heating, such as by using a heating roll, by heating the atmosphere, or by heating in combination thereof. Biaxial orientation in a tenter may be performed by a suitable method, for example, by simultaneous biaxial orientation entirely in a tenter, or by sequential biaxial stretching by a roll/tenter method.

The film is preferably one smaller in orientation irregularity and retardation irregularity. The thickness is determined properly according to the retardation and others, but generally it is preferably 1 to 300 µm, more preferably 10 to 200 µm, and still more preferably 20 to 150 µm, for further reduction of the thickness of film. Stretching is generally performed at a rate such that the length/width after stretched would be 1.01 to 2 times the length/width before subjecting to stretching. The stretching direction may be at least unidirectional; the direction is preferably the mechanical flow direction (extrusion direction) of the resin when the sheet is obtained by extrusion; and a free-shrinkage monoaxial stretching method, a constant-width monoaxial stretching method, a biaxial orientation method, or the like is preferable as the stretching method. The optical properties of the film can be controlled by adjusting the stretching rate and the heating temperature.

<<Low-Re Cellulose Acylate Film>>

The low-optical anisotropy (Re and/or Rth) cellulose acylate film preferably has an in-plane retardation Re at wavelength 630 nm of 10 nm or less ($0 \leq Re(630) \leq 10$) and a retardation Rth in the film thickness direction of −100 nm to 25 µm. More preferably, $0 < Re(630) < 5$, and $-60 < Rth(630) < 20$; and still more preferably, $0 \leq Re(630) \leq 2$, and $-40 \leq Rth(630) \leq 15$.

Further, a cellulose acylate film that is low in its wavelength dispersion is preferable, and more preferably, $|Re(400)-Re(700)| \leq 10$, and $|Rth(400)-Rth(700)| \leq 35$; more preferably, $|Re(400)-Re(700)| \leq 5$, and $|Rth(400)-Rth(700)| \leq 25$; and most preferably, $|Re(400)-Re(700)| \leq 3$, and $|Rth(400)-Rth(700)| \leq 15$.

It is possible to give parts effectively expanding the view angle of a polarizing plate, by lamination of the film with the optically anisotropic film according to the present invention.

Further, use of a laminated low-Re cellulose acylate film as a protection film for polarizing plate is effective in reducing the required thickness of the optically anisotropic film (A) according to the present invention.

The present inventors have found that when the acyl substituent groups substituted to the hydroxyl groups of cellulose described above are substantially at least two kinds of acetyl, propionyl and butanoyl groups, it is possible to reduce the optical anisotropy of the cellulose acylate film at a total substitution degree of 2.50 to 3.00. More preferable degree of acyl substitution is 2.60 to 3.00, and still more preferably 2.65 to 3.00. The raw material cottons and the synthetic methods for these cellulose acylates that can be used in the present invention are described in detail in Kokai-Giho (J. Technical Disclosure), Japan Institute of Invention and Innovation (Kogi (JTD) No. 2001-1745, published on Mar. 15, 2001, Japan Institute of Invention and Innovation), pages 7 to 12.

The cellulose acylates may be used singly or in combination of two or more different kinds thereof, if it or they have the above substituent group, substitution degree, polymerization degree, molecular weight distribution, and others, as described in the above.

To the cellulose acylate solution (dope), any of various additives may be added, which is suitable for the target application in each preparative step (e.g., optical anisotropy-decreasing compound, wavelength dispersion adjusting agent, ultraviolet ray inhibitor (absorber), plasticizer, degradation inhibitor, fine particles, optical properties adjusting agent, and others), and such additives are described below. These additives may be added in any timing or step of dope preparation, and the additive(s) may be added in the last phase of preparing the dope to thereby complete the preparation of the dope.

The cellulose acylate film that can be used in the present invention preferably contains a compound that decreases the Rth in the film thickness direction into the range for satisfying the relationships in mathematical formulae (III) and (IV):

$$(Rth_{(A)} - Rth_{(O)})/A \leq -1.0$$

$$0.01 \leq A \leq 30 \qquad \text{Mathematical formula (IV)}$$

In mathematical formulae (III) and (IV), Rth(A) represents Rth (nm) of the protection film containing the compound lowering Rth in an amount of A %; $Rth_{(O)}$ represents Rth (nm) of the protection film containing no compound lowering Rth; and A represents the mass (%) of the compound lowering Rth, assuming that the mass of the film raw material polymer to be 100.

The mathematical formulae (III) and (IV) more preferably satisfy mathematical formulae (III-I) and (IV-I), respectively:

$$(Rth_{(A)} - R_{th(O)})/A \leq -2.0 \qquad \text{Mathematical formula (III-I)}$$

$$0.1 \leq A \leq 20 \qquad \text{Mathematical formula (IV-I)}$$

Hereinafter, the compound for lowering optical anisotropy of the cellulose acylate film will be described, which is also referred to as 'optical anisotropy-decreasing compound'. After intensive studies, the inventors of the present invention made Re zero and Rth close to zero, by lowering the optical anisotropy sufficiently, using a compound controlling orientation of the cellulose acylate in film in the in-plane direction and in the film-thickness direction. For that purpose, it is advantageous to use the compound for lowering optical anisotropy is compatible with the cellulose acylate sufficiently, and the compound itself does not have a rod-shaped or planar structure. Specifically, if the compound has planar functional groups such as aromatic groups, a structure containing these functional groups not on the same plane but in a non-plane manner is advantageous.

In preparation of the cellulose acylate film that can be used in the present invention, as described above, among the compounds for controlling orientation of the cellulose acylate in film in the in-plane direction and in the film-thickness direction thereby to lower the optical anisotropy, use may be preferable made of a compound having an octanol-water distribution coefficient (logP value) of 0 to 7. Use of a compound having a logP value of 7 or less can make the compound more compatible with the cellulose acylate better, and thus prevents whitening and powder deposition in the film more effectively. Further, use of a compound having a logP value of 0 or more, which is more hydrophilic, can prevent deterioration in water resistance of the cellulose acetate film more effectively. The logP value is more preferably in the range of 1 to 6, and particularly preferably in the range of 1.5 to 5.

The octanol-water distribution coefficient (logP value) may be measured by a flask shaking method as described in Japanese Industrial Standards (JIS) Z7260-107 (2000). Alternatively, in place of actual measurement, the octanol-water distribution coefficient (logP value) may be estimated by a computational chemical method or an empirical method. Preferable examples of the computation that can be used include Crippen's fragmentation method (J. Chem. Inf. Comput. Sci., 27, 21 (1987)), Viswanadhan's fragmentation method (J. Chem. Inf. Comput. Sci., 29, 163 (1989)), and Broto's fragmentation method (Eur. J. Med, Chem.-Chim. Theor., 19, 71 (1984)); and among them, Crippen's fragmentation method (J. Chem. Inf. Comput. Sci., 27, 21 (1987)) is more preferable. If a compound has different logP values according to the methods of measurement or computation, it is preferable to apply the Crippen's fragmentation method to determine whether the compound in interest is within the preferable range as specified in the present invention or not.

The compound for lowering optical anisotropy may have an aromatic group, or no aromatic group. The molecular weight of the compound for lowering optical anisotropy is preferably 150 to 3,000, more preferably 170 to 2,000, and further preferably 200 to 1,000. The compound for lowering optical anisotropy may have a specific monomer structure, or an oligomer structure or polymer structure in which a plurality of the monomer units are combined together, as long as it has a molecular weight in the above-described preferable range.

The compound for lowering optical anisotropy is preferably liquid at 25° C., or solid having a melting point of 25 to 250° C., and it is more preferably liquid at 25° C. or solid having a melting point of 25 to 200° C. The compound for lowering optical anisotropy is preferably not volatilized in the course of dope casting and drying steps in the preparation of the cellulose acylate compound film.

The amount to be added of the compound for lowering optical anisotropy is preferably 0.01 to 30% by mass, more preferably 1 to 25% by mass, and particularly preferably 5 to 20% by mass, to the cellulose acyrate.

The compound for lowering optical anisotropy may be used singly, or in combination of two or more kinds of the compounds mixed at an arbitrary ratio.

The compound for lowering optical anisotropy may be added at any time during the dope making process, and may be added at the end of the dope making step.

The compound for lowering optical anisotropy is preferably contained in the film in such a manner that the average content of the compound in the region from at least one surface to a depth of 10% of the entire film thickness is 80 to 99% of the average content of the compound in the central region of the cellulose acylate film. The amount of the compound for lowering optical anisotropy can be determined, for example, by measuring the contents of the compound in the surface and central regions by the method of using infrared absorption spectra, as described in JP-A-8-57879.

Hereinafter, specific examples of the compound, which can be preferably used in the present invention, for lowering optical anisotropy of a cellulose acylate film, will be shown, but it should be understood that the present invention is not limited to those compounds.

Examples of the compound for lowering optical anisotropy include compounds represented by formula (3) or (4).

[Chemical formula 24]

Formula (3)

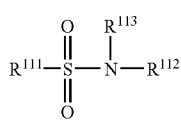

In formula (3), $R^{111}$ represents an alkyl group or an aryl group; and $R^{112}$ and $R^{113}$ each independently represent a hydrogen atom, an alkyl group, or an aryl group. The total sum of the number of carbon atoms of $R^{111}$, $R^{112}$ and $R^{113}$ is particularly preferably 10 or more. $R^{111}$, $R^{112}$ and $R^{113}$ may have a substituent; and preferable examples of the substituent include a fluorine atom, an alkyl group, an aryl group, an alkoxy group, a sulfone group, a sulfonamido group, and a cyano group; and particularly preferably an alkyl group, an aryl group, an alkoxy group, a sulfone group, and a sulfonamido group. The alkyl group may be a straight-chain, branched or cyclic alkyl group, and it preferably has 1 to 25 carbon atoms, more preferably 6 to 25 carbon atoms, and particularly preferably 6 to 20 carbon atoms (e.g., methyl, ethyl, propyl, isopropyl, butyl, isobutyl, tert-butyl, amyl, isoamyl, tert-amyl, hexyl, cyclohexyl, heptyl, octyl, bicyclooctyl, nonyl, adamantyl, decyl, tert-octyl, undecyl, dodecyl, tridecyl, tetradecyl, pentadecyl, hexadecyl, heptadecyl, octadecyl, nonadecyl, and didecyl). The aryl group is preferably an aryl group having 6 to 30 carbon atoms, particularly preferably 6 to 24 carbon atoms (e.g., phenyl, biphenyl, terphenyl, naphthyl, binaphtyl, or triphenylphenyl).

[Chemical formula 25]

[Chemical formula 25]

Formula (4)

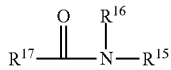

In formula (4), $R^{17}$ represents an alkyl group or an aryl group; and $R^{15}$ and $R^{16}$ each independently represent a hydrogen atom, an alkyl group, or an aryl group.

$R^{17}$ is preferably a phenyl group or a cyclic alkyl group. $R^{15}$ and $R^{16}$ each are preferably a phenyl group or an alkyl group. The alkyl group is preferably a cyclic or straight-chain alkyl group.

These groups may have at least one substituent; preferable examples of the substituent include a fluorine atom, an alkyl group, an aryl group, an alkoxy group, a sulfone group, and a sulfonamido group; and particularly preferably an alkyl group, an aryl group, an alkoxy group, a sulfone group, and a sulfonamido group.

The compound represented by formula (4) is more preferably a compound represented by formula (5).

[Chemical formula 26]

[Chemical formula 26]

Formula (5)

In formula (5), $R^{114}$, $R^{115}$ and $R^{116}$ each independently represent an alkyl group or an aryl group. The alkyl group is preferably a cyclic or straight-chain alkyl group. The aryl group is preferably a phenyl group.

Preferred examples of the compound represented by formula (3) are shown below, but the present invention is not meant to be limited to those. Here, in the present specification, "Pr$^i$" means an isopropyl group.

[Chemical formula 27]

A-1

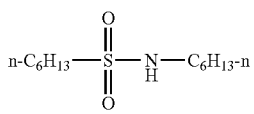

A-2

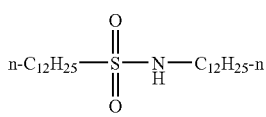

A-3

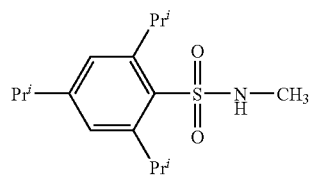

A-4

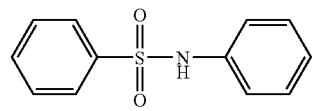

A-5

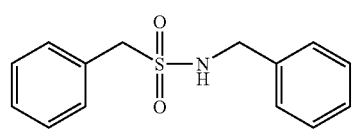

A-6

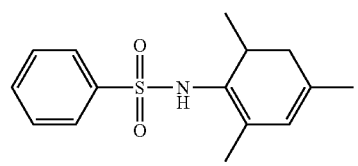

A-7

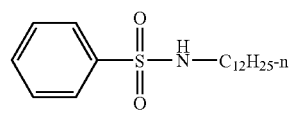

A-8

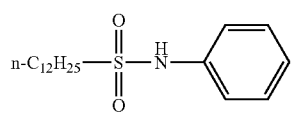

A-9

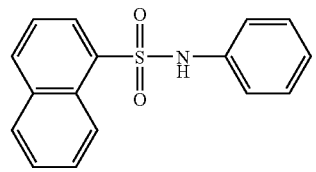

A-10

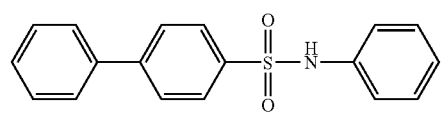

A-11

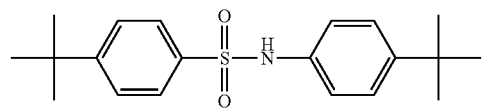

A-12

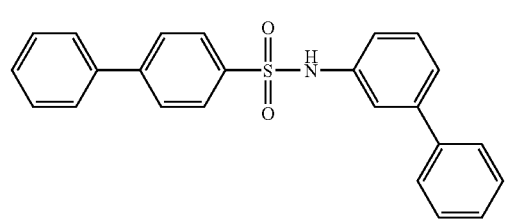

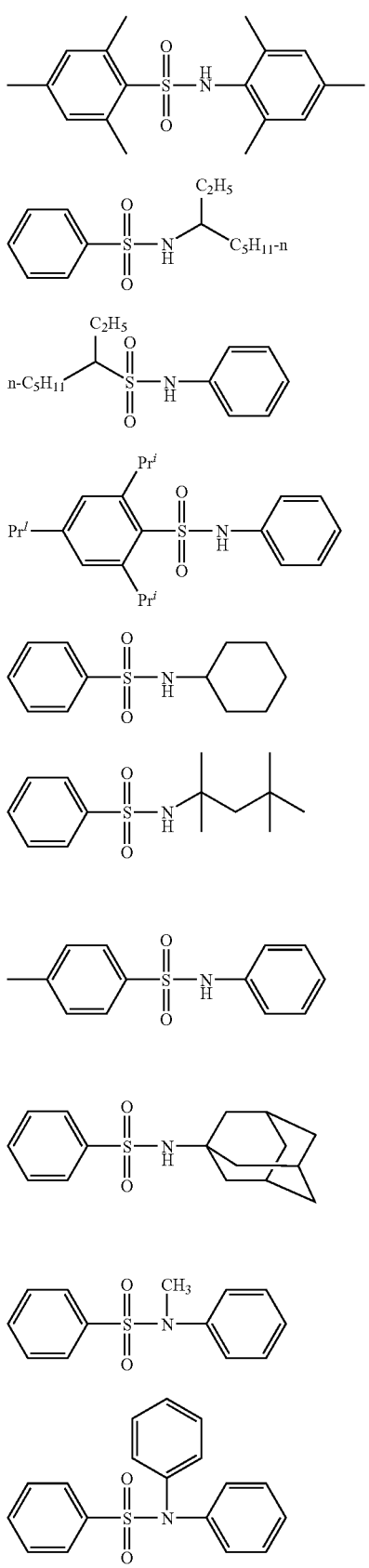
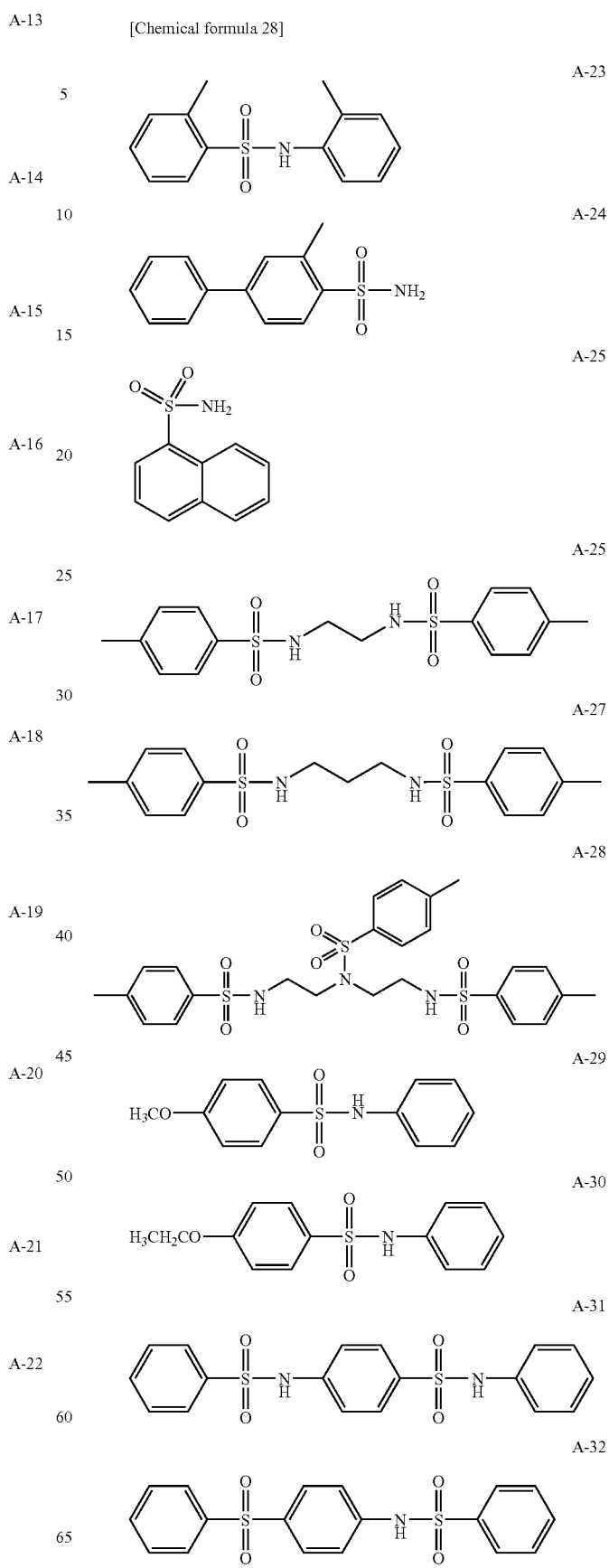

A-33 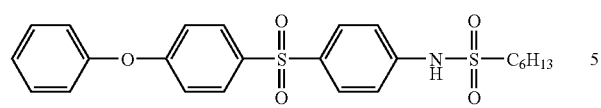
A-34 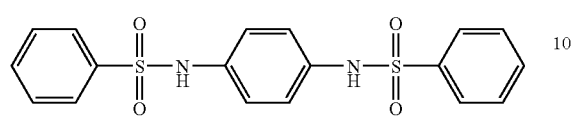
A-35 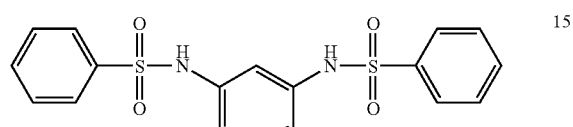
A-36 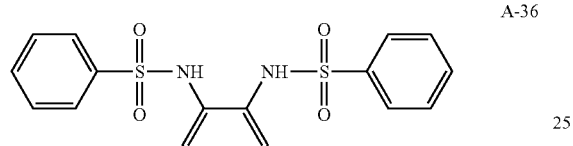
A-37 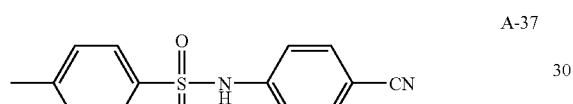
A-38 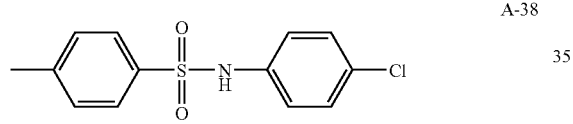
A-39 
[Chemical formula 29]
A-40 
A-41 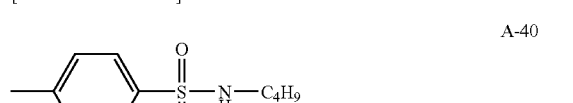
A-42 
A-43 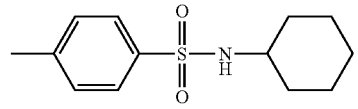
A-44 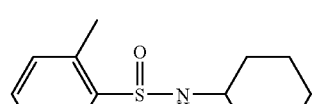
A-45 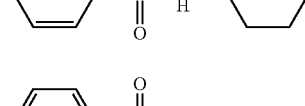
A-46 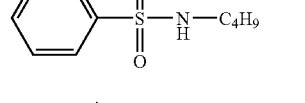
A-47 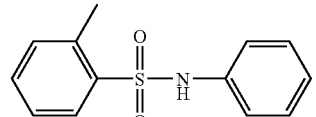
A-48 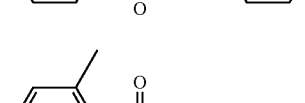
A-49 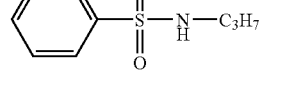
A-50 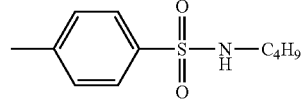
A-51 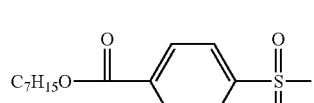
Preferred examples of the compound represented by formula (4) or (5) are shown below, but the present invention is not meant to be limited to those. Here, in the present specification, "Bu$^i$" means an isobutyl group.
[Chemical formula 30]
FA-1 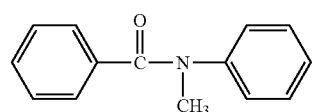

FA-2
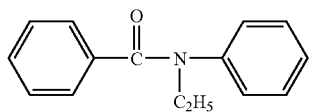
FA-3
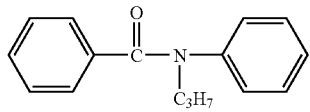
FA-4
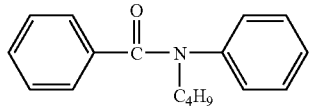
FA-5
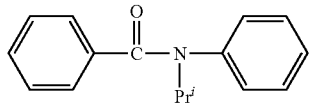
FA-6
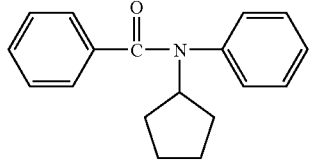
FA-7
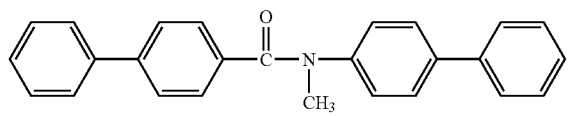
FA-8
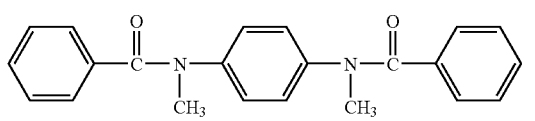
FA-9
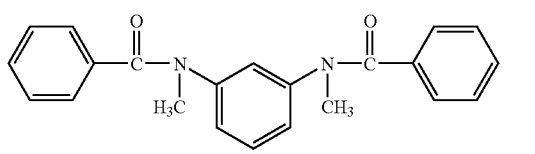
FA-10
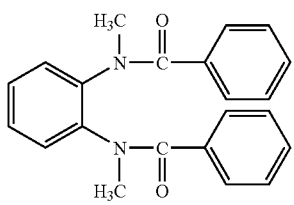
FA-11
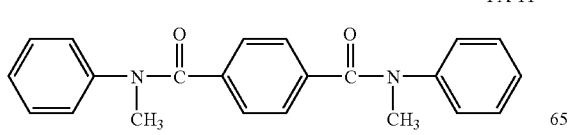
FA-12
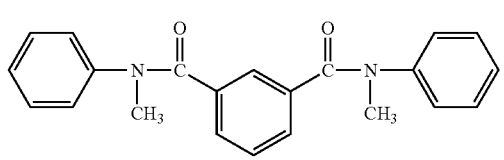
FA-13
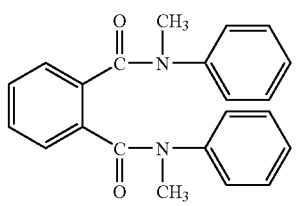
FA-14
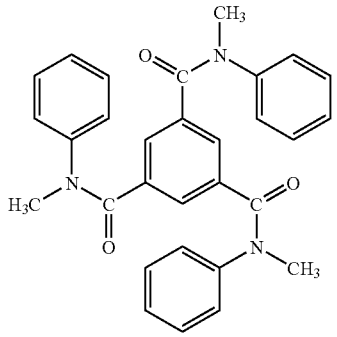
FA-15
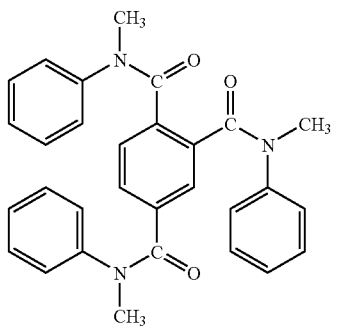
FA-16
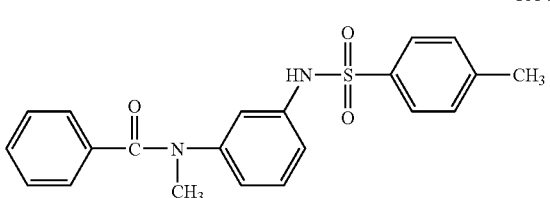
FA-17
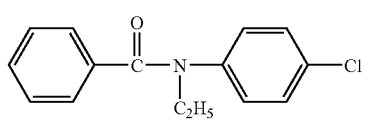
[Chemical formula 31]
FA-18
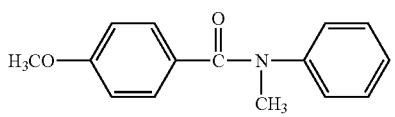

FA-19
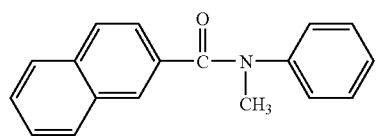
FA-20
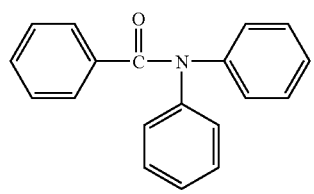
FA-21
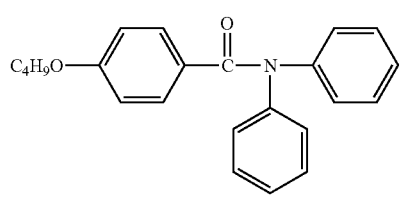
FA-22
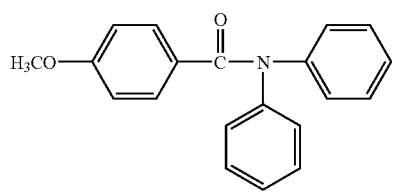
FA-23
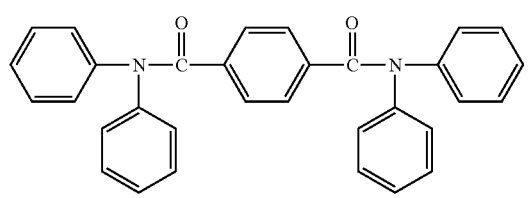
FA-24
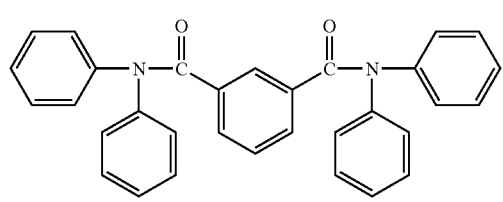
FA-25
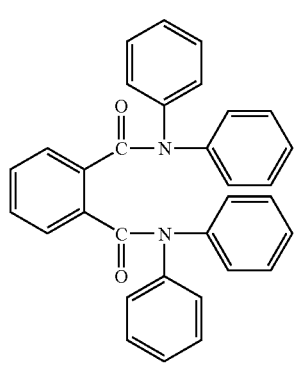
FA-26
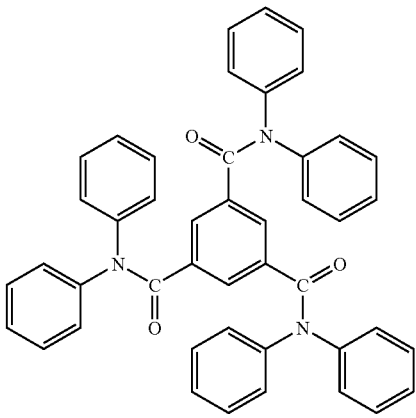
FA-27
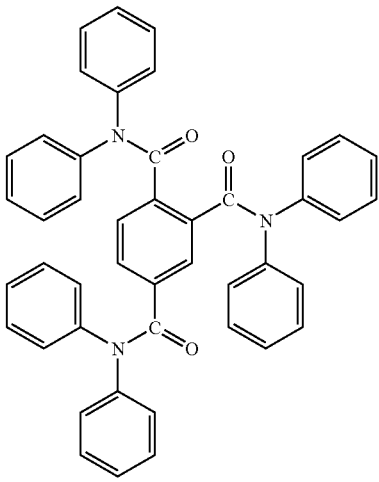
FA-28
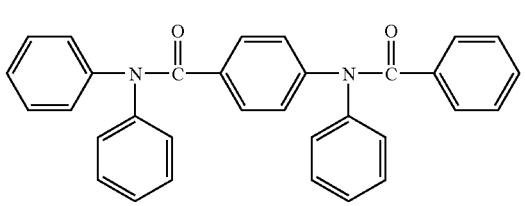
[Chemical formula 32]
FB-1
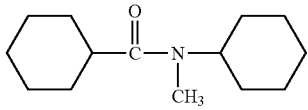
FB-2
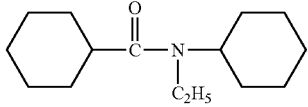
FB-3
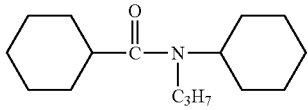

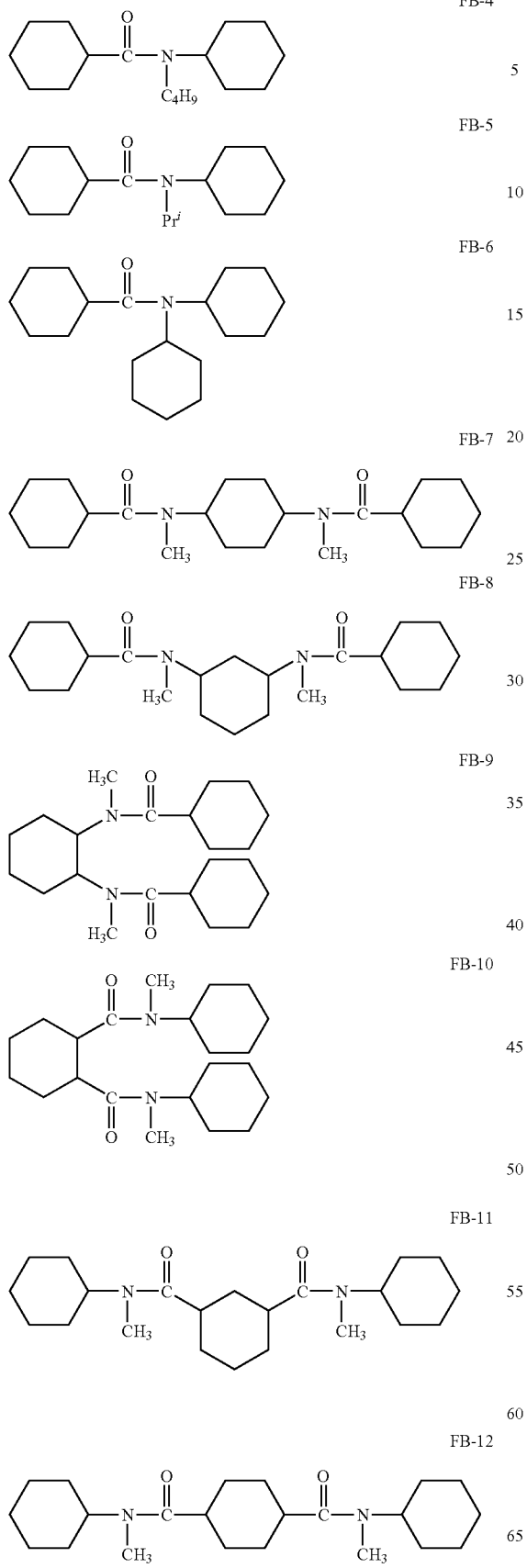
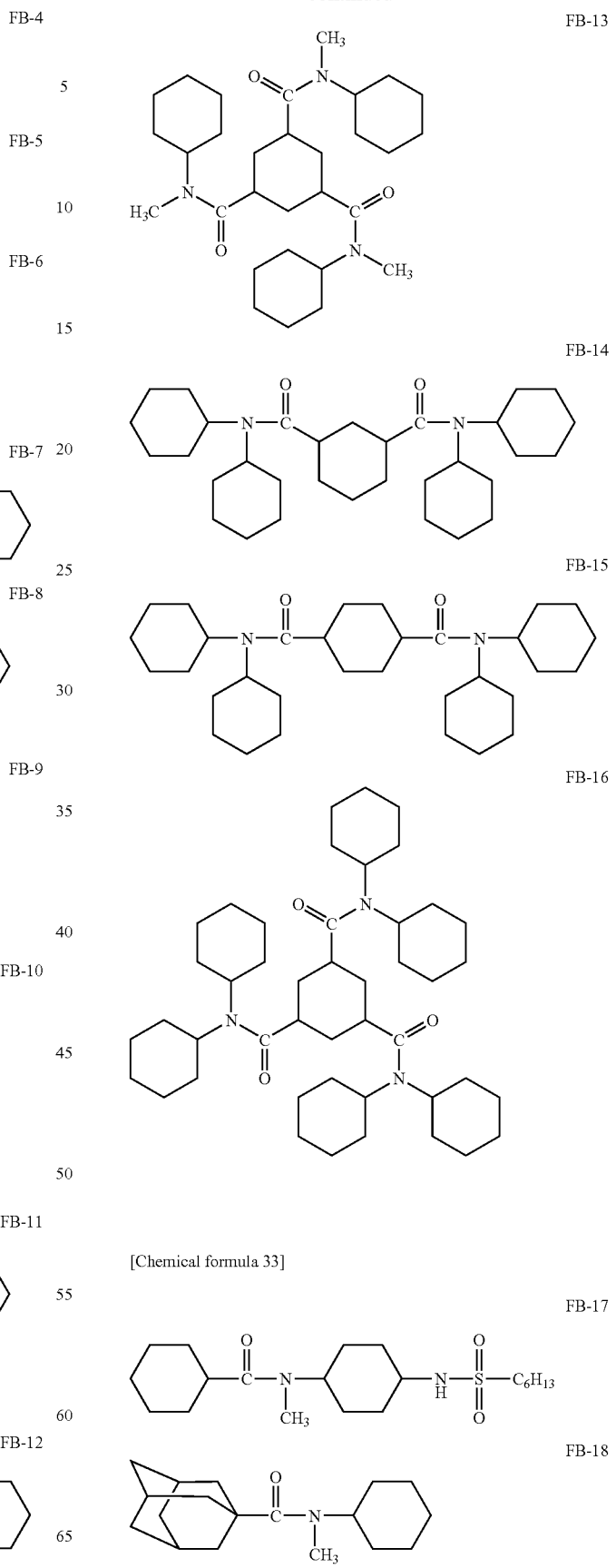

FB-19 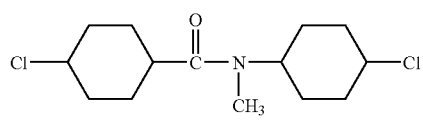
FB-20 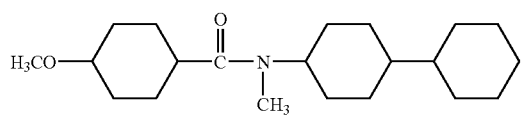
FB-21 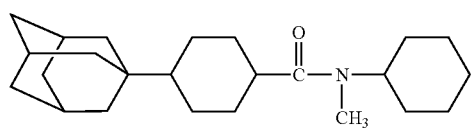
FB-22 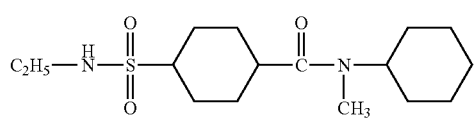
FB-23 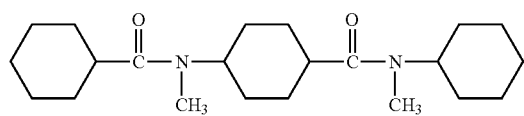
FB-24 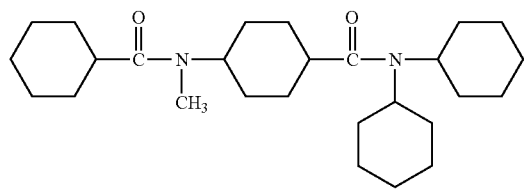
[Chemical formula 34]
FC-1 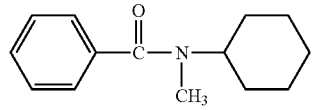
FC-2 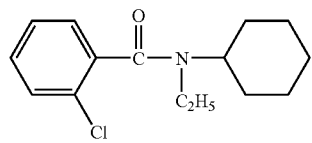
FC-3 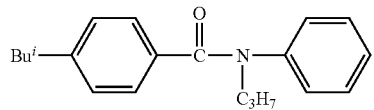
FC-4 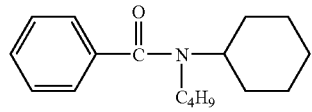
FC-5 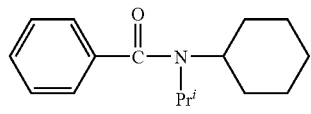
FC-6 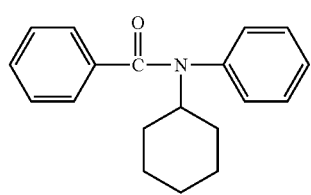
FC-7 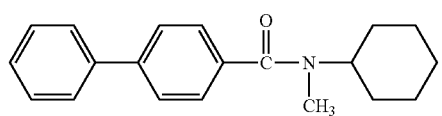
FC-8 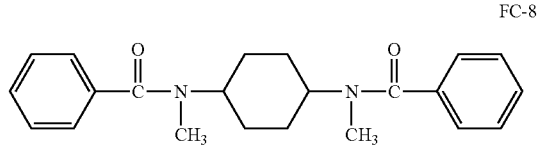
FC-9 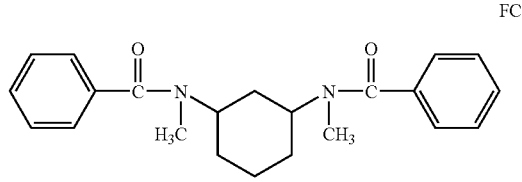
FC-10 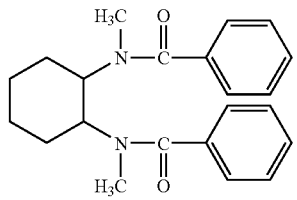
FC-11 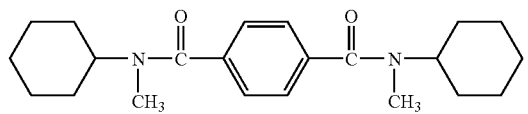
FC-12 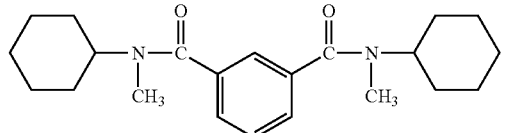
FC-13 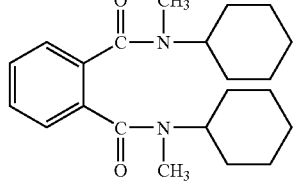

FC-14
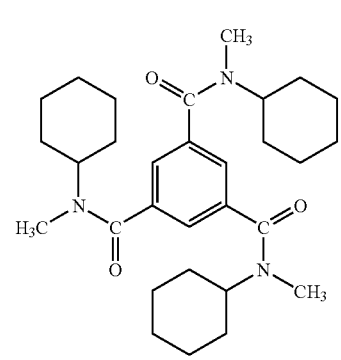
FC-15
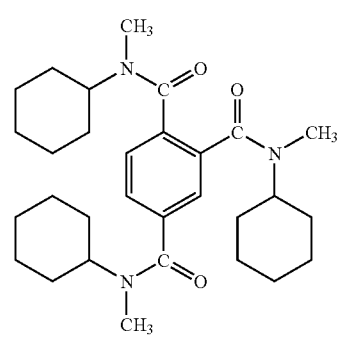
FC-16
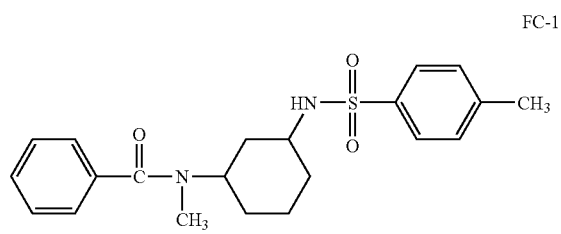
FC-17
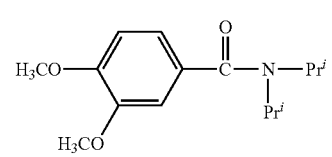
[Chemical formula 35]
FC-18
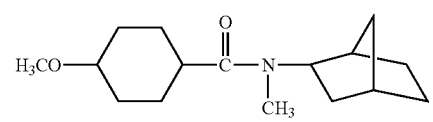
FC-19
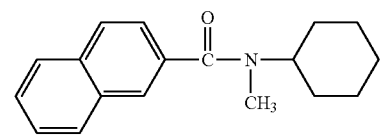
FC-20
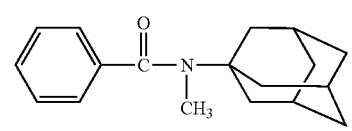
FC-21
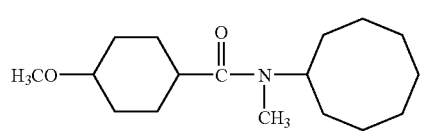
FC-22
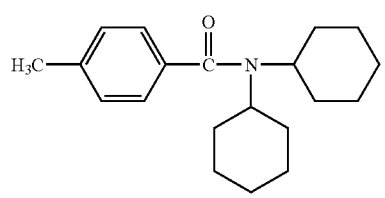
FC-23
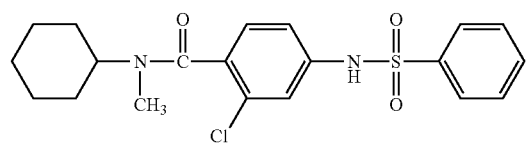
FC-24
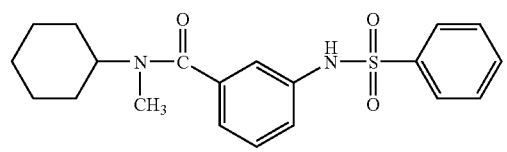
FC-25
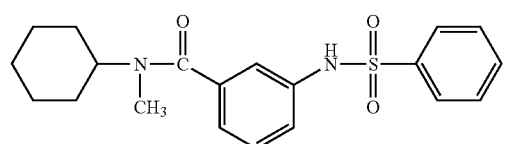
[Chemical formula 36]
FD-1
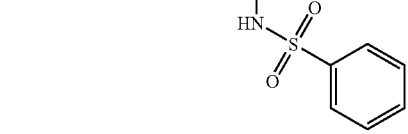
FD-2
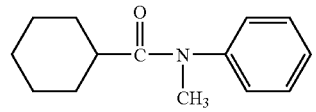
FD-3
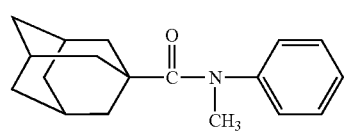
FD-4
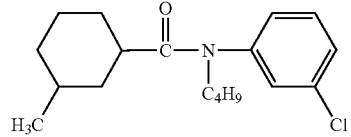

FD-5
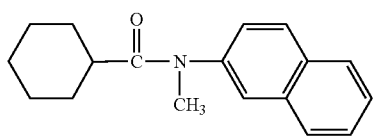
FD-6
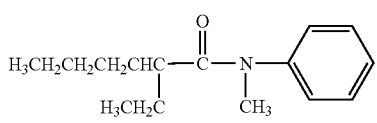
FD-7
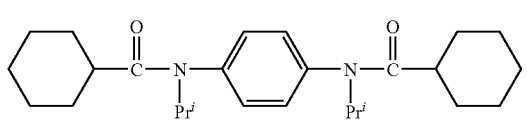
FD-8
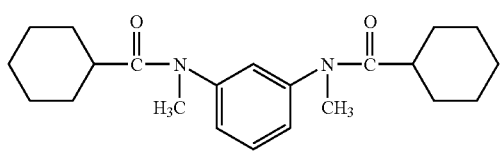
FD-9
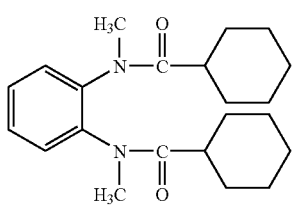
FD-10
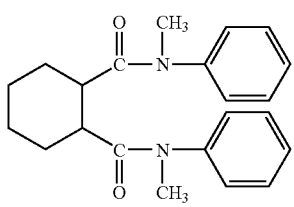
FD-11
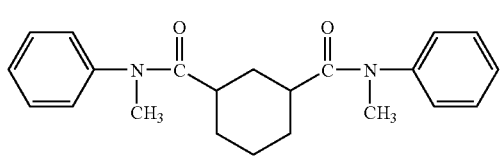
FD-12
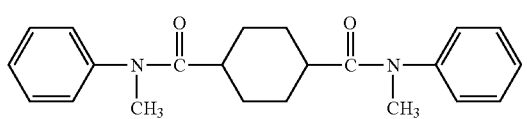
FD-13
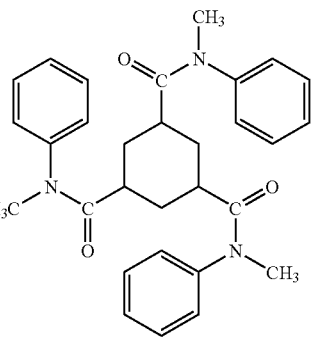
[Chemical formula 37]
FD-14
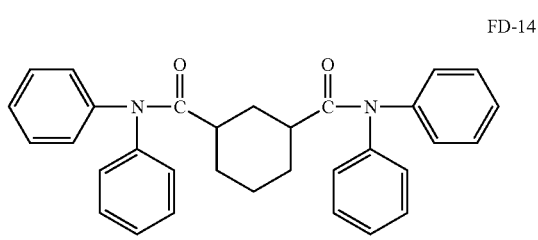
FD-15
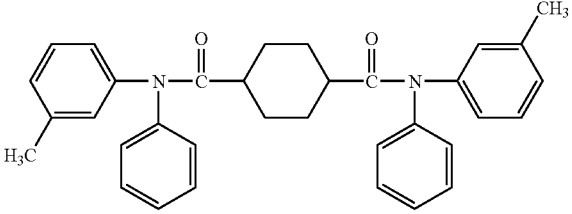
FD-16
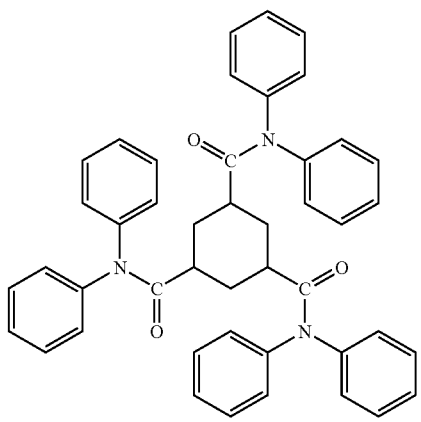
FD-17
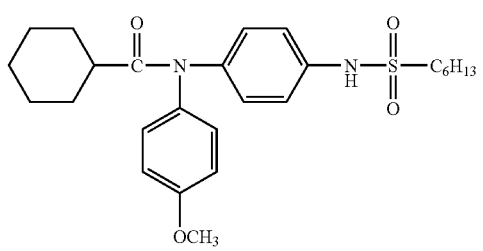

FD-18

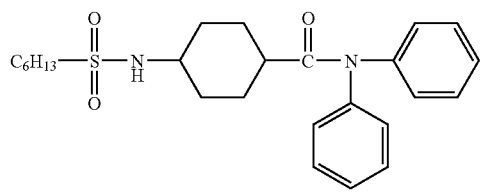

FD-19

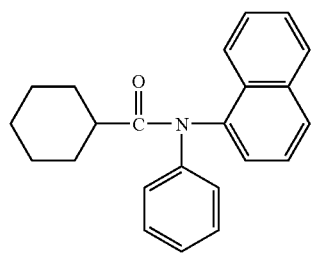

FD-20

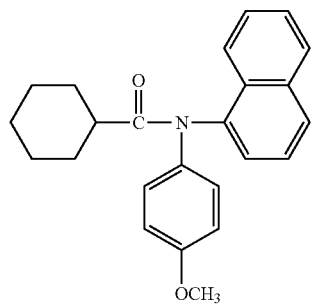

FD-21

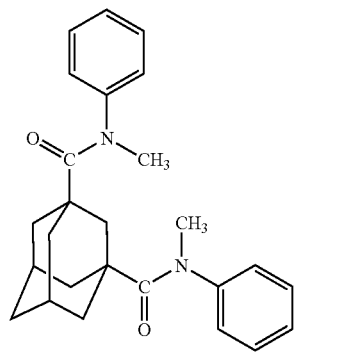

FD-22

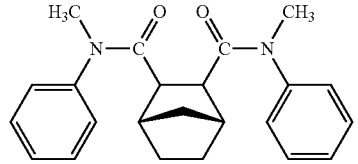

The methods described above regarding the preparation of a support are applicable as the method of lowering Rth further and making it negative.

[Image Display Device of the Present Invention]

It is possible to provide a liquid crystal display device with a widened view angle, by using the optically anisotropic film (A) according to the present invention and a laminate optical film. The retardation sheet (optical compensation sheet) for liquid crystal cell of TN mode is described, for example, in JP-A-6-214116, U.S. Pat. No. 5,583,679, U.S. Pat. No. 5,646,703, and DB 39 11 620A1. The retardation sheet (optical compensatory sheet) for liquid crystal cell of IPS or FLC mode is described, for example, in JP-A-10-54982. The retardation sheet (optical compensatory sheet) for liquid crystal cell of OCB or HAN mode is described, for example, in U.S. Pat. No. 5,805,253 and WO96/37804. The retardation sheet (optical compensatory sheet) for liquid crystal cell of STN mode is described, for example, in JP-A-9-26572. The retardation sheet (optical compensatory sheet) for liquid crystal cell of VA mode is described, for example, in Japanese Patent No. 2,866,372.

Further, use of the optically anisotropic film and the laminate optical film according to the present invention in combination with a polarizing plate is effective for the antireflective purpose, fro example, of electroluminescence devices and field emission display devices.

In the present invention, retardation sheets (optical compensation sheets) for liquid crystal cells in various modes can be prepared, with reference to the publications mentioned in the above. The retardation sheet of the present invention can be used in liquid crystal display devices of various display modes, for example, of TN, IPS, FLC, OCB, STN, VA, and HAN.

The optically anisotropic films (A) and (B) according to the present invention each may be used as a support or a smoothing layer. The optically anisotropic films (A) and (B) in combination are effective as an optical compensation film for IPS, and in such a case, the optically anisotropic films (A) and (B) may be disposed inside or outside the liquid crystal cell, alternatively one of them may be disposed inside and the other outside.

The optically anisotropic film obtained by orientating the liquid crystal compound of the present invention almost in the horizontal direction and then immobilizing the thus-oriented compound, may be used as a compensation film for liquid crystal display devices, such as VA liquid crystal, similarly to the reverse dispersion positive A plate, as described, for example, in JP-A-2004-326089. Further, the reverse dispersion positive A plate described in JP-A-2004-326089 employs a stretched polymer film of thickness 50 to 80 μm, but the reverse dispersion positive A plate according to the present invention can give the target optical properties with film thickness of approximately 3 μm, and thus the present invention allows reduction in thickness of the film.

[Liquid Crystal Display Device]
<Constitution of Common Liquid Crystal Display Device>

The optical film containing the liquid crystal compound of the present invention may be applied to liquid crystal display devices. A liquid crystal display device has, for example, a constitution of a liquid crystal cell carrying liquid crystal between two pieces of electrode substrates, two polarizing films one of which is disposed on one surface of the liquid crystal cell and the other on the other surface, and at least one optical compensation film disposed between the liquid crystal cell and the polarizing film.

The liquid crystal layer of the liquid crystal cell can be formed generally, by sealing a liquid crystal, in the space made by putting a spacer sandwiched between two pieces of substrates. The transparent electrode layer can be formed on the substrate as a transparent film containing an electric conductive substance. To the liquid crystal cell, for example, a gas barrier layer, a hard coat layer, or an undercoat (or subbing) layer (used for adhesion of the transparent electrode layer) may be further provided. The aforementioned layers can be provided, generally, on the substrate. It is preferable that the thickness of the substrate for the liquid crystal cell is generally from 50 μm to 2 mm.

<Kinds of Liquid Crystal Display Device>

The optical film containing the liquid crystal compound of the present invention may be used in liquid crystal cells driven in various displaying modes. Examples of the display mode include: TN (Twisted Nematic), IPS (In-Plane Switching), FLC (Ferroelectric Liquid Crystal), AFLC (Anti-ferroelectric Liquid Crystal), OCB (Optically Compensatory Bend), STN (Supper Twisted Nematic), VA (Vertically Aligned), ECB (Electrically Controlled Birefringence), and HAN (Hybrid Aligned Nematic). Further, such an optical film according to the present invention may also be used in display modes that are obtained by orientation dividing of the aforementioned display modes.

(TN-Type Liquid Crystal Display Device)

The Optical Film Containing the Liquid Crystal Compound of the Present invention can be used as a support for an optical compensation sheet that is used in TN type liquid crystal display devices having a liquid crystal cell of TN mode. The TN mode liquid crystal cell and the TN-type liquid crystal display device per se are well known for a long time. The optical compensation sheet that is used in TN-type liquid crystal display devices can be prepared in accordance with, for example, JP-A-3-9325, JP-A-6-148429, JP-A-8-50206, and JP-A-9-26572, or can also be prepared in accordance with, for example, papers authored by Mori, et al. (Jpn. J. Appl. Phys., Vol. 36 (1997), p. 143, and Jpn. J. Appl. Phys., Vol. 36 (1997), p. 1068).

(STN-Type Liquid Crystal Display Device)

The Optical Film Containing the Liquid Crystal Compound of the Present invention may be used as a support for an optical compensation sheet that is employed in STN-type liquid crystal display devices installing a STN mode liquid crystal cell. In STN-type liquid crystal display devices, generally, cylindrical-shape liquid-crystalline (mesomorphism) molecules in the liquid crystal cell is twisted in the range of 90 to 360 degrees, and the product (Δnd) of a refractive index anisotropy (Δn) of the cylindrical-shape mesomorphism molecule and a cell gap (d) is in the range of 300 to 1,500 nm. The optical compensation sheets for use in the STN type liquid crystal display devices can be prepared in accordance with, for example, JP-A-2000-105316.

(VA-Type Liquid Crystal Display Device)

The Optical Film Containing the Liquid Crystal Compound of the Present invention can be particularly advantageously used as a support for an optical compensation sheet that is used in the VA-type liquid crystal display devices installing a VA mode liquid crystal cell. It is preferred that the Re value is controlled to the range from 0 to 150 nm and the Rth value is controlled to the range from 70 to 400 nm, respectively, for the optical compensation sheet that is used in the VA-type liquid crystal display device. In an embodiment where two sheets of optically anisotropic polymer films are used in a VA-type liquid crystal display device, it is preferred that the Rth value of the film is in the range from 70 to 250 nm. In an embodiment where one sheet of an optically anisotropic polymer film is used in a VA-type liquid crystal display device, it is preferred that the Rth value of the film is in the range from 150 to 400 nm. The VA-type liquid crystal display device may have an orientation dividing system, as described in, for example, JP-A-10-123576.

(IPS-Type Liquid Crystal Display Device and ECB-Type Liquid Crystal Display Device)

The optical film containing the liquid crystal compound of the present invention may also be advantageously used as the support for the optical compensation sheet or as the protective film of the polarizing plate, in an IPS-type liquid crystal display device or ECB-type liquid crystal display device in which an IPS-mode or ECB-mode liquid crystal cell is assembled, respectively. In these modes, a mesomorphism (liquid crystal) material is oriented almost in parallel when a black color is displayed, and a mesomorphism molecule is oriented in parallel to the surface of the substrate in the condition that no voltage is applied, to display a black color. In these modes, the polarizing plate using the cellulose film of the present invention contributes to improvement in color hue, expansion of the angle of field of view, and improvement in contrast. In these modes, it is preferable that use is made of, for at least one side of the two polarizing plates, the optical film (as a protective film) of the present invention for the protective film (a cell-side protective film) disposed between the liquid crystal cell and the polarizing plate, of the protective films of the two polarizing plates on the upper and lower sides of the liquid crystal cell. It is more preferable that an optical anisotropic layer be disposed between the protective film of the polarizing plate and the liquid crystal cell, and that the retardation value of the disposed optical anisotropic layer be set to a value not more than twice the value of Δn·d of the liquid crystal layer.

(OCB-Type Liquid Crystal Display Device and HAN-Type Liquid Crystal Display Device)

The optical film containing the liquid crystal compound of the present invention can also be advantageously used as a support for an optical compensation sheet that is used in an OCB-type liquid crystal display device having a liquid crystal cell of OCB mode, or used in a HAN-type liquid crystal display device having a liquid crystal cell of HAN mode. It is preferable that, in the optical compensation sheet used for an OCB-type liquid crystal display device or a HAN-type liquid crystal display device, the direction where the magnitude or absolute value of retardation becomes the minimum value exists neither in the optical compensation sheet plane nor in its normal direction. Optical properties of the optical compensation sheet for use in the OCB type liquid crystal display device or the HAN type liquid crystal display device are also determined by the optical properties of the optical anisotropy layer, by the optical properties of the support, and by the arrangement of the optical anisotropy layer and the support. The optical compensation sheet for use in the OCB type liquid crystal display device or HAN type liquid crystal display device can be prepared in accordance with, for example, JP-A-9-197397, or can also be prepared in accordance with, for example, a paper by Mori et al. (Jpn. J. Appl. Phys., Vol. 38 (1999), p. 2837).

(Reflection Type Liquid Crystal Display Device)

The optical film containing the liquid crystal compound of the present invention can also be advantageously used as an optical compensation sheet for the reflection-type liquid crystal display devices of TN-type, STN-type, HAN-type, or GH (Guest-host)-type. These display modes are well known for a long time. The TN-type reflection-type liquid crystal display devices can be prepared in accordance with, for example, JP-A-10-123478, WO 98/48320, and Japanese Patent No. 3022477. The optical compensation sheet for use in a reflection type liquid crystal display device can be prepared in accordance with, for example, WO 00/65384.

(Other Liquid Crystal Display Devices)

The optical film containing the liquid crystal compound of the present invention can also be advantageously used as a support for an optical compensation sheet for use in ASM (Axially Symmetric Aligned Microcell) type liquid crystal display devices having a liquid crystal cell of ASM mode. The liquid crystal cell of ASM mode is characterized in that a resin spacer adjustable with its position maintains the thickness of the cell. Other properties of the liquid crystal cell of ASM mode are similar to the properties of the liquid crystal cell of TN mode. The liquid crystal cells of ASM mode and ASM type liquid crystal display devices can be prepared in accordance with, for example, a paper of Kume et al. (Kume et al., SID 98 Digest, P. 1089 (1998)).

The liquid crystal compound of the present invention can provide a film (i.e. an optical film) with reverse wavelength dispersion, upon applied, oriented and then immobilized on an oriented film. Further, the optical film of the present invention containing the liquid crystal compound shows reverse wavelength dispersion, and the retardation sheet comprising the optical film can be applied favorably to liquid crystal display devices.

The present invention will be described in more detail based on the following examples. The materials, the amounts to be used, the proportions, the contents and procedures of treatment or processing, which will be shown in the examples, may be appropriately changed or modified, without departing from the spirit of the present invention. Therefore, the following examples are not interpreted as limiting of the scope of the present invention.

EXAMPLES

Example 1

Preparation of Exemplified Compound (2)

The Exemplified compound (2) was prepared, in accordance with the following scheme:

[Chemical formula 38]

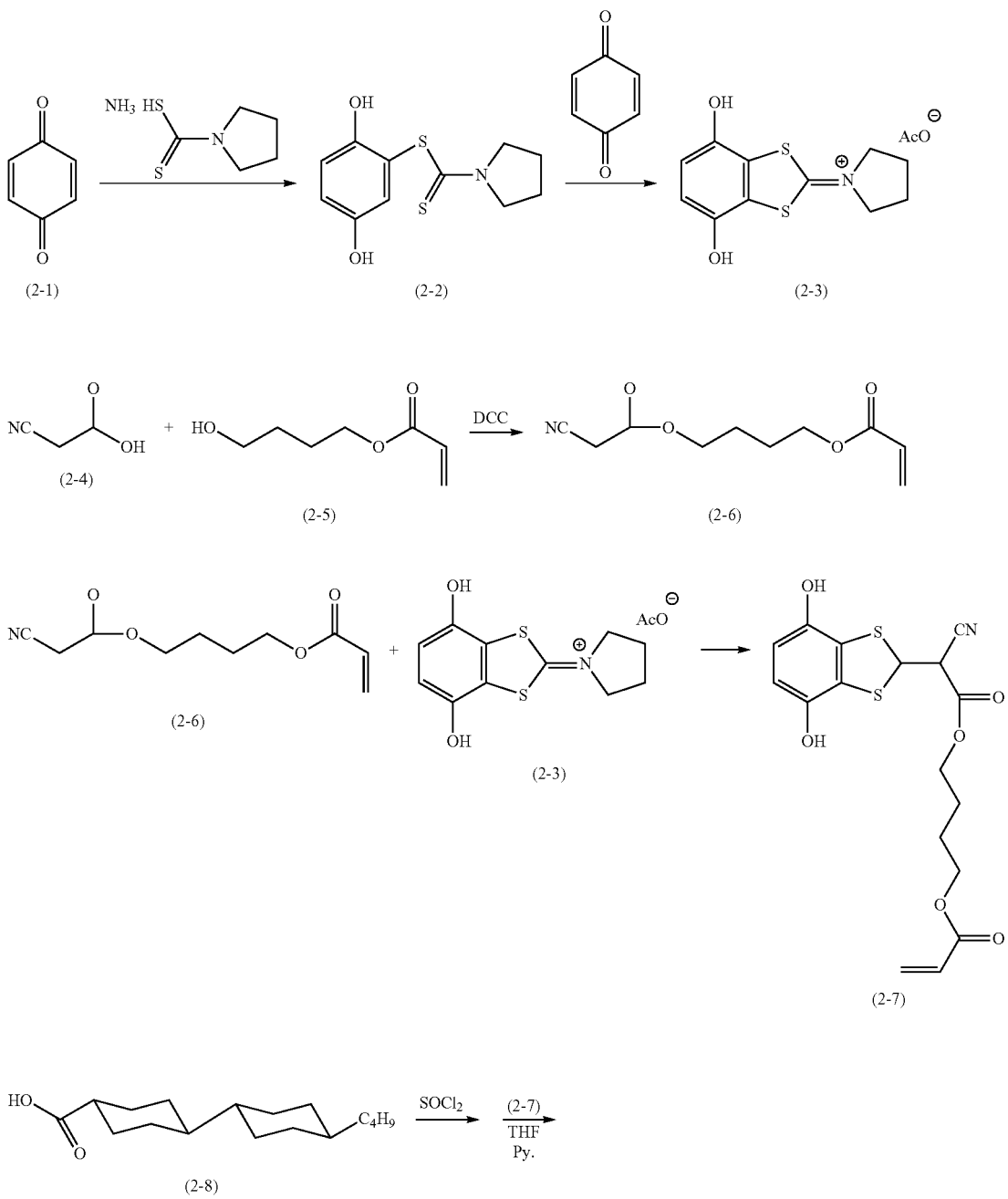

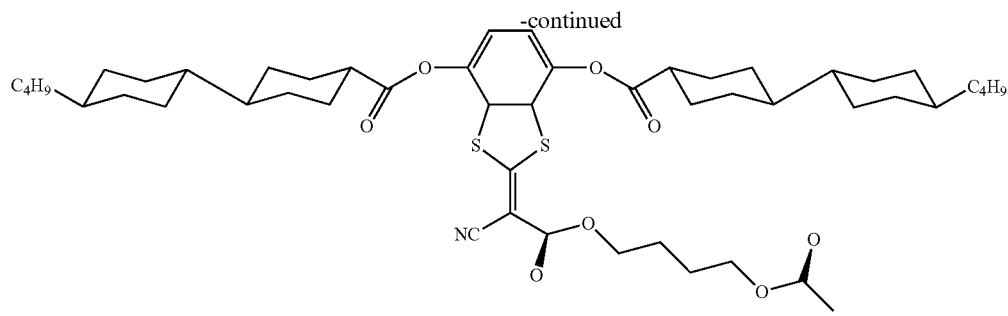

Exemplified compound (2)

The synthesis of each of Compounds (2-1) to (2-3) was carried out in reference to the methods described in "Journal of Chemical Crystallography" (1997), 27(9), p. 515-526.

To 50 ml of a tetrahydrofuran solution of 8.5 g (0.1 mol) of cyanoacetic acid (2-4) and 14.4 g (0.1 mol) of 4-hydroxybutyl acrylate (2-5), 20.6 g (0.1 mol) of dicyclohexylcarbodiimide (DCC) was added dropwise under cooling on ice. The resultant mixture was warmed to room temperature and stirred at the same temperature for 2 hours, and the resultant solid matter was removed by filtration. The solvent in the filtrate was removed off by distillation under reduced pressure, and the resultant solid matter was removed by filtration, to give 18.6 g of Compound (2-6) (yield: 88 mol %).

A suspension of 15.7 g (50 mmol) of Compound (2-3), 12.7 g (60 mmol) of Compound (2-6), and 50 mg of Irganox 1010 (trade name, manufactured by Ciba Specialty Chemicals) in 100 ml of N-methyl-2-pyrrolidohe (NMP) was heated to 80° C. under nitrogen atmosphere. After the suspension became homogeneous, it was stirred additionally for 1.5 hours and then cooled. After addition of ethyl acetate and water thereto, the mixture was separated, and the organic layer was washed with water, 0.5N aqueous hydrochloric acid, and water, in that order. The thus-washed organic layer was dried over magnesium sulfate, and the solvent was removed off by distillation under reduced pressure. Purification by silica gel column chromatography gave 12.8 g of Compound (2-7) (yield: 65 mol %).

11.8 g (99 mmol) of thionyl chloride was added to 20 ml of a toluene solution of 17.6 g (66 mmol) of Compound (2-8), and a catalytic amount of N,N-dimethylformamide was added thereto. The mixture was heated to 80° C., and after stirring for 2 hours, the solvent was removed off by distillation. The residue was added dropwise to 30 ml of a tetrahydrofuran (THF) solution of 11.8 g (30 mmol) of Compound (2-7), 10 mg of Irganox 1010 (trade name, manufactured by Ciba Specialty Chemicals), and 7.1 g (90 mmol) of pyridine (Py) under cooling on ice under nitrogen atmosphere. After the completion of dropwise addition, the mixture was stirred for 3 hours and then further for 1 hour at room temperature. After addition of ethyl acetate and water thereto, the mixture was separated, and the organic layer was washed with water, 0.5N aqueous hydrochloric acid, and water, in that order. The organic layer was dried over magnesium sulfate, and the solvent was removed off by distillation under reduced pressure. Purification by silica gel column chromatography gave 20.0 g of Exemplified compound (2) (yield: 75 mol %).

<Identification Data of Exemplified Compound (2)>
$^1$H-NMR (CDCl$_3$, 300 MHz):
0.75-1.25 (m, 36H), 1.40-1.65 (m, 4H), 1.65-2.00 (m, 16H), 2.10-2.25 (m, 4H), 2.45-2.60 (m, 2H), 4.40-4.55 (m, 4H), 5.92 (d, 1H), 6.20 (dd, 1H), 6.50 (d, 1H), 7.21 (d, 2H)
Mass (m/z, POSI)=890

Examples 2 and 3

Preparation of Exemplified Compounds (1) and (3)

Exemplified compounds (1) and (3) were prepared in the same manner as in Example 1, except that 4-hydroxybutyl acrylate used in Example 1 was replaced with 2-hydroxyethyl acrylate or 4-hydroxybutyl methacrylate, respectively.
<Identification Data of Exemplified Compound (1)>
$^1$H-NMR (CDCl$_3$, 300 MHz):
0.75-1.25 (m, 36H), 1.40-1.65 (m, 4H), 1.65-2.00 (m, 12H), 2.10-2.25 (m, 4H), 2.45-2.60 (m, 2H), 4.40-4.55 (m, 4H), 5.92 (d, 1H), 6.20 (dd, 1H), 6.50 (d, 1H), 7.21 (d, 2H)
Mass (m/z, POSI) 863
<Identification Data of Exemplified Compound (3)>
$^1$H-NMR (CDCl$_3$, 300 MHz):
0.75-1.25 (m, 36H), 1.40-1.65 (m, 4H), 1.65-2.10 (m, 19H), 2.10-2.25 (m, 4H), 2.45-2.60 (m, 2H), 4.40-4.55 (m, 4H), 5.58 (d, 1H), 6.15 (d, 1H), 7.21 (d, 2H)
Mass (m/z, POSI)=905

Example 4

Preparation of Exemplified Compounds (78) to (95)

Exemplified compounds (78) to (95) were prepared in the same manner as in Example 1. The structure of each of the thus-obtained compounds was identified in the same manner as in Examples 1 to 3, based on various spectroscopic data, such as the data of NMR spectrum and Mass spectrum.

The phase-transition temperatures of the respective compounds obtained in Examples 1 to 4 are shown in Table 1. In Table 1, "Cr" represents crystalline phase, "Ne" represents nematic phase, "Iso" represents isotropic phase, and "Col" represents columner phase, respectively. Numbers represent the phase transition temperatures in the course of heating.

TABLE 1

| Exemplified compound | Phase-transition temperature (° C.) |
| --- | --- |
| (1) | Cr 180 Ne 280 Iso |
| (2) | Cr 142 Ne 250 Iso |
| (78) | Cr 137 Ne 210 Iso |

TABLE 1-continued

| Exemplified compound | Phase-transition temperature (° C.) |
|---|---|
| (79) | Cr 147 Ne 163 Iso |
| (80) | Col 102 Ne 135 Iso |
| (81) | Cr 119 Ne 153 Iso |
| (82) | Ne 114 Iso |
| (83) | Ne 124 Iso |
| (84) | Cr 170 Ne 200 Iso |
| (85) | Cr 108 Ne 143 Iso |
| (86) | Cr 107 Ne >180 Iso |
| (87) | Cr 170 Ne 206 Iso |
| (88) | Cr 105 Ne 117 Iso |
| (89) | Cr 156 Ne 187 Iso |
| (90) | Cr 123 Ne 143 Iso |
| (91) | Cr 135 Iso |
| (92) | Cr 112 Ne 123.5 Iso |
| (93) | Cr 95 Ne 121 Iso |
| (94) | Cr 95 Ne 140 Iso |
| (95) | Cr 193 Iso |

Example 5

Preparation of Polymerization Film (A Plate) Oriented Almost in the Horizontal Direction by Using Exemplified Compound (2)

A solution of 100 parts by mass of Exemplified compound (2) and 4 parts by mass of a polymerization initiator (Irgacure 819, trade name, manufactured by Ciba Specialty Chemicals) dissolved in 350 parts by mass of chloroform, was applied, by spin-coating, on a glass plate carrying an homogeneously oriented polyimide orientation film, thereby to form a thin film. The liquid crystal compound was oriented at a substrate temperature of 140° C., thereby to give a uniformly oriented film. Then, the liquid crystal compound was polymerized by irradiation of ultraviolet ray at an intensity of 400 mJ/cm², and the resultant film was cooled, to give a polymerization film in the immobilized orientation state of the liquid crystal compound. In this manner, films having a respective thicknesses of 2.10 μm (Film a), 3.52 μm (Film b), or 3.03 μm (Film b-2) were obtained, by adjusting the solution concentration, and the spin-coating velocity and period of time.

The Films a, b and b-2 thus prepared were analyzed by using an automatic birefringence meter (KOBRA-21ADH, trade name, manufactured by Oji Scientific Instruments Co., Ltd.), and the results are summarized in Table 2.

TABLE 2

| Measurement wavelength | | 450 nm | 550 nm | 650 nm |
|---|---|---|---|---|
| Film a | Re | 78 nm | 99 nm | 106 nm |
| | Rth | 40 nm | 50 nm | 54 nm |
| | Re/Re (550) | 0.788 | 1 | 1.071 |
| Film b | Re | 127 nm | 160 nm | 172 nm |
| | Rth | 64 nm | 80 nm | 87 nm |
| | Re/Re (550) | 0.800 | 1 | 1.075 |
| Film b-2 | Re | 110 nm | 137 nm | 147 nm |
| | Rth | 55 nm | 69 nm | 74 nm |
| | Re/Re (550) | 0.803 | 1 | 1.073 |

As is apparent from the results in Table 2, the Films a, b and b-2 each had a positive Re at each measurement wavelength and a Re/Rth ratio of about 2 at each wavelength, which indicates that the Exemplified compound (2) was oriented on the film plane almost in the horizontal direction.

Further, the Re increased as the measurement wavelength became longer, and the value of Re/Re(550) indicated that the aforementioned anisotropy films had a retardation Re that satisfied the relationships in mathematical formulae (8) and (9).

$$0.5 < Re(450\ nm)/Re(550\ nm) < 1.0 \qquad \text{Mathematical formula (8)}$$

$$1.05 < Re(650\ nm)/Re(550\ nm) < 1.5 \qquad \text{Mathematical formula (9)}$$

Example 6

Preparation of Almost Vertically Oriented Polymerization Film (C Plate) by using Exemplified Compound (2)

(Formation of Oriented Film)

A polyimide-based liquid crystal orientation material (JALS 684, trade name, manufactured by JSR Corp.) was diluted with γ-butylolactone, and the mixture was applied on a glass plate. The thus-coated glass plate was dried at 80° C. for 15 minutes, and then heated at 200° C. for 60 minutes, followed by cooling and then rubbing, to give an oriented film. The film thickness of the oriented film was 0.1 μm.

On the thus-obtained glass plate with the JALS 684 film, applied, by bar-coating, was a solution of 100 parts by mass of Exemplified compound (2) and 2 parts by mass of the following polymerization initiator dissolved in 350 parts by mass of chloroform, and the resultant film was heated to 140° C., to male the liquid crystal compound be oriented. Then, the liquid crystal compound was polymerized by irradiation of ultraviolet ray at an intensity of 1,200 mJ/cm², and the resultant film was cooled, to give a polymerization film having an immobilized orientation state of the liquid crystal compound. In this manner, films respectively having thicknesses of 4.43 μm (Film c), 2.49 μm (Film d) and 2.41 μm (Film d-2) were prepared, by adjusting the number of the coating bar, and the coating solution concentration.

[Chemical formula 39]

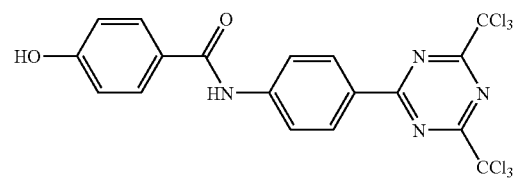

Polymerization initiator

The thus-obtained Films c, d and d-2 were analyzed by using an automatic birefringence meter (KOBRA-21ADH, trade name, manufactured by Oji Scientific Instruments Co., Ltd.), and the results are summarized in Table 3.

TABLE 3

| Measurement wavelength | | 450 nm | 550 nm | 650 nm |
|---|---|---|---|---|
| Film c | Re | −2 nm | 0 nm | 1 nm |
| | Rth | −165 nm | −210 nm | −224 nm |
| | Rth/Rth (550) | 0.786 | 1 | 1.067 |
| Film d | Re | 0 nm | 0 nm | 0 nm |
| | Rth | −96 nm | −122 nm | −130 nm |
| | Rth/Rth (550) | 0.787 | 1 | 1.066 |
| Film d-2 | Re | 0 nm | 0 nm | 0 nm |
| | Rth | −93 nm | −118 nm | −126 nm |
| | Rth/Rth (550) | 0.788 | 1 | 1.065 |

As is apparent from the results in Table 3, the Films c, d and d-2 each had a Re value of about 0 (zero) at each measurement wavelength and a Rth value of negative at each wavelength, which indicates that the Exemplified compound (2) was oriented on the film plane almost vertically.

Further, the Rth value decreased as the measurement wavelength became longer, and the value of Rth/Rth(550) indicated that the anisotropy film had a negative retardation Rth (550 nm) in the thickness direction and that the retardation Rth at a particular wavelength satisfied the relationships in mathematical formulae (12) and (13).

$$0.6 < Rth(450\ nm)/Rth(550\ nm) < 0.99 \quad \text{Mathematical formula (12)}$$

$$1.01 < Rth(650\ nm)/Rth(550\ nm) < 1.35 \quad \text{Mathematical formula (13)}$$

Example 7

Preparation of Almost Helically Oriented Polymerization Film by Using Exemplified Compound (2)

A polyimide-based liquid crystal orientation material (SE-150, trade name, manufactured by Nissan chemical Industry Corp.) was diluted with γ-butylolactone, and the mixture was applied on a glass plate. The thus-coated film was dried at 80° C. for 15 minutes, and then heated at 250° C. for 60 minutes, followed by cooling and then rubbing, to give an oriented film. The film thickness of the oriented film was 0.1 μm.

On the thus-obtained oriented film, applied was a solution of 100 parts by mass of Exemplified compound (2), 3 parts by mass of a polymerization initiator (Irgacure 907, trade name, manufactured by Nihon Ciba-Geigy K.K.), 1 part by mass of a sensitizer (Kayacure DETX, trade name, manufactured by Nippon Kayaku Co., Ltd.), 10 parts by mass of a chiral agent (K-1 below), and 0.4 parts by mass of an additive (SH-1 below) dissolved in 500 parts by mass of chloroform. The thus-coated film was heated to 140° C., and then irradiated with ultraviolet ray under nitrogen atmosphere at an intensity of 400 mJ/cm², thereby to allow the liquid crystal compound to undergo polymerization. Then, the resultant film was cooled, to give a polymerization film having an immobilized orientation state of the liquid crystal compound. In this manner, films respectively having thicknesses of 2.05 μm (Film e) and 2.10 μm (Film f) were prepared, by adjusting the coating solution concentration.

[Chemical formula 41]

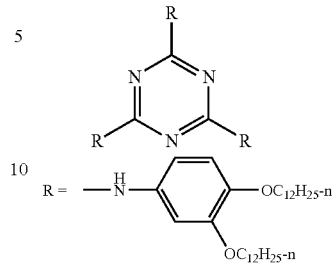

SH-1

The Films e and f thus prepared were analyzed by using an automatic birefringence meter (KOBRA-21ADH, trade name, manufactured by Oji Scientific Instruments Co., Ltd.), and the results are summarized in Table 4

TABLE 4

| Measurement wavelength | | 450 nm | 550 nm | 650 nm |
|---|---|---|---|---|
| Film e | Re | 0 nm | 0 nm | 0 nm |
| | Rth | 66 nm | 82 nm | 89 nm |
| | Rth/Rth (550) | 0.805 | 1 | 1.085 |
| Film f | Re | 0 nm | 0 nm | 0 nm |
| | Rth | 68 nm | 85 nm | 91 nm |
| | Rth/Rth (550) | 0.800 | 1 | 1.071 |

As is apparent from the results in Table 4, the Films e and f each had a Re of 0 (zero) at each measurement wavelength and a positive Rth at each measurement wavelength. The results indicate that the Exemplified compound (2) was oriented almost helically, and that the helical axis was almost perpendicular to the substrate plane.

Further, the Rth increased as the measurement wavelength became longer, and the value of Rth/Rth (550) indicated that the anisotropy film had a positive retardation Rth (550 nm) in the thickness direction and that the retardation Rth at a particular wavelength satisfied the relationships in mathematical formulae (14) and (15).

$$0.6 < Rth(450\ nm)/Rth(550\ nm) < 0.99 \quad \text{Mathematical formula (14)}$$

$$1.01 < Rth(650\ nm)/Rth(550\ nm) < 1.35 \quad \text{Mathematical formula (15)}$$

[Chemical formula 40]

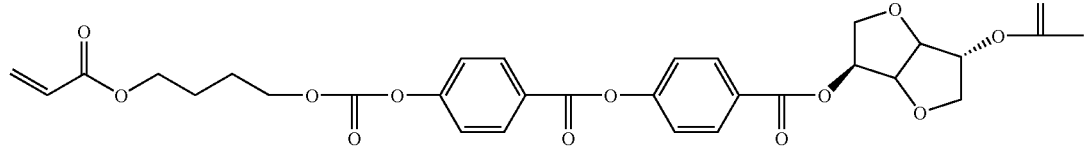

K-1

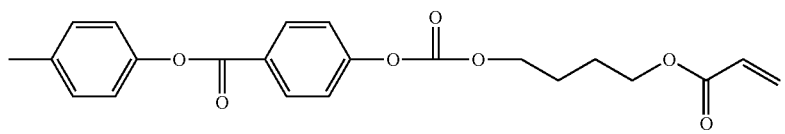

Example 8

Preparation Of Brightness-Improving Film

On a commercially available cellulose acetate film of thickness 80 μm (Fujitac TD80UF, trade name, manufactured by Fuji Photo Film Co., Ltd.), a cholesteric liquid crystal layer (thickness: 5 μm) showing circular dichroism in a wavelength range of 400 to 700 nm was formed, and the resultant film was coated with an acrylic adhesive, followed by laminating thereto the Film c, which was the optically anisotropic film (the optically anisotropic film (A)) formed in Example 6, and then separating the support of glass plate therefrom.

Further, on the resultant Film c, a quarter-wavelength plate (thickness 60 μm) of a stretched and oriented polycarbonate film having a Re of 137 nm was laminated, to give a brightness-improving film.

Further, the resultant quarter-wavelength plate was coated with an adhesive, and a polarizing plate was laminated thereon such that an angle formed between the slow axis of the quarter-wavelength plate and the transmission axis of the polarizing plate would be 45 degrees.

By using the brightness-improving film laminated with the polarizing plate, a liquid crystal display was assembled so as to have a diffusion film, the aforementioned brightness-improving film (the lamination of: cholesteric liquid crystal layer/Film c/quarter-wavelength plate), the polarizing plate, a liquid crystal cell, and a polarizing plate, provided in that order on a backlight with an light guide plate (a light panel), and the front-side brightness (cd/m$^2$) of the thus-assembled LCD at white level was measured, by using a spectral radiometer/brightness meter.

Separately, the measurement in the same manner as above was made with a LCD having the same constitution except that no brightness-improving film was utilized. Thus, the ratio in brightness (i.e. a brightness-improving factor) between those two liquid crystal displays was determined, and as a result, the value of brightness in the case where the brightness-improving film was used was 1.31 times higher than the brightness in the case where no brightness-improving film was used.

Further, it was also confirmed by the observation with the naked eye that the irregularity in color at the oblique view angle direction (45°) was extremely small.

Example 9

Preparation of Optically Anisotropic Film Having Optically Anisotropic Films (A) and (B)

<Preparation of Optically Anisotropic Film B-1 (Optically Anisotropic film (B))>
(Preparation of Cellulose Acetate Solution)
The components of the following composition were charged into a mixing talk, followed by stirring to dissolve the components each other. Thus, a cellulose acetate solution A was prepared.
(Composition of Cellulose Acetate Solution A)

| | |
|---|---|
| Cellulose acetate (acetylation degree 2.86) | 100.0 mass parts |
| Methylene chloride (first solvent) | 402.0 mass parts |
| Methanol (second solvent) | 60.0 mass parts |

(Preparation of Matting Agent Solution)
20 parts by mass of silica particles of average particle size 16 nm (AEROSIL R972, trade name, manufactured by Nippon Aerosil Co., Ltd.) and 80 parts by mass of methanol were stirred and mixed well for 30 minutes, to give a silica particle dispersion liquid. The dispersion liquid together with the components of the following composition were placed in a dispersing machine, and the mixture was stirred for 30 minutes or more, to dissolve the components each other, thereby to give a matting agent solution.
(Composition of Matting Agent Solution)

| | |
|---|---|
| Silica particle dispersion liquid having an average particle size of 16 nm | 10.0 mass parts |
| Methylene chloride (first solvent) | 76.3 mass parts |
| Methanol (second solvent) | 3.4 mass parts |
| Cellulose acetate solution A | 10.3 mass parts |

(Preparation of Additive Solution)
The components of the following composition were charged into a mixing tank, followed by stirring under heating, to dissolve the components each other. Thus, a cellulose acetate solution was prepared.
(Composition of Additive Solution)

| | |
|---|---|
| Compound for lowering optical anisotropy (A-01) | 49.3 mass parts |
| Wavelength dispersion adjusting agent (UV-01) | 7.6 mass parts |
| Methylene chloride (first solvent) | 58.4 mass parts |
| Methanol (second solvent) | 8.7 mass parts |
| Cellulose acetate solution A | 12.8 mass parts |

The logP value of the compound A-01 was 2.9.

[Chemical formula 42]

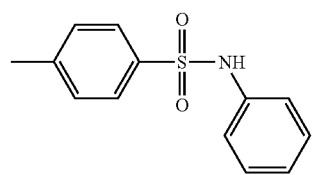

A-01

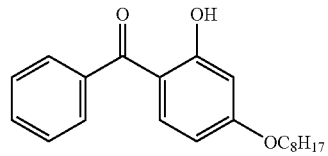

UV-01

<Preparation of Optically Anisotropic Film B-1>
After respectively subjecting to filtration, 94.6 parts by mass of the cellulose acetate solution A, 1.3 parts by mass of the matting agent solution, and 4.1 parts by mass of the additive solution were mixed together, and the mixture was cast in a band-casting machine. The mass ratios of the compound for lowering optical anisotropy (A-01) and the wavelength dispersion adjusting agent (UV-01) to cellulose acetate in the composition were 12% and 1.8%, respectively. The resultantly cast film was separated from the band at a residual solvent content of 30%, followed by drying at 140° C. for 40 minutes, to give a cellulose acetate film. The residual solvent content of the cellulose acetate film obtained was 0.2%, and the film thickness was 40 μm.

The film had a $Re_{(630)}$ of 0.3 nm, a $Rth_{(630)}$ of 3.2 nm, a $|Re_{(400)}-Re_{(700)}|$ of 1.2 nm, a $|Rth_{(400)}-R_{th(700)}|$ of 7.5 nm, a Tg of 134.3° C., a haze of 0.34%, and a ΔRth(10% RH-80% RB) of 24.9 nm. The film is designated as Optically anisotropic film B-1.

<Preparation of Polarizing Plate 1 with Optically Anisotropic film B-1>.

A polarizing film was prepared by allowing adsorption of iodine on a stretched polyvinylalcohol film. A commercially available cellulose acetate film (Fujitac TD80UF, trade name, manufactured by Fuji Photo Film Co., Ltd.) was saponified, by using a polyvinylalcohol-based adhesive. Then, the thus-saponified cellulose acetate film was laminated on one side of the polarizing film, and the Optically anisotropic film B-1 on the other side, by using a polyvinylalcohol-based adhesive, thereby to give a Polarizing plate 1.

<Preparation of Polarizing Plate 2 with Film d-2>

To the Optically anisotropic film B-1 side of the aforementioned Polarizing plate 1 with Optically anisotropic film B-1, a polycarbonate film (B-2) of positive A plate (Re(550 nm)=133.77 nm, Re(450 nm n)/Re(550 nm)=0.796, Re(650 nm)/Re(550 nm)=1.053) was laminated, such that the slow axis direction would be perpendicular to the transmission axis of the polarizing film. Then, thereto, the aforementioned Film d-2 of the Optically anisotropic film (A) on the glass plate was laminated, and the resultant laminate was heated under pressure with rollers; and then, the glass plate, which was the support of the Film d-2, was removed, to give a Polarizing plate 2 with the Film d-2.

<Preparation of IPS-Mode Liquid Crystal Display Device>

On one side of an IPS-mode liquid crystal cell (commercially available liquid crystal cell product, Liquid Crystal TV32Z1000 (trade name), manufactured by Toshiba Corp.), the aforementioned Polarizing plate 1 was laminated, such that the transmission axis of the polarizing film of Polarizing plate 1 would be in parallel with the rubbed direction of the liquid crystal cell and that the Polarizing plate 1 would be laminated at the Optically anisotropic film B-1 side to be the liquid crystal cell side. Subsequently, the Polarizing plate 2 was laminated onto the other side of the IPS-mode liquid crystal cell, such that the slow axis of the polycarbonate film (B-2) of positive A plate in the Polarizing plate 2 would be in parallel with the rubbed direction of the liquid crystal cell and that the Polarizing plate 2 would be laminated at the polycarbonate film (B-2) side to be the liquid crystal cell side. Thus, a liquid crystal display device was prepared.

<Measurement of Light Leakage from Liquid Crystal Display Device Prepared>

The brightness of the thus-mounted liquid crystal display device from an oblique angle direction was measured. A ratio of the thus-measured brightness at the oblique direction to the brightness of the backlight was determined, and the resultant ratio is designated as a transmittance. Here, the brightness when displaying black was measured, at a constant polar angle of 60°, and the highest brightness was utilized, varying the directional angle from 0° to 360°. The brightness of backlight was a value measured from the front of the LCD. The light leakage measured was 0.000254.

Example 10

An IPS-mode liquid crystal display device was prepared in the same manner as in Example 9, except that the polycarbonate film (B-2) used in Example 9 was replaced with a Zeonor (trade name, manufactured by Zeon Corporation) film (B-3) of positive A plate (Re(550 nm)=133.77 nm, Re(450 nm)/Re(550 nm)=0.988, Re(650 nm)/Re(550 nm)=1.00). The light leakage of the thus-prepared IPS-mode liquid crystal display device was determined in the same manner as in Example 9. As a result, the light leakage was found to be 0.000283.

Comparative Example 1

Comparison with Usual Polymerizable Rod-Shaped Liquid Crystal Compound

Vertically-orientated and immobilized retardation films of film thickness approximately 1.7 μm or 1.4 μm, respectively, were prepared in the same manner as in Example 6, except that the following usual polymerizable liquid crystal compound NG-1 was used instead of the Exemplified compound (2) and that the orientation and immobilization were conducted at a temperature of 100° C.

The optical anisotropy of the thus-prepared retardation films was determined as the dependence of Re on light incident angle, using an automatic birefringence meter (KOBRA-21ADH, trade name, manufactured by Oji Scientific Instruments Co., Ltd.), and separately, the film thicknesses d were measured. Then, the Δn was calculated with those optical anisotropy and film thickness d, according to formula: Δn=Re/d. Each of the optically anisotropic films showed the following values: Δn(450 nm)=0.116, Δn(550 nm)=0.104, Δn(650 nm)=0.100; and thus: Δn(450 nm)/Δn(550 nm)=1.12, and Δn(650 nm)/Δn(550 nm)=0.096.

[Chemical formula 43]

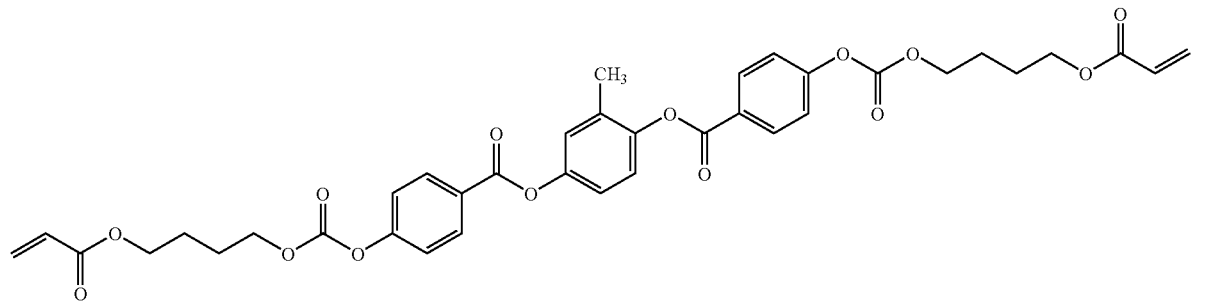

NG-1

Comparative Example 2

A film was prepared in the same manner as in Example 8, except that the Film c of brightness-improving film as prepared in Example 8 was replaced with the retardation film as prepared in Comparative Example 1, which showed normal wavelength dispersion (Re/Rth=0 nm/−210 nm). The thus-prepared film for comparison had a brightness-improving factor of 1.27, as measured in the same manner as in Example 8.

Further, it was also confirmed with the naked eye that the irregularity in color at the oblique view angle direction (45°) was conspicuously large.

Comparative Example 3

An IPS-mode liquid crystal display device was prepared in the same manner as in Example 9, except that the Film d-2 and the polycarbonate film (B-2) used in Example 9 were replaced with the retardation film as prepared in Comparative Example 1, which showed normal wavelength dispersion (Re/Rth=0 nm/−118 nm), and the Zeonor film (B-3) as utilized in Example 10, respectively. The light leakage of the thus-prepared IPS-mode liquid crystal display device was determined in the same manner as in Example 9. As a result, the light leakage was found to be 0.000319.

By comparing the results in Examples 9 and 10 with that in Comparative Example 3, it is found that the optically anisotropic film (A) as an IPS retardation film is preferably a liquid crystal having reverse wavelength dispersion. Further, it is also found that as the optically anisotropic film (B) of a positive A plate film, a film with reverse wavelength dispersion is effective for use in reducing light leakage.

Example 11

Experiments were conducted in the same manner as in the examples described in JP-A-2004-326089, excepted that the Film b-2 as prepared in the Example 5 above was used in place of the stretched polymer film 11 (the positive A plate a) described in the examples of JP-A-2004-326089. As the results, it is found that the light leakage from the transmission VA liquid crystal display device including the Film b-2 was reduced drastically and that there was almost no color shift observed. Further, it is noted that the Film b-2 had a thickness of 3.03 μm, which is remarkably thinner than the stretched polymer film 11 of film thickness 80 μm. Thus, use of the Film b-2 allows remarkable reduction of the film thickness.

INDUSTRIAL APPLICABILITY

The polymerizable compound with reverse wavelength dispersion of the present invention can be favorably used as a polymerizable liquid crystal compound, and used in a polymerizable liquid crystal composition. Further, the optical film of the present invention having the liquid crystal compound immobilized therein can be favorably used for a retardation sheet having reverse wavelength dispersion of birefringence, such as a broadband λ/4 plate, or for a polarizing plate and a liquid crystal display.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2006-339233 filed in Japan on Dec. 15, 2006, and Patent Application No. 2007-097315 filed in Japan on Apr. 3, 2007, each of which is entirely herein incorporated by reference.

The invention claimed is:

1. A liquid crystal composition, comprising at least one of a compound represented by formula (1):

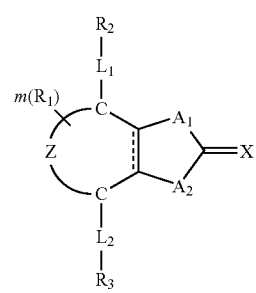

Formula (1)

wherein $A_1$ and $A_2$ each independently represent a group selected from the group consisting of —O—, —NR— (in which R represents a hydrogen atom or a substituent), —S—, and —CO—; Z forms a benzene ring with the C—C=C—C or C=C—C=C in the formula; $R_1$, $R_2$, and $R_3$ each independently represent a substituent; m represents an integer of 0 to 4; $L_1$ and $L_2$ each independently represent a single bond or a divalent linking group; X is selected from =O, =S, =$NR_4$, and $C(R_5)R_6$ wherein $R_4$, $R_5$ and $R_6$ each independently represent a substituent; and at least one of R, $R_1$, $R_2$, $R_3$, and $R_4$ is substituted with a polymerizable group, wherein the content of a liquid crystal compound in the liquid crystal composition is at least 30 mass %.

2. The liquid crystal composition compound according to claim 1, wherein the compound represented by formula (1) is a compound represented by formula (2):

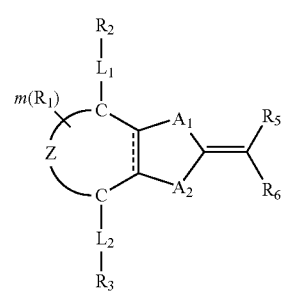

Formula (2)

wherein $A_1$ and $A_2$ each independently represent a group selected from the group consisting of —O—, —NR— (in which R represents a hydrogen atom or a substituent), —S—, and —CO—; Z forms a benzene ring with the C—C=C—C or C=C—C=C in the formula; $R_1$, $R_2$, and $R_3$ each independently represent a substituent; m represents an integer of 0 to 4; $L_1$ and $L_2$ each independently represent a single bond or a divalent linking group; $R_5$ and $R_6$ each independently represent a substituent; and at least one of R, $R_1$, $R_2$, $R_3$, $R_5$, and $R_6$ is substituted with a polymerizable group.

3. The liquid crystal composition according to claim 1, wherein the polymerizable group is an addition polymerization group.

4. The liquid crystal composition according to claim 1, wherein $R_2$ and $R_3$ each independently are a phenyl group having a substituted or unsubstituted benzoyloxy group at the 4-position, a phenyl group having a substituted or unsubstituted cyclohexyl group at the 4-position, a cyclohexyl group having a substituted or unsubstituted phenyl group at the 4-position, or a cyclohexyl group having a substituted or unsubstituted cyclohexyl group at the 4-position.

5. The liquid crystal composition according to claim 1, wherein the polymerization group is represented by any one of formulae P1, P2, P3, or P4:

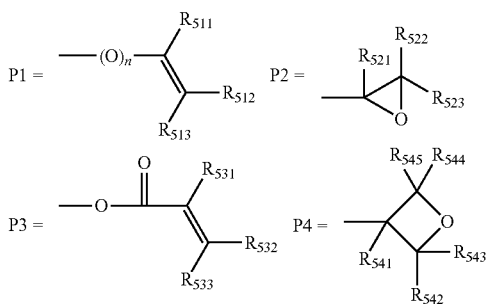

wherein $R_{511}$, $R_{512}$, $R_{513}$, $R_{521}$, $R_{522}$, $R_{523}$, $R_{531}$, $R_{532}$, $R_{533}$, $R_{541}$, $R_{542}$, $R_{543}$, $R_{544}$, and $R_{545}$ each independently represent a hydrogen atom or an alkyl group; and n represents 0 (zero) or 1.

6. The liquid crystal composition according to claim 1, wherein the compound shows a nematic phase or a smectic A phase.

7. An optically anisotropic film, which is formed with the liquid crystal composition according to claim 1, wherein the compound is oriented almost vertically and immobilized.

8. An optically anisotropic film, which is formed with the liquid crystal composition according to claim 1, wherein the compound is oriented almost horizontally and immobilized.

9. An optically anisotropic film, which is formed with the liquid crystal composition according to claim 1, wherein the compound is oriented cholesterically and immobilized.

10. The optically anisotropic film according to claim 9, wherein the helical axis of the cholesteric phase and the plane direction of a transparent support are crossed to each other almost orthogonally.

11. A brightness-improving film, comprising a cholesteric liquid crystal film, a quarter-wavelength plate, and an optically anisotropic film placed between them, wherein the optically anisotropic film is the optically anisotropic film according to claim 7.

12. An optically anisotropic film, comprising the optically anisotropic film according to claim 7, and at least one layer of another optically an isotropic film.

13. The optically anisotropic film according to claim 12, wherein the another optically anisotropic film is a positive A plate film.

14. The optically anisotropic film according to claim 12, wherein the another optically anisotropic film is a positive A plate film that satisfies relationships in mathematical formulae (I) and (II)

$Re(450\ nm)/Re(550\ nm)<1.0$     Mathematical formula (I)

$Re(650\ nm)/Re(550\ nm)>1.0$.    Mathematical formula (II)

15. A retardation sheet, comprising the optically anisotropic film according to claim 7.

16. A polarizing plate, comprising the retardation sheet according to claim 15.

17. A liquid crystal display device, comprising the retardation sheet according to claim 15.

18. An IPS-mode liquid crystal display device, comprising the optically anisotropic film according to claim 12.

19. A VA-mode liquid crystal display device, comprising the optically anisotropic film according to claim 8.

20. A view angle-adjustable liquid crystal display device, comprising the optically anisotropic film according to claim 9.

21. The liquid crystal composition according to claim 1, wherein the content of the liquid crystal compound in the liquid crystal composition is 30 to 90 mass %.

* * * * *